United States Patent
Smythe et al.

(10) Patent No.: US 12,269,856 B2
(45) Date of Patent: *Apr. 8, 2025

(54) HEPCIDIN ANALOGUES AND USES THEREOF

(71) Applicant: Protagonist Therapeutics, Inc., Newark, CA (US)

(72) Inventors: Mark Leslie Smythe, Bardon (AU); Gregory Thomas Bourne, Brisbane (AU); Simone Vink, Taringa (AU); Brian Troy Frederick, Ben Lomand, CA (US); Praveen Madala, Brisbane (AU); Anne Pernille Tofteng Shelton, Valby (DK); Jacob Ulrik Fog, Bagsvaerd (DK)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,490

(22) Filed: Sep. 28, 2023

(65) Prior Publication Data

US 2024/0174726 A1    May 30, 2024

Related U.S. Application Data

(63) Continuation of application No. 17/099,308, filed on Nov. 16, 2020, now Pat. No. 11,807,674, which is a continuation of application No. 16/839,368, filed on Apr. 3, 2020, now abandoned, which is a continuation of application No. 16/553,486, filed on Aug. 28, 2019, now abandoned, which is a continuation of application No. 16/289,451, filed on Feb. 28, 2019, now Pat. No. 10,501,515, which is a continuation of application No. 16/037,982, filed on Jul. 17, 2018, now Pat. No. 10,442,846, which is a continuation of application No. 15/828,214, filed on Nov. 30, 2017, now Pat. No. 10,030,061, which is a continuation of application No. 15/720,333, filed on Sep. 29, 2017, now abandoned, which is a continuation of application No. 14/775,469, filed as application No. PCT/US2014/030352 on Mar. 17, 2014, now Pat. No. 9,822,157.

(60) Provisional application No. 61/800,048, filed on Mar. 15, 2013, provisional application No. 61/800,284, filed on Mar. 15, 2013.

(51) Int. Cl.
| | |
|---|---|
| A61K 38/10 | (2006.01) |
| A61K 38/04 | (2006.01) |
| A61K 38/08 | (2019.01) |
| C07K 5/00 | (2006.01) |
| C07K 7/00 | (2006.01) |
| C07K 14/575 | (2006.01) |
| C07K 16/00 | (2006.01) |
| C07K 17/00 | (2006.01) |
| A61K 38/00 | (2006.01) |

(52) U.S. Cl.
CPC ........... *C07K 14/575* (2013.01); *A61K 38/00* (2013.01)

(58) Field of Classification Search
CPC .............................. C07K 14/575; A61K 38/00
See application file for complete search history.

(56) References Cited

U.S. PATENT DOCUMENTS

| | | | |
|---|---|---|---|
| 4,684,620 | A | 8/1987 | Hruby et al. |
| 4,724,229 | A | 2/1988 | Ali |
| 5,192,746 | A | 3/1993 | Lobl et al. |
| 5,494,897 | A | 2/1996 | Ishikawa et al. |
| 5,569,741 | A | 10/1996 | Coy et al. |
| 5,990,084 | A | 11/1999 | Richter et al. |
| 6,087,334 | A | 7/2000 | Beeley et al. |
| 6,235,711 | B1 | 5/2001 | Dutta |
| 7,534,764 | B2 | 5/2009 | Ganz et al. |
| 7,589,170 | B1 | 9/2009 | Smythe et al. |
| 7,718,598 | B1 | 5/2010 | Smythe et al. |
| 7,745,391 | B2 | 6/2010 | Mintz et al. |
| 8,313,950 | B2 | 11/2012 | Rovin et al. |
| 8,435,941 | B2 | 5/2013 | Ganz et al. |
| 8,536,140 | B2 | 9/2013 | Clandinin et al. |
| 8,568,706 | B2 | 10/2013 | Grabstein et al. |
| 8,796,418 | B2 | 8/2014 | Walensky et al. |
| 8,946,150 | B2 | 2/2015 | Gallagher et al. |
| 8,999,935 | B2 | 4/2015 | Huang |
| 9,169,292 | B2 | 10/2015 | Gallagher et al. |

(Continued)

FOREIGN PATENT DOCUMENTS

| | | |
|---|---|---|
| CA | 2015761 A1 | 11/1990 |
| CN | 101307085 A | 11/2008 |

(Continued)

OTHER PUBLICATIONS

Adams and MacMillan, "Investigation of peptide thioester formation via N→Se acyl transfer." Journal of Peptide Science (2013); 19 (2): 65-73.

(Continued)

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

The present invention relates, inter alia, to certain hepcidin peptide analogues, including peptides and dimers thereof, and to the use of the peptides and peptide dimers in the treatment and/or prevention of a variety of diseases, conditions or disorders, including treatment and/or prevention of iron overload diseases, which include hereditary hemochromatosis and iron-loading anemias, and other conditions and disorders described herein.

15 Claims, 7 Drawing Sheets
Specification includes a Sequence Listing.

(56) References Cited

U.S. PATENT DOCUMENTS

| | | |
|---|---|---|
| 9,315,545 B2 | 4/2016 | Merutka |
| 9,822,157 B2 | 11/2017 | Smythe et al. |
| 10,030,061 B2 | 7/2018 | Smythe et al. |
| 10,442,846 B2 | 10/2019 | Smythe et al. |
| 10,501,515 B2 | 12/2019 | Vink et al. |
| 11,472,842 B2 | 10/2022 | Bourne et al. |
| 11,753,443 B2 | 9/2023 | Bourne et al. |
| 11,807,674 B2 | 11/2023 | Smythe et al. |
| 2003/0166138 A1 | 9/2003 | Kinsella et al. |
| 2003/0166514 A1 | 9/2003 | Jones et al. |
| 2004/0052785 A1 | 3/2004 | Goodman et al. |
| 2004/0123343 A1 | 6/2004 | La Rosa et al. |
| 2004/0152868 A1 | 8/2004 | Larsen et al. |
| 2006/0166881 A1 | 7/2006 | Hotchkiss et al. |
| 2006/0183884 A1 | 8/2006 | Blaschuk et al. |
| 2007/0032417 A1 | 2/2007 | Baell |
| 2007/0191272 A1 | 8/2007 | Stemmer et al. |
| 2007/0197430 A1 | 8/2007 | Baell et al. |
| 2008/0019913 A1 | 1/2008 | Polt et al. |
| 2008/0213277 A1 | 9/2008 | Sasu et al. |
| 2008/0260820 A1 | 10/2008 | Borrelly et al. |
| 2008/0300180 A1 | 12/2008 | Schambye et al. |
| 2009/0053819 A1 | 2/2009 | Seymour et al. |
| 2009/0257952 A1 | 10/2009 | Cochran et al. |
| 2010/0151487 A1 | 6/2010 | Rovin et al. |
| 2010/0190710 A1 | 7/2010 | Chemtob et al. |
| 2010/0196441 A1 | 8/2010 | Sondermeijer et al. |
| 2011/0118186 A1 | 5/2011 | Schteingart et al. |
| 2011/0142889 A1 | 6/2011 | Lee et al. |
| 2011/0282029 A1 | 11/2011 | Holmes et al. |
| 2012/0021975 A1 | 1/2012 | Hoffmann et al. |
| 2012/0040894 A1 | 2/2012 | Ganz et al. |
| 2012/0071422 A1 | 3/2012 | Gallagher et al. |
| 2012/0115930 A1 | 5/2012 | Monia et al. |
| 2013/0029907 A1 | 1/2013 | Gallagher et al. |
| 2013/0172272 A1 | 7/2013 | Gallagher et al. |
| 2013/0183755 A1 | 7/2013 | Gallagher et al. |
| 2013/0310303 A1 | 11/2013 | Eldar-Finkelman et al. |
| 2013/0338132 A1 | 12/2013 | Koshiba et al. |
| 2014/0286953 A1 | 9/2014 | Sasu et al. |
| 2014/0336110 A1 | 11/2014 | Ganz et al. |
| 2015/0056301 A1 | 2/2015 | Kawabe et al. |
| 2015/0118315 A1 | 4/2015 | Wilson |
| 2015/0203555 A1 | 7/2015 | Gellman et al. |
| 2015/0284429 A1 | 10/2015 | Merutka |
| 2016/0039878 A1 | 2/2016 | Gallagher et al. |
| 2016/0199437 A1 | 7/2016 | Wilson |
| 2016/0222076 A1 | 8/2016 | Smythe et al. |
| 2016/0228491 A1 | 8/2016 | Wilson |
| 2017/0051013 A1 | 2/2017 | Merutka |
| 2017/0313754 A1 | 11/2017 | Bourne et al. |
| 2017/0327541 A1 | 11/2017 | Bhandari et al. |
| 2017/0362292 A1 | 12/2017 | Ruchala et al. |
| 2018/0086811 A1 | 3/2018 | Smythe et al. |
| 2018/0100004 A1 | 4/2018 | Smythe et al. |
| 2019/0002503 A1 | 1/2019 | Bourne et al. |
| 2019/0185535 A1 | 6/2019 | Smythe et al. |
| 2019/0185536 A1 | 6/2019 | Smythe et al. |
| 2019/0264197 A1 | 8/2019 | Barkan et al. |
| 2020/0017566 A1 | 1/2020 | Bourne et al. |
| 2020/0239516 A1 | 7/2020 | Richelle et al. |
| 2020/0361992 A1 | 11/2020 | Bourne et al. |
| 2021/0061872 A1 | 3/2021 | Liu et al. |
| 2021/0147483 A1 | 5/2021 | Bourne et al. |
| 2022/0348626 A1 | 11/2022 | Smythe et al. |
| 2022/0372099 A1 | 11/2022 | Liu et al. |
| 2024/0016895 A1 | 1/2024 | Liu et al. |
| 2024/0018189 A1 | 1/2024 | Bourne et al. |
| 2024/0066131 A1 | 2/2024 | Bourne et al. |
| 2024/0174726 A1 | 5/2024 | Smythe et al. |
| 2024/0209024 A1 | 6/2024 | Bourne et al. |
| 2024/0209053 A1 | 6/2024 | Bourne et al. |
| 2024/0226225 A1 | 7/2024 | Bourne et al. |

FOREIGN PATENT DOCUMENTS

| | | |
|---|---|---|
| CN | 101358201 A | 2/2009 |
| EP | 21848536.5 | 9/2024 |
| JP | 2010517529 A | 5/2010 |
| JP | 2010536364 A | 12/2010 |
| JP | 2012525124 A | 10/2012 |
| JP | 2016521257 A | 7/2016 |
| JP | 2017530090 A | 10/2017 |
| WO | WO-9217492 A1 | 10/1992 |
| WO | WO-9411018 A1 | 5/1994 |
| WO | WO-9617617 A1 | 6/1996 |
| WO | WO-9725351 A2 | 7/1997 |
| WO | WO-9808871 A1 | 3/1998 |
| WO | WO-9833524 A1 | 8/1998 |
| WO | WO-9926615 A1 | 6/1999 |
| WO | WO-0009560 A2 | 2/2000 |
| WO | WO-0018789 A1 | 4/2000 |
| WO | WO-0018790 A1 | 4/2000 |
| WO | WO-0023474 A1 | 4/2000 |
| WO | WO-0055119 A1 | 9/2000 |
| WO | WO-0055184 A1 | 9/2000 |
| WO | WO-0061580 A1 | 10/2000 |
| WO | WO-0168586 A2 | 9/2001 |
| WO | WO-03066678 A1 | 8/2003 |
| WO | WO-2004011650 A2 | 2/2004 |
| WO | WO-2004092405 A2 | 10/2004 |
| WO | WO-2006032104 A1 | 3/2006 |
| WO | WO-2007138291 A2 | 12/2007 |
| WO | WO-2008097461 A2 | 8/2008 |
| WO | WO-2008101017 A2 | 8/2008 |
| WO | WO-2008134659 A2 | 11/2008 |
| WO | WO-2008140602 A2 | 11/2008 |
| WO | WO-2009002947 A2 | 12/2008 |
| WO | WO-2009077752 A2 | 3/2009 |
| WO | WO-2010065815 A2 | 6/2010 |
| WO | WO-2010116752 A1 | 10/2010 |
| WO | WO-2010124874 A1 | 11/2010 |
| WO | WO-2011091357 A1 | 7/2011 |
| WO | WO-2011149942 A2 | 12/2011 |
| WO | WO-2012052205 A1 | 4/2012 |
| WO | WO-2013086143 A1 | 6/2013 |
| WO | WO-2013172954 A1 | 11/2013 |
| WO | WO-2014059213 A1 | 4/2014 |
| WO | WO-2014127316 A2 | 8/2014 |
| WO | WO-2014145561 A2 | 9/2014 |
| WO | WO-2014165448 A1 | 10/2014 |
| WO | WO-2014165449 A1 | 10/2014 |
| WO | WO-2014210056 A1 | 12/2014 |
| WO | WO-2015054500 A2 | 4/2015 |
| WO | WO-2015157283 A1 | 10/2015 |
| WO | WO-2015176035 A1 | 11/2015 |
| WO | WO-2015183963 A2 | 12/2015 |
| WO | WO-2015200916 A2 | 12/2015 |
| WO | WO-2016004093 A2 | 1/2016 |
| WO | WO-2016011208 A1 | 1/2016 |
| WO | WO-2016054411 A1 | 4/2016 |
| WO | WO-2016054445 A1 | 4/2016 |
| WO | WO-2016109363 A1 | 7/2016 |
| WO | WO-2016115168 A1 | 7/2016 |
| WO | WO-2016195663 A1 | 12/2016 |
| WO | WO-2016200364 A1 | 12/2016 |
| WO | WO-2017011820 A2 | 1/2017 |
| WO | WO-2017068089 A2 | 4/2017 |
| WO | WO-2017117411 A1 | 7/2017 |
| WO | WO-2017165676 A1 | 9/2017 |
| WO | WO-2018022917 A1 | 2/2018 |
| WO | WO-2018022937 A1 | 2/2018 |
| WO | WO-2018048944 A1 | 3/2018 |
| WO | WO-2018089693 A2 | 5/2018 |
| WO | WO-2018128828 A1 | 7/2018 |
| WO | WO-2018136646 A1 | 7/2018 |
| WO | WO-2019051494 A1 | 3/2019 |
| WO | 2019/157268 A1 | 8/2019 |
| WO | WO-2019246273 A1 | 12/2019 |
| WO | WO-2019246349 A1 | 12/2019 |
| WO | WO-2020014646 A1 | 1/2020 |
| WO | WO-2020198682 A1 | 10/2020 |
| WO | WO-2021007433 A1 | 1/2021 |

(56) References Cited

FOREIGN PATENT DOCUMENTS

| WO | WO-2021046246 A1 | 3/2021 |
| WO | WO-2021142373 A1 | 7/2021 |
| WO | WO-2021146441 A1 | 7/2021 |
| WO | WO-2021146454 A1 | 7/2021 |
| WO | WO-2021146458 A1 | 7/2021 |
| WO | WO-2022026629 A1 | 2/2022 |
| WO | WO-2022026631 A1 | 2/2022 |
| WO | WO-2022026633 A1 | 2/2022 |
| WO | WO-2022109328 A1 | 5/2022 |
| WO | WO-2022212696 A1 | 10/2022 |
| WO | WO-2022212698 A1 | 10/2022 |
| WO | WO-2022212700 A2 | 10/2022 |
| WO | WO-2022266060 A1 | 12/2022 |
| WO | WO-2023288017 A2 | 1/2023 |
| WO | WO-2023288019 A2 | 1/2023 |
| WO | WO-2023288028 A2 | 1/2023 |
| WO | WO-2023009891 A2 | 2/2023 |
| WO | WO-2023150618 A2 | 8/2023 |
| WO | WO-2023150630 A2 | 8/2023 |
| WO | 2023/240077 A1 | 12/2023 |
| WO | 2024/011188 A1 | 1/2024 |

OTHER PUBLICATIONS

Andreu, et al., "Formation of Disulfide Bonds in Synthetic Peptides and Proteins" Ch. 7 in Synthetic Peptides and Proteins. In: Pennington M.W., Dunn B.M. (eds) Peptide Synthesis Protocols. Methods in Molecular Biology (1994); 35: 91-169.

Angelucci, et al., "Myelodysplastic Syndromes and Iron Chelation Therapy". Mediterr J Hematol Infect Dis. (Mar. 1, 2017); 9(1): e2017021, 10 pages. eCollection 2017.

Annis, et al., "[10] Disulfide bond formation in peptides". Methods Enzymol. (1997); 289: 198-221.

Arber, Daniel A., et al., "The 2016 revision to the World Health Organization classification of myeloid neoplasms and acute leukemia", Blood, The Journal of the American Society of Hematology (May 19, 2016); 127(20): 2391-2405.

Ashby, et al., "Plasma hepcidin levels are elevated but responsive to erythropoietin therapy in renal disease." Kidney International (2009); 75 (9): 976-981.

[Author Unknown] "FDA Grants Orphan Drug Designation for Protagonist Therapeutics' PTG-300 for the Treatment of Beta-Thalassemia", Protagonist Therapeutics, Cision PR Newswire (Mar. 6, 2018); [Press release] http://www.prnewswire.com/news-releases/fda-grants-orphan-drug-designation-for-protagonist-therapeuticsptg-300-for-the-treatment-of-beta-thalassemia-300609386.html, 2 pages.

[Author Unknown] "Protagonist Announces Phase 1 and Preclinical Data on Hepcidin Mimetic PTG-300 Presented at European Hematology Association Annual Meeting", Protagonist Therapeutics, Cision PR Newswire (Jun. 18, 2018); [Press release] https://www.prnewswire.com/news-releases/protagonist-announces-phase-1-and-pre-clinical-data-on-hepcidin-mimetic-ptg-300-presented-at-european-hematology-association-annual-meeting-300667520.html, 2 pages.

[Author Unknown] "Protagonist Therapeutics Announces Fast Track Designation Granted by U.S. FDA to Hepcidin Mimetic PTG-300", Protagonist Therapeutics, Cision PR Newswire (Sep. 27, 2018); [Press release] https://www.prnewswire.com/news-releases/protagonist-therapeutics-announces-fast-track-designation-granted-by-US-fda-to-hepcidin-mimetic-ptg-300-300720035.html, 2 pages.

[Author Unknown] "Protagonist Therapeutics Expands Intellectual Property Portfolio", Protagonist Therapeutics, Cision PR Newswire (Sep. 6, 2018); [Press release] https://www.prnewswire.com/news-releases/protagonist-therapeutics-expands-intellectual-property-portfolio-300707765.html, 1 page.

[Author Unknown] "Protagonist Therapeutics Initiates Phase 2 Study of Novel Hepcidin Mimetic PTG-300 in the Treatment of Patients with Polycythemia Vera", Protagonist Therapeutics, Cision PR Newswire (Oct. 30, 2019); [Press release] https://www.prnewswire.com/news-releases/protagonist-therapeutics-initiates-phase-2-study-of-novel-hepcidin-mimetic-ptg-300-in-the-treatment-of-patients-with-polycythemia-vera-300948611.html, 2 pages.

[Author Unknown] "Protagonist Therapeutics Initiates Phase 2 Trial of Novel Hepcidin Mimetic PTG-300 for the Treatment of Patients with Beta Thalassemia", Protagonist Therapeutics, Cision PR Newswire (Jan. 9, 2019); [Press release] https://www.prnewswire.com/news-releases/protagonist-therapeutics-initiates-phase-2-trial-of-novel-hepcidin-mimetic-ptg-300-for-the-treatment-of-patients-with-beta-thalassemia-300775348.html, 2 pages.

[Author Unknown] "Protagonist Therapeutics Reports Second Quarter 2019 Financial Results", Protagonist Therapeutics, Cision PR Newswire (Aug. 7, 2019); [Press release] https://www.prnewswire.com/news-releases/protagonist-therapeutics-reports-second-quarter-2019-financial-results-300897892.html, 3 pages.

Balwani, Manisha, "Erythropoietic Protoporphyria and X-Linked Protoporphyria: pathophysiology, genetics, clinical manifestations, and management". Mol Genet Metab (Nov. 2019); 128(3): 298-303. Epub Jan. 24, 2019.

Barman-AksÖzen, et al., "Delta-aminolevulinic acid synthase 2 expression in combination with iron as modifiers of disease severity in erythropoietic protoporphyria". Molecular Genetics and Metabolism (Nov. 2019); 128(3): 304-308.

Boccia, Ralph V., et al., "Examining the frequency of phlebotomy in patients with polycythemia vera (PV) in the United States: an analysis of data from the Reveal study", Blood (Dec. 8, 2017); 130(1): 5271, 3 pages.

Boer, J., et al., "Design and Synthesis of Potent and Selective 47 Integrin Antagonists." J. Med. Chem. (2001); 44 (16): 2586-2592.

Bowie, J. U. et al., "Deciphering the message in protein sequences: Tolerance to amino acid substitutions," Science, (Mar. 16, 1990), 247(4948):1306-1310.

Brayden, D.J., and Mrsny, R.J., "Oral peptide delivery: prioritizing the leading technologies". Therapeutic Delivery (2011); 2(12): 1567-1573.

Burton, et al., "Systemic administration of a pharmacologic iron chelator reduces cartilage lesion development in the Dunkin-Hartley model of primary osteoarthritis". Free Radical Biology and Medicine (Feb. 1, 2022); 179: 47-58.

Carroll, et al., "Hereditary hemochromatosis is characterized by a clinically definable arthropathy that correlates with iron load". Arthritis & Rheumatism (Jan. 2011); 63(1): 286-294.

Casu, Carla, et al., "Minihepcidin peptides as disease modifiers in mice affected by β-thalassemia and polycythemia vera", Blood, The Journal of the American Society of Hematology (2016); 128(2): 265-276.

Casu, et al., "Hepcidin agonists as therapeutic tools". Blood, The Journal of the American Society of Hematology (Apr. 19, 2018); 131(16): 1790-1794.

Chang, et al., Role of disulfide bonds in the structure and activity of human insulin. Mol Cells (Dec. 2003); 16(3): 323-330.

Chatterjee, Jayanta, et al., "N-Methylation of Peptides: A New Perspective in Medicinal Chemistry", Accounts of Chemical Research (2008); 41(10): 1331-1342.

Chermahini et al., "Cyclic peptide nanocapsule as ion carrier for halides: a theoretical survey", Structural Chemistry (Oct. 2018); 29(5): 1351-1357.

Clark, et al., "The Engineering of an Orally Active Conotoxin for the Treatment of Neuropathic Pain." Angew Chem Int Ed (Sep. 2010); 49: 6545-6548.

Clark, et al., "Understanding the Structure/Activity Relationships of the Iron Regulatory Peptide Hepcidin." Chem Biol. (Mar. 2011); 18(3): 336-343.

Clark, Richard J., et al. "Design, synthesis, and characterization of cyclic analogues of the iron regulatory peptide hormone hepcidin." Peptide Science (2013); 100.5: 519-526.

Co-pending U.S. Appl. No. 18/284,835, inventors Bhandari; Ashok et al., filed on Sep. 28, 2023.

Co-pending U.S. Appl. No. 18/285,198, inventors Bourne; Gregory Thomas et al., filed on Sep. 29, 2023.

Co-pending U.S. Appl. No. 18/285,203, inventors Bourne; Gregory Thomas et al., filed on Sep. 29, 2023.

(56) References Cited

OTHER PUBLICATIONS

Co-pending U.S. Appl. No. 18/355,992, inventors Liu; David Y. et al., filed on Jul. 20, 2023.
Craik, et al., "Potential therapeutic applications of the cyclotides and related cystine knot mini-proteins." Expert Opin Investig Drugs (May 2007); 16(5): 595-604.
"Crushing Guide for Oral Medication in Residential Aged Care", Waitemata District Health Board, 2011, 2 pages.
Cui, et al., "Serum iron metabolism and erythropoiesis in patients with myelodysplastic syndrome not receiving RBC transfusions". Leuk Res. (2014); 38(5): 545-550.
Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from patent U.S. Pat. No. 8313950.", XP002761650, retrieved from EBI accession No. USPOP:AGA36544 Database accession No. AGA36544, 1 page.
Davies, U.S., "The Cyclization of Peptides and Depsipeptides", J Pept Sci. (Aug. 2003); 9(8): 471-501.
De Mast, et al., "Increased serum hepcidin and alterations in blood iron parameters associated with asymptomatic P. falciparum and P. vivax malaria." Haematologica (2010); 95 (7): 1068-1074.
De Vega, et al., "Modulation of Protein-Protein Interactions by Stabilizing/Mimicking Protein Secondary Structure Elements." Curr Top Med Chem (2007); 7(1): 33-62.
Definition of Isostere, Medical Definition and More from Merriam-Webster Dictionary, www.merriam-webster.com/medical/isostere accessed on Feb. 5, 2015, 3 pages.
Delgado et al., "The uses and properties of PEG-linked proteins". Critical Reviews in Therapeutic Drug Carrier Systems (Jan. 1, 1992); 9(3-4): 249-304.
Desbenoit, N., et al. "Reversible metalation of a bis-disulfide analogue of the Cys-X-Cys hepcidin binding site: structural characterisation of the related copper complex]." Annales Pharmaceutiques Francaises (2010); 68(6): 388-396. (with English summary).
Dolain, Christel, et al. "Inducing-Helices in Short Oligopeptides through Binding by an Artificial Hydrophobic Cavity." Journal of the American Chemical Society (2010); 132.16: 5564-5565.
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci. (2000); 6: 321-341.
Dutton, et al., "A New Level of Conotoxin Diversity, a Non-native Disulfide Bond Connectivity in-Conotoxin AuIB Reduces Structural Definition but Increases Biological Activity." J Biol Chem (Oct. 2002); 277(50): 48849-48857.
European Application No. 14763104.8, Extended European Search Report dated Sep. 23, 2016, 10 pages.
Extended European Search Report for European Application No. EP21199316.7 dated Oct. 24, 2022, 9 pages.
Fass, D., "Disulfide bonding in protein biophysics." Annu Rev Biophys (2012); 41: 63-79. Epub Dec. 20, 2011.
Fosgerau and Hoffman, "Peptide therapeutics: current status and future directions." Drug Discovery Today (2015); 20(1): 122-128.
Foster "Deuterium Isotope Effects in Studies of Drug Metabolism", Trends Pharmacol. Sci. (1984); 5(12): 524-527.
Francis, G., et al., "PEGylation of Cytokines and other Therapeutic Proteins and Peptides: the Importance of Biological Optimisation of Coupling Techniques," International Journal of Hematology, Jul. 1998, vol. 68, pp. 1-18, 19 pages.
Fruchtman, Steven M., et al., "From efficacy to safety: a Polycythemia Vera Study group report on hydroxyurea in patients with polycythemia vera", Seminars in hematology (1997); 34(1): 17-23.
Ganz and Nemeth, "Hepcidin and iron homeostasis." Biochimica et Biophysica Acta (BBA)—Molecular Cell Research (Sep. 2012); 1823 (9): 1434-1443.

Garcia, Josep et al., "D-Polyarginine Lipopeptides as Intestinal Permeation Enhancers". ChemMedChem Oct. 8, 2018; 13(19): 2045-2052. Epub Aug. 20, 2018.
Gee et al. "Cyclic Peptides as Non-carboxyl-terminal Ligands of Syntrophin PDZ Domains," The Journal of Biological Chemistry, 273(34): 21980-21987 (1998).
Gentilucci, et al., "Chemical Modifications Designed to Improve Peptide Stability: Incorporation of Non-Natural Amino Acids, Pseudo-Peptide Bonds, and Cyclization". Curr Pharm Des. (2010); 16(28): 3185-3203.
Girelli, Domenico, et al. "Hepcidin in the diagnosis of iron disorders." Blood (2016); 127.23: 2809-2813.
Gombotz and Pettit, "Biodegradable Polymers for Protein and Peptide Drug Delivery". Bioconjugate Chem. (Jul. 1, 1995); 6(4): 332-351.
Goptar, I.A., et al., "Properties of Post-Proline Cleaving Enzymes from Tenebrio Molitor," Russian Journal of Bioorganic Chemistry, 2008, vol. 34(3), pp. 280-285.
Görmer, et al., "Efficient Microwave-Assisted Synthesis of Unsymmetrical Disulfides", J. Org. Chem. (Feb. 1, 2010); 75(5): 1811-1813.
Gruschow, et al., "New pacidamycin antibiotics through precursor-directed biosynthesis". Chembiochem. Jan. 26, 2009; 10(2): 355-360.
Guerler and Knapp, "Novel protein folds and their nonsequential structural analogs." Protein Sci (Aug. 2008); 17(8): 1374-1382.
Guharoy and Chakrabarti, "Secondary structure based analysis and classification of biological interfaces: identification of binding motifs in protein-protein interactions." Bioinformatics (2007); 23(15): 1909-1918. Epub May 17, 2007.
Gupta, et al., "A classification of disulfide patterns and its relationship to protein structure and function." Protein Sci (Aug. 2004); 13(8): 2045-2058.
Hartig, et al., "Intramolecular disulphide bond arrangements in nonhomologous proteins." Protein Sci Publ Protein Soc (Feb. 2005); 14(2): 474-482.
Hawe, et al., "Forced degradation of therapeutic proteins." J Pharm Sci. (Mar. 2012); 101(3): 895-913. Epub Nov. 14, 2011.
Henikoff et al., "Amino acid substitution matrices from protein blocks," Proc. Natl. Acad. Sci. U.S.A., Nov. 1992, 89: 10915-10919.
Hruby and Bonner, "Design of Novel Synthetic Peptides Including Cyclic Conformationally and Topographically Constrained Analogs". Methods in Molecular Biology, Ch. 11, vol. 35 Peptide Synthesis Protocols, Edited by M.W Pennington and B. M. Dunn Copyright, 1994 Humana Press Inc, Totowa, NJ, pp. 201-241, 40 pages.
Hudecz, et al., "Synthesis, conformation, biodistribution and in vitro cytotoxicity of daunomycin-branched polypeptide conjugates". Bioconjugate Chem. (Jan. 1, 1992); 3(1): 49-57.
Ilyin, Gennady, et al. "Comparative analysis of mouse hepcidin 1 and 2 genes: evidence for different patterns of expression and inducibility during iron overload 1." FEBS Letters (2003); 542.1-3: 22-26.
Jagasia et al., " Peptide Cyclization and Cyclodimerization by Cu-Mediated Azide-Alkyne Cycloaddition", Journal of Organic Chemistry (Apr. 17, 2009); 74(8): 2964-2974.
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al., "Hepcidin revisited, disulfide connectivity, dynamics, and structure", Journal of Biological Chemistry (2009); 284(36): 24155-24167.
Karim, et al., "The role of disrupted iron homeostasis in the development and progression of arthropathy". Journal of Orthopaedic Research (Jun. 2022); 40(6): 1243-1250.
Kelleman, A. et al., "Incorporation of thioether building blocks into an v3-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.

(56) References Cited

OTHER PUBLICATIONS

Kluskens, L.D. et al., "Angiotensin-(1-7) with Thioether Bridge: An Angiotensin- Converting Enzyme-Resistant, Potent Angiotensin-(1-7) Analog", The Journal of Pharmacology and Experimental Therapeutics, 328(3): 849-855 (2009).

Knudsen, Lotte B., et al. "Potent derivatives of glucagon-like peptide-1 with pharmacokinetic properties suitable for once daily administration." Journal of Medicinal Chemistry (2000); 43.9: 1664-1669.

Kowdley, et al., "An-Open Label Phase 2, Dose-Finding Study of the Safety and Efficacy of Rusfertide (PTG-300), A Hepcidin Mimetic, In Patients with Hereditary Hemochromatosis". AASLD Abstract 649, AASLD Hepatology (2021); 74, No. 1(Suppl), p. 25A-25B, 2 pages.

Kowdley, et al., "Monitoring and Management of Nash is an Unmet Need Among Hepatologists and Endocrinologists: An International Mixed-Method Study in Europe and the USA". AASLD Abstract (Poster) 649, AASLD Hepatology (2021); 74, No. 1(Suppl), p. 394A, 1 page.

Krause, Alexander, et al. "LEAP 1, a novel highly disulfide bonded human peptide, exhibits antimicrobial activity." FEBS Letters (2000); 480.2-3: 147-150.

Kuchař, et al., "Human interleukin-23 receptor antagonists derived from an albumin-binding domain scaffold inhibit IL-23-dependent ex vivo expansion of IL-17-producing T-cells". Proteins (Jun. 2014); 82(6): 975-989. Epub Nov. 23, 2013.

Lecha, et al., "Erythropoietic protoporphyria". Orphanet Journal of Rare Diseases (2009); 4: 19, 10 pages.

Legge and Morieson, "On the prediction of partition coefficients and RF values of peptides." Aust. J. Biol. Sci. (1964); 17: 561-571.

Li and Roller, "Cyclization Strategies in Peptide Derived Drug Design." Curr. Topics Med. Chem. (2002); 2: 325-341.

List, A.F., "Iron overload in myelodysplastic syndromes: diagnosis and management". Cancer Control (Jan. 2010); 17(1_suppl):2-8, 7 pages.

Liu and Wang, "Endomorphins: potential roles and therapeutic indications in the development of opioid peptide analgesic drugs". Med Res Rev. (May 2012); 32(3): 536-580. Epub Feb. 1, 2011.

Liu, Shuang, "Radiolabeled Cyclic RGD Peptides as Integrin v3-Targeted Radiotracers: Maximizing Binding Affinity via Bivalency." Bioconjugate Chem. (2009); 20 (12): 2199-2213.

Liu, Shuang, "Radiolabeled Multimeric Cyclic Rgd Peptides as Integrin Alphavbeta3 Targeted Radiotracers For Tumor Imaging" School of Health Science, Purdue University, Molecular Pharmaceuticals (2006); 3(5):472-487.

Longobardo, et al., "β-Casomorphins: substitution of phenylalanine with β-homo-phenylalanine increases the μ-type opioid receptor affinity." Bioorganic & Medicinal Chemistry Letters (2000); 10(11): 1185-1188.

Longobardo, et al., "Incorporation of β-amino acids in bioactive peptides: a β-casomorphin case study." Peptides 2002, Abstract P A97, Proceedings of the European Peptide Symposium, 27th, Sorrento, Italy, Aug. 31-Sep. 6, 2002 (2002), 198-199.

Madsen, Kjeld, et al. "Structure-activity and protraction relationship of long-acting glucagon-like peptide-1 derivatives: importance of fatty acid length, polarity, and bulkiness." Journal of Medicinal Chemistry (2007); 50.24: 6126-6132.

Maeda, et al., "Conjugates of anticancer agents and polymers: advantages of macromolecular therapeutics in vivo". Bioconjugate Chem. (Sep./Oct. 1992); 3(5): 3511-362.

Maher, Sam et al., "Safety and efficacy of sodium caprate in promoting oral drug absorption: from in vitro to the clinic". Advanced Drug Delivery Reviews Dec. 17, 2009; 61 (15): 1427-1449. Epub Oct. 1, 2009.

Maher, Sam et al., "Application of Permeation Enhancers in Oral Delivery of Macromolecules: an Update". Pharmaceutics Jan. 19, 2019; 11 (1): 41, 23 pages.

Martinez, et al., "Hepatic damage and oxidative stress induced by griseofulvin in mice". Cellular and Molecular Biology (Jul. 1, 2009); 55(2): 127-139.

Muheem, Abdul et al., "A review on the strategies for oral delivery of proteins and peptides and their clinical perspectives". Saudi Pharmaceutical Journal Jul. 2016; 24(4):413-428. Epub Jun. 16, 2014.

Muñoz, Manuel, et al. "Disorders of iron metabolism. Part II: iron deficiency and iron overload." Journal of Clinical Pathology (2011); 64.4: 287-296.

Nemeth, Elizabeta, et al., "The N-terminus of hepcidin is essential for its interaction with ferroportin: structure-function study", Blood (2006); 107(1): 328-333.

Nguyen, et al., "Bone and joint complications in patients with hereditary hemochromatosis: a cross-sectional study of 93 patients". Therapeutic Advances in Musculoskeletal Disease (Jul. 2020); 12: 1759720X20939405, 14 pages. eCollection 2020.

Park, C.H., et al., "Hepcidin, a urinary antimicrobial peptide synthesized in the liver." J Biol Chem. (2001); 276(11): 7806-7810. Epub Dec. 11, 2000.

Parrow, et al., "Prospects for a hepcidin mimic to treat—thalassemia and hemochromatosis." Expert Review of Hematology (2011); 4 (3): 233-235.

Paterson, I.C., et al., "Partial Characterization of Specific Inducers of a Cuticle-Degrading Protease from the Insect Pathogenic Fungus Metarhizium Anisopliae," Microbiology, 1994, vol. 140(11), pp. 3153-3159.

Pattarawarapan, "Selective Formation of Homo- and Heterobivalent Peptidomimetics." J. Med. Chem. (Aug. 2003); 46 (17): 3565-3567.

PCT/US2014/030352, International Preliminary Report on Patentability, dated Sep. 15, 2015, 7 pages.

PCT/US2014/030352, International Search Report and Written Opinion, mailed Nov. 28, 2014, 12 pages.

PCT/US2014/030352, Invitation to Pay Additional Fees, mailed Sep. 10, 2014, 2 pages.

Pearson, T. C. and Wetherley-Mein, G., "Vascular occlusive episodes and venous haematocrit in primary proliferative polycythaemia", The Lancet (Dec. 9, 1978); 312(8102): 1219-1222.

Pelton, J.T et al., "Somatostatin Analogs with Affinity for Opiate Receptors in Rat Brain Binding Assay", Peptides, 6(Suppl 1): 159-163 (1985).

Pettit, L.D., et al., "Influence of the Proline Residue on the Co-Ordination of Cu(II) to Peptides Containing -Pro- and -Pro-Pro-Subunits," Polyhedron, 1987, vol. 6(1), pp. 45-52.

Preza, Gloria C., et al., "Minihepcidins are rationally designed small peptides that mimic hepcidin activity in mice and may be useful for the treatment of iron overload", The Journal of Clinical Investigation (2011); 121(12): 4880-4888.

Quiniou, et al., "Specific targeting of the IL-23 receptor, using a novel small peptide noncompetitive antagonist, decreases the inflammatory response". Am J Physiol Regul Integr Comp Physiol. (Nov. 15, 2014); 307(10): R1216-R1230. Epub Aug. 20, 2014.

Ramos, E., et al., "Minihepcidins prevent iron overload in a hepcidin-deficient mouse model of severe hemochromatosis." Blood (Nov. 2012); 120(18): 3829-3836. Epub Sep. 18, 2012.

Rampal, Raajit, et al., "Integrated genomic analysis illustrates the central role of JAK-STAT pathway activation in myeloproliferative neoplasm pathogenesis", e-Blood (May 29, 2014); 123(22): e123-33.

Rector Jr., William G., et al., "Non-hematologic effects of chronic iron deficiency: a study of patients with polycythemia vera treated solely with venesections", Medicine (Nov. 1982); 61(6): 382-389.

Rivera, Seth, et al., "Synthetic hepcidin causes rapid dose-dependent hypoferremia and is concentrated in ferroportin-containing organs", Blood (2005); 106: 2196-2199.

Rostovtsev, et al., "A Stepwise Huisgen Cycloaddition Process: Copper(I)Catalyzed Regioselective "Ligation" of Azides and Terminal Alkynes". Angewandte Chemie Int. Ed. (Jul. 2, 2002); 41(14): 2596-2599.

Rubinstein and Niv, "Peptidic modulators of protein-protein interactions: Progress and challenges in computational design." Biopolymers (2009); 91(7): 505-513.

Sasaki, et al., "D-Arg2-dermorphin tetrapeptide analogs: a potent and long-lasting analgesic activity after subcutaneous administration." Biochem Biophys Res Commun. (1984); 120 (1): 214-218.

(56) References Cited

OTHER PUBLICATIONS

Schmidt, et al., "Mild iron deficiency does not ameliorate the phenotype of a murine erythropoietic protoporphyria model". American Journal of Hematology (May 2020); 95(5): 492-496.
Sekeres and Cutler, "How we treat higher-risk myelodysplastic syndromes". Blood (Feb. 6, 2014); 123(6):829-836. Epub Dec. 20, 2013.
Shenoy, et al., "Impact of iron overload and potential benefit from iron chelation in low-risk myelodysplastic syndrome". Blood (Aug. 7, 2014); 124(6): 873-881. Epub Jun. 12, 2014.
Simmerling, et al., "Hydrophobic "Collapse" in a Cyclic Hexapeptide: Computer Simulations of CHDLFC and CAAAAC in Water" Journal of American Chemical Society (1994); 116(6): 2534-2547.
Speers, et al., "Activity-Based Protein Profiling in Vivo Using a Copper(I)-Catalyzed Azide-Alkyne [3 + 2] Cycloaddition". J. Am. Chem. Soc. (Mar. 28, 2003); 125(16): 4686-4687.
Stein, Brady L., et al., "Polycythemia vera: an appraisal of the biology and management 10 years after the discovery of JAK2 V617F", Journal of Clinical Oncology (Nov. 20, 2015); 33(33): 3953-60.
Streiff, Michael B., et al., "The diagnosis and management of polycythemia vera in the era since the Polycythemia Vera Study Group: a survey of American Society of Hematology members' practice patterns", Blood, The Journal of the American Society of Hematology (Feb. 15, 2002); 99(4): 1144-1149.
Tandara, Leida, and Salamunic, Ilza . "Iron metabolism: current facts and future directions." Biochemia Medica (2012); 22.3: 311-328.
Taranath, et al., "Regulation of Iron Homeostasis By PTG-300 Improves Disease Parameters in Mouse Models for Beta-Thalassemia and Hereditary Hemochromatosis". Blood (Nov. 13, 2019); 134 (Supplement_1): 3540, 3 pages.
Tefferi and Vardiman, "Myelodysplastic syndromes". N Engl J Med. (Nov. 5, 2009); 361(19): 1872-1885.
Tefferi, Ayalew and Barbui, Tiziano, "Polycythemia vera and essential thrombocythemia: 2017 update on diagnosis, risk-stratification, and management", American Journal of Hematology (Jan. 1, 2017); 92(1): 94-108.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Temraz, et al., "Iron overload and chelation therapy in myelodysplastic syndromes". Crit Rev Oncol Hematol. (Jul. 2014); 91(1): 64-73. Epub Jan. 24, 2014.
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
Tornøe, et al., "Peptidotriazoles on solid phase: [1,2,3]-triazoles by regiospecific copper(i)-catalyzed 1,3-dipolar cycloadditions of terminal alkynes to azides." J Org Chem. (May 3, 2002); 67(9): 3057-3064.
Tsukada, et al., "An Anti-α-Fetoprotein Antibody-Daunorubicin Conjugate With a Novel Poly-L-glutamic Acid Derivative as Intermediate Drug Carrier". J. Natl. Cancer Inst. (Sep. 1984); 73(3): 721-729.
Tuvia, et al., "A Novel Suspension Formulation Enhances Intestinal Absorption of Macromolecules via Transient and Reversible Transport Mechanisms". Pharm Res. (Feb. 21, 2014); 31(8): 2010-2021.
Wang, et al., "Bioconjugation by Copper(I)-Catalyzed Azide-Alkyne [3 + 2] Cycloaddition". J Am Chem Soc. (Mar. 19, 2003); 125(11): 3192-3193.
Whalen, et al., "Association of transferrin saturation with the arthropathy of hereditary hemochromatosis". Clinical Gastroenterology and Hepatology (Oct. 1, 2017); 15(10): 1507-1508.

White and Yudin, "Contemporary strategies for peptide macrocyclization." Nat Chem (Jun. 2011); 3(7): 509-524.
Witt, Dariusz, "Recent developments in disulfide bond formation". Synthesis (2008); 16: 2491-2509.
Wulf, et al., "Inactivation of protoporphyrin IX in erythrocytes in patients with erythropoietic protoporphyria: A new treatment modality". Photodiagnosis and Photodynamic Therapy (Mar. 1, 2020); 29: 101582, 4 pages.
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yampolsky and Stoltzfus, "The Exchangeability of Amino Acids in Proteins", Genetics (Aug. 2005); 170(4): 1459-1472. Epub Jun. 8, 2005.
Yoshida, et al., "Erythropoietic protoporphyria-related hepatopathy successfully treated with phlebotomy". Internal Medicine (Sep. 1, 2018); 57(17): 2505-2509.
Zalipsky, Samuel, "Functionalized Poly(ethylene glycols) for Preparation of Biologically Relevant Conjugates". Bioconjugate Chem. (1995); 6(2): 150-165.
[No Author Listed], Fast Track. U.S. Food and Drug Administration. Jan. 4, 2018, available online at: https://www.fda.gov/patients/fast-track-breakthrough-therapy-accelerated-approval-priority-review/fast-track. 2 pages.
[No Author Listed], Glu—His—Phe—Ala—Tyr—Gly—Phe—Arg—Pro—NHEt. Pubchem SID 376236348. Modify Date: Nov. 16, 2018. Retrieved from the Internet URL: https://pubchem.ncbi.nlm.nih.gov/substance/376236348. 3 pages.
[No Author Listed], Polycythemia Vera. National Organization for Rare Disorders NORD. Nov. 16, 2023, available online at: https://rarediseases.org/rare-diseases/polycythemia-vera/. 4 pages.
[No Author Listed], PubChem SID 96075894. Modify Date: Jul. 6, 2010. Retrieved from the Internet URL: https://pubchem.ncbi.nlm.nih.gov/substance/96075894. 3 pages.
Gerds et al., Rusfertide for Polycythemia Vera: Similar Dosing in Patients Receiving Therapeutic Phlebotomy Alone or in Combination with Cytoreductive Treatment. Blood. 2022;140(Supplement 1):12241-12243. doi.org/10.1182/blood-2022-163847. Abstract only. 4 pages.
Kremyanskaya et al., Rusfertide, a Hepcidin Mimetic, for Control of Erythrocytosis in Polycythemia Vera. N Engl J Med. Feb. 22, 2024;390(8):723-735. doi: 10.1056/NEJMoa2308809.
Mount Sinai Health System, Novel treatment for polycythemia vera shows promise in clinical trial. News-Medical.Net, Available online at: https://www.news-medical.net/news/20240221/Novel-treatment-for-polycythemia-vera-shows-promise-in-clinical-trial.aspx. Feb. 21, 2024. 3 pages.
Protagonist Therapeutics, Inc., Protagonist Therapeutics Receives FDA Breakthrough Therapy Designation for Rusfertide in Polycythemia Vera. PR Newswire. Jun. 3, 2021, available online at: https://www.prnewswire.com/news-releases/protagonist-therapeutics-receives-fda-breakthrough-therapy-designation-for-rusfertide-in-polycythemia-vera-301304760.html. 3 pages.
Shames et al., Hepcidin Mimetic PTG-300 Induces Dose-Related and Sustained Reductions in Serum Iron and Transferrin Saturation in Healthy Subjects. EHA Library. Jun. 16, 2018;214566;S895. Abstract only. Abstract release date: May 17, 2018. Available online at: https://library.ehaweb.org/eha/2018/stockholm/214566/richard.shames.hepcidin.mimetic.ptg-300.induces.dose-related.and.sustained.html?f=menu=14media=3speaker=663819. 1 page.
Taranath et al., Mechanism of Systemic Iron Regulation and Hematocrit Control By Hepcidin Peptidomimetics in Pre-Clinical Models. Blood. 2020;136(Supplement 1):49. doi.org/10.1182/blood-2020-141670. Abstract only. 4 pages.
Triguero et al., Low-risk polycythemia vera treated with phlebotomies: clinical characteristics, hematologic control and complications in 453 patients from the Spanish Registry of Polycythemia Vera. Ann Hematol. Oct. 2022;101(10):2231-2239. doi: 10.1007/s00277-022-04963-z. Epub Aug. 30, 2022. Erratum in: Ann Hematol. Dec. 2022;101(12):2819-2820. doi: 10.1007/s00277-022-05005-4.

HEPCIDIN ANALOGUES AND USES THEREOF

CROSS REFERENCE TO RELATED APPLICATIONS

This application is a Continuation of U.S. application Ser. No. 17/099,308, filed Nov. 16, 2020; which is a Continuation of U.S. application Ser. No. 16/839,368, filed Apr. 3, 2020, now abandoned; which is a Continuation of U.S. application Ser. No. 16/553,486, filed Aug. 28, 2019, now abandoned; which is a Continuation of U.S. application Ser. No. 16/289,451, filed Feb. 28, 2019, now U.S. Pat. No. 10,501,515, issued Dec. 10, 2019; which is a Continuation of U.S. application Ser. No. 16/037,982, filed Jul. 17, 2018, now U.S. Pat. No. 10,442,846, issued Oct. 15, 2019; which is a Continuation of U.S. application Ser. No. 15/828,214, filed Nov. 30, 2017, now U.S. Pat. No. 10,030,061, issued Jul. 24, 2018; which is a Continuation of U.S. application Ser. No. 15/720,333, filed Sep. 29, 2017, now abandoned; which is a Continuation of U.S. application Ser. No. 14/775,469, filed Sep. 11, 2015, now U.S. Pat. No. 9,822,157, issued Nov. 21, 2017; which is a U.S. National Phase Application of International Patent Application No. PCT/US2014/030352, filed Mar. 17, 2014, which claims the benefit under 35 U.S.C. § 119(e) of U.S. Provisional Application No. 61/800,048, filed on Mar. 15, 2013, and U.S. Provisional Application No. 61/800,284, filed on Mar. 15, 2013, each of which is incorporated by reference herein in its entirety.

STATEMENT REGARDING SEQUENCE LISTING

The Sequence Listing XML associated with this application is provided in XML file format and is hereby incorporated by reference into the specification. The name of the XML file containing the Sequence Listing XML is PRTH_001_09US_ST26.xml. The XML file is 485,338 bytes, and created on Sep. 28, 2023, and is being submitted electronically via USPTO Patent Center.

FIELD OF THE INVENTION

The present invention relates, inter alia, to certain hepcidin peptide analogues, including peptides and dimers thereof, as well as compositions comprising the peptides and peptide dimers, and to the use of the peptides and peptide dimers in the treatment and/or prevention of a variety of diseases, conditions or disorders, including treatment and/or prevention of iron overload diseases including hereditary hemochromatosis, iron-loading anemias, and other conditions and disorders described herein.

BACKGROUND

Hepcidin (also referred to as LEAP-1), a peptide hormone produced by the liver, is a regulator of iron homeostasis in humans and other mammals. Hepcidin acts by binding to its receptor, the iron export channel ferroportin, causing its internalization and degradation. Human hepcidin is a 25-amino acid peptide (Hep25). See Krause et al. (2000) FEBS Lett 480:147-150, and Park et al. (2001) J Biol Chem 276:7806-7810. The structure of the bioactive 25-amino acid form of hepcidin is a simple hairpin with 8 cysteines that form 4 disulfide bonds as described by Jordan et al. J Biol Chem 284:24155-67. The N terminal region is required for iron-regulatory function, and deletion of 5 N-terminal amino acid residues results in a loss of iron-regulatory function. See Nemeth et al. (2006) Blood 107:328-33.

Abnormal hepcidin activity is associated with iron overload diseases, including hereditary hemochromatosis (HH) and iron-loading anemias. Hereditary hemochromatosis is a genetic iron overload disease that is mainly caused by hepcidin deficiency, or in some cases by hepcidin resistance. This allows excessive absorption of iron from the diet and development of iron overload. Clinical manifestations of HH may include liver disease (e.g., hepatic cirrhosis and hepatocellular carcinoma), diabetes, and heart failure. Currently, the only treatment for HH is regular phlebotomy, which is very burdensome for the patients. Iron-loading anemias are hereditary anemias with ineffective erythropoiesis such as β-thalassemia, which are accompanied by severe iron overload. Complications from iron overload are the main cause of morbidity and mortality for these patients. Hepcidin deficiency is the main cause of iron overload in non-transfused patients, and contributes to iron overload in transfused patients. The current treatment for iron overload in these patients is iron chelation which is very burdensome, sometimes ineffective, and accompanied by frequent side effects.

Hepcidin has a number of limitations which restrict its use as a drug, including a difficult synthesis process due in part to aggregation and precipitation of the protein during folding, which in turn leads to high cost of goods. What are needed in the art are compounds having hepcidin activity and also possessing other beneficial physical properties such as improved solubility, stability, and/or potency, so that hepcidin-like biologics might be produced affordably, and used to treat hepcidin-related diseases and disorders such as, e.g., those described herein.

The present invention addresses such needs, providing novel peptide analogues, and dimers thereof, having hepcidin activity and also having other beneficial properties making the peptides of the present invention suitable alternatives to hepcidin.

BRIEF SUMMARY OF THE INVENTION

The present invention generally relates to peptides exhibiting hepcidin activity and methods of using the same.

In some embodiments, the invention provides peptides, which may be isolated and/or purified, comprising, consisting essentially of, or consisting of, the following structural formula $$R^1\text{-}X\text{-}Y\text{-}R^2 \quad \text{(I)} \quad \text{(SEQ ID NO: 12)}$$

or a pharmaceutically acceptable salt or solvate thereof, wherein $R^1$ is hydrogen, an C1-C6 alkyl, C6-C12 aryl, C6-C12 aryl C1-C6 alkyl, C1-C20 alkanoyl (e.g. methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g. PEG3 to PEG11), alone or as spacers of any of the foregoing;

$R^2$ is —$NH_2$ or —OH;

X is a peptide sequence having the formula (Ia)

(Ia)
(SEQ ID NO: 1)
X1-X2-X3-X4-X5-X6-X7-X8-X9-X10 wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, bhPhe, of D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
Y is absent or Y is a peptide having the formula (IIa)

(IIa)
(SEQ ID NO: 5)
Y1-Y2-Y3-Y4-Y5-Y6-Y7-Y8-Y9-Y10-Y11-Y12-Y13-Y14-Y15 wherein
Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Arg, Ala, Pro, Val or absent;
Y7 is Trp, Lys, Gly, Ala Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein if Y is absent from the peptide of formula (I), X7 is Ile; and
wherein said compound of formula (I) is optionally PEGylated on $R^1$, X, or Y.

In some embodiments, the compound of formula (I) comprises two or more cysteine residues, wherein at least two of said cysteine residues are linked via a disulfide bond.

In some embodiments, the invention provides peptides, which may be isolated and/or purified, comprising, consisting essentially of, or consisting of the following structural formula (I')
(SEQ ID NO: 21)
$R^{1'}$-X'-Y'-$R^{2'}$ or a pharmaceutically acceptable salt or solvate thereof, wherein
$R^{1'}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g. methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g. PEG3 to PEG11), alone or as spacers of any of the foregoing;
$R^{2'}$ is —$NH_2$ or —OH;
X' is a peptide sequence having the formula Ia'

(Ia')
(SEQ ID NO: 13)
X1-X2-X3-X4-X5-X6-X7-X8-X9-X10 wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Ala, D-His or Lys;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
and provided that if Y' is absent, X7 is Ile;
Y' is a peptide having the formula IIa'

(IIa')
(SEQ ID NO: 16)
Y1-Y2-Y3-Y4-Y5-Y6-Y7-Y8-Y9-Y10-Y11-Y12-Y13-Y14-Y15 wherein
Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Ala, Pro, Val or absent;
Y7 is Trp, Lys, Gly, Ala, Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein said compound of formula I' is optionally PEGylated on $R^{1'}$, X', or Y'; and
wherein when said compound of formula I' comprises two or more cysteine residues, at least two of said cysteine residues being linked via a disulfide bond.

In some embodiments, the compound of formula I' comprises an $R^{1'}$ moiety that is hydrogen, isovaleric acid, isobutyric acid, or acetyl.

In some embodiments, the compound of formula I' comprises an X' peptide of formula Ia' as described herein, wherein
X1 is Asp, Ala, Ida, pGlu, bhAsp, Leu, D-Asp or absent;
X2 is Thr, Ala, or D-Thr;
X3 is His, Lys, D-His or Lys;

X4 is Phe, Ala, Dpa or D-Phe;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.

In some embodiments, the compound of formula I' comprises an X' peptide of formula Ib':

X1-Thr-His-X4-X5-X6-X7-X8-Phe-X10 (Ib')

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile Lys, Glu, Phe, Gln or Arg; and
X10 is Lys or absent.

In some embodiments, the compound of formula I' comprises an X' peptide of formula Ic':

X1-Thr-His-X4-X5-Cys-Ile-X8-Phe-X10 (Ic')

wherein
X1 is Asp, Ida, pGlu, bhAsp or absent;
X4 is Phe or Dpa;
X5 is Pro or bhPro;
X8 is Ile Lys, Glu, Phe, Gln or Arg; and
X10 is Lys or absent.

In some embodiments, the compound of formula I' comprises a Y' peptide of formula IIb'.

Y1-Y2-Y3-Y4-Y5-Y6-Y7-Y8-Cys-Y10 (IIb')

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp or Ala;
Y8 is Val, Thr, Ala or Glu; and
Y10 is Met, Lys or absent.

In some embodiments, the compound of formula I' comprises a Y' peptide of formula IIc'.

Y1-Y2-Y3-Ser-Lys-Gly-Trp-Y8-Cys-Y10 (IIc')

wherein
Y1 is Gly, Pro or D-Pro;
Y2 is Pro or Gly;
Y3 is Arg or Lys;
Y8 is Val or Thr; and
Y10 is Met, Lys or absent.

In some embodiments, the compound of formula I' comprises a Y' peptide of formula IId':

Cys-Y3-Y4-Arg-Y6-Y7-Y8-Cys-Y10-Y11-Y12-Y13-Y14-Y15 (IId')

wherein
Y1 is Val or Ala or absent;
Y3 is Gly, Pro or absent;
Y4 is His, Trp or Tyr; Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

In some embodiments, the compound of formula I' comprises a Y' peptide of formula IIe':

Val-Cys-Y3-His-Arg-Y6-Y7-Y8-Cys-Tyr-Arg-Y12-Y13-Y14-Y15 (IIe')

wherein
Y3 is Gly or absent;
Y6 is Ser or Pro;
Y7 is Ile or Lys;
Y8 is Gly or absent;
Y12 is Arg or Ala;
Y13 is Cys or Val or absent;
Y14 is Cys, Arg, Thr or absent; and
Y15 is Arg or absent.

In some embodiments, the invention provides peptides, which may be isolated and/or purified, comprising, consisting essentially of, or consisting of the following structural formula (I'')
(SEQ ID NO: 27)
R$^{1''}$-X''-Y''-R$^{2''}$ or a pharmaceutically acceptable salt or solvate thereof, wherein
R$^{1''}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g. methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g. PEG3 to PEG11), alone or as spacers of any of the foregoing;
R$^{2''}$ is —NH$_2$ or —OH;
X'' is a peptide sequence having the formula Ia''

(Ia'')
(SEQ ID NO: 22)
X1-X2-X3-X4-X5-X6-X7-X8-X9-X10 wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Ala, D-His or Lys;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
and provided that if Y'' is absent, X7 is Ile.

In some embodiments, the compound of formula I'' is PEGylated on R$^{1''}$, X'', or Y''.

In some embodiments, the compound of formula I'' comprises two or more cysteine residues, at least two of said cysteine residues being linked via a disulfide bond.

In some embodiments, the compound of formula I'' comprises an R$^{1''}$ that is hydrogen, isovaleric acid, iso-butyric acid or acetyl.

In some embodiments, the compound of formula I″ comprises an X″ peptide according to formula Ia″, disclosed herein, wherein X1 is Asp, Ala, Ida, pGlu, bhAsp, Leu, D-Asp or absent;
X2 is Thr, Ala, or D-Thr;
X3 is His, Lys, D-His or Lys;
X4 is Phe, Ala, or Dpa;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys or absent.

In some embodiments, the compound of formula I″ comprises an X″ peptide of formula Ib″:

X1-Thr-His-X4-X5-X6-X7-X8-Phe-X10    (Ib″)

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys, Phe or absent.

In some embodiments, the compound of formula I″ comprises an X″ peptide of formula Ic″:

X1-Thr-His-X4-X5-Cys-Ile-X8-Phe-X10    (Ic″)

wherein
X1 is Asp, Ida, pGlu, bhAsp or absent;
X4 is Phe or Dpa;
X5 is Pro or bhPro;
X8 is Ile, Lys, Glu, Phe, Gln or Arg; and
X10 is Lys or absent.

In some embodiments, the compound of formula I″ comprises a Y″ peptide of formula IIa″:

(IIa″)
(SEQ ID NO: 25)
Y1-Y2-Y3-Y4-Y5-Y6-Y7-Y8-Cys-Y10 wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp, Ala or absent;
Y8 is Val, Thr, Lys, Ala, Glu or absent; and
Y10 is Met, Lys or absent.

In some embodiments, the compound of formula I″ comprises a Y″ peptide of formula IIb″:

Y1-Y2-Y3-Ser-Lys-Gly-Trp-Y8-Cys-Y10    (IIb″)

wherein
Y1 is Gly, Pro or D-Pro;
Y2 is Pro, Gly;
Y3 is Arg, Lys;
Y8 is Val or Thr; and
Y10 is Met, Lys or absent.

In related embodiments, the present invention includes dimers, e.g., homodimers, of any of the peptides of the present invention.

In some embodiments, the peptides or dimers of the present invention exhibit hepcidin activity. In some embodiments, the peptides or dimers bind ferroportin, e.g., human ferroportin.

In some embodiments, the present invention provides methods of binding a ferroportin or inducing ferroportin internalization and degradation which comprise contacting the ferroportin with at least one peptide, dimer or composition as disclosed herein.

In some embodiments, the present invention provides compositions and medicaments comprising at least one peptide or dimer as disclosed herein.

In some embodiments, the present invention provides a method of manufacturing medicaments comprising at least one peptide or dimer as disclosed herein for the treatment of diseases of iron metabolism, such as iron overload diseases.

Also provided are methods of treating a disease of iron metabolism in a subject, such as a mammalian subject, e.g., a human subject, comprising administering at least one peptide, dimer or composition as disclosed herein to the subject. In some embodiments, the peptide or dimer is administered in a therapeutically effective amount. In some embodiments, the disease of iron metabolism is an iron overload disease.

In some embodiments, the present invention provides a method of manufacturing a peptide or peptide dimer of the present invention synthetically. In some embodiments, the present invention provides a method of manufacturing a peptide or peptide dimer of the present invention recombinantly.

In some embodiments, the present invention provides a pharmaceutical composition comprising a peptide analogue (e.g., a peptide or dimer of the present invention), or pharmaceutically acceptable salt or solvate thereof, as described herein, in combination with one or more peptide analogue (e.g., a peptide or dimer of the present invention) or pharmaceutically acceptable salt or solvate thereof, as described herein together with a pharmaceutically acceptable carrier, excipient or vehicle.

In some embodiments, the invention provides a process for manufacturing a compound or a pharmaceutical composition as disclosed herein.

In some embodiments, the invention provides a device comprising at least one peptide analogue (e.g., a peptide or dimer of the present invention), or pharmaceutically acceptable salt or solvate thereof for delivery of the peptide analogue to a subject.

In some embodiments, the present invention provides kits comprising at least one peptide, dimer, or composition as disclosed herein packaged together with a reagent, a device, instructional material, or a combination thereof.

In some embodiments, the present invention provides complexes which comprise at least one peptide or dimer as disclosed herein bound to a ferroportin, e.g., a human ferroportin, or an antibody, such as an antibody which specifically binds a peptide as disclosed herein, Hep25, or a combination thereof.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE INVENTION

Figure 1:
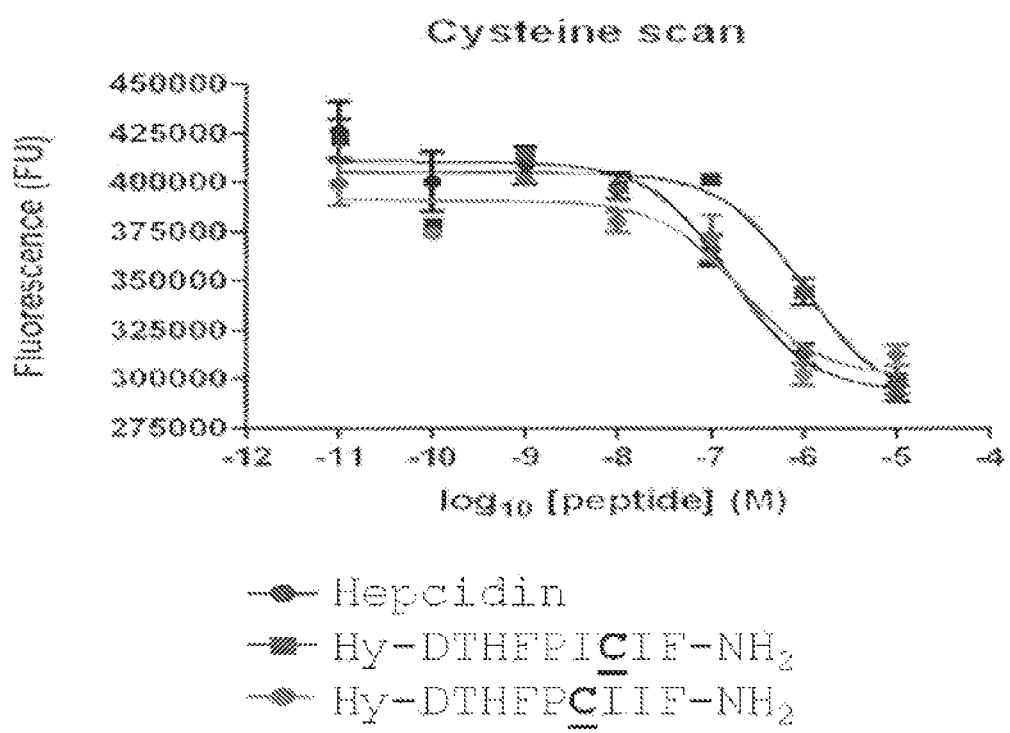
FIG. 1 shows the results of an in vitro activity assay measuring the induction of degradation of the human ferroportin protein. Presented are dose response curves for Compound No. 1 as compared to Hepcidin and the Mini-Hepcidin control.

Unless otherwise defined herein, scientific and technical terms used in this application shall have the meanings that are commonly understood by those of ordinary skill in the art.

Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

All publications, patents and published patent applications referred to in this application are specifically incorporated by reference herein. In case of conflict, the present specification, including its specific definitions, will control.

Each embodiment of the invention described herein may be taken alone or in combination with one or more other embodiments of the invention.

Definitions

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term formula (I), is used herein interchangeably with the term formula I (i.e., without the parentheses). The term formula (I'), is used herein interchangeably with the term formula I' (i.e., without the parentheses). The term formula (I"), is used herein interchangeably with the term formula I" (i.e., without the parentheses).

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

As used herein, the term "pharmaceutically acceptable salt" is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see Handbook of Pharmaceutical Salts: Properties, Selection, and Use by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

The term "solvate" in the context of the present invention refers to a complex of defined stoichiometry formed between a solute (in casu, a peptide analogue or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that causes internalization of the ferroportin protein.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease.

In some embodiments, the disease and disorders are related to iron overload diseases such as iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia.

In some embodiments, the peptides of the invention are used to treat diseases and disorders that are not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, peptides of the invention may be used to treat these diseases and conditions. Those skilled in the art are readily able to determine whether a given disease can be treated with a peptide according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In certain embodiments of the present invention, the diseases of iron metabolism are iron overload diseases, which include hereditary hemochromatosis, iron-loading anemias, alcoholic liver diseases and chronic hepatitis C.

As used herein, the terms "protein", "polypeptide" and "peptide" are used interchangeably to refer to two or more amino acids linked together. Except where indicated otherwise, e.g., for the abbreviations for the uncommon or unnatural amino acids set forth herein, the three-letter and one-letter abbreviations, as used in the art, are used herein to represent amino acid residues. Except when preceded with "D-", the amino acid is an L-amino acid. Groups or strings of amino acid abbreviations are used to represent peptides. Except when specifically indicated, peptides are indicated with the N-terminus on the left and the sequence is written from the N-terminus to the C-terminus.

The term "peptide analogue" in the context of the present invention refers to a molecule in which a first peptide moiety is attached (i.e. coupled or linked), either directly or via a linking (i.e. bridging or spacing) chemical moiety, to a second peptide moiety, by means of covalent chemical bonding. In certain embodiments, a peptide analogue is a peptide described herein comprising an X peptide sequence and a Y peptide sequence. In certain embodiments, a peptide analogue is a peptide described herein comprising an X' peptide sequence and a Y' peptide sequence. In certain embodiments, a peptide analogue is a peptide described herein comprising an X" peptide sequence and a Y" peptide sequence. In certain embodiments, a peptide analogue is a peptide described herein comprising an X peptide sequence and/or a Y peptide sequence conjugated to an additional chemical moiety. In certain embodiments, a peptide analogue is a peptide described herein comprising an X' peptide sequence and/or a Y' peptide sequence conjugated to an additional chemical moiety. In certain embodiments, a peptide analogue is a peptide described herein comprising an X" peptide sequence and/or a Y" peptide sequence conjugated to an additional chemical moiety. The peptides of the present invention described herein are peptide analogues. Peptide analogues also include any of the peptide dimers described herein.

Peptides and peptide dimers of the present invention may also be referred to herein as compounds or peptide analogues.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. Another example of a conservative substitution with a residue normally not found in endogenous, mammalian peptides and proteins is the conservative substitution of Arg or Lys with, for example, ornithine, canavanine, aminoethylcysteine or another basic amino acid. In some embodiments, one or more cysteines of a peptide analogue of the invention may be substituted with another residue, such as a serine. For further information concerning phenotypically silent substitutions in peptides and proteins, see, for example, Bowie et. al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N | H | M | F |
| S | D | R | L | Y |
| T | E | K | I | W |
| P | Q |   | V |   |
| G |   |   | C |   |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|----|-----|------|----|---|
| A | E | H | M | F |
| L | D | R | S | Y |
| I |   | K | T | W |
| P |   |   | C |   |
| G |   |   | N |   |
| V |   |   | Q |   |

In certain embodiments, the present invention provides peptides which are useful in the study and treatment of diseases of iron metabolism.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of less common or non-naturally occurring amino acids, unless they are referred to by their full name (e.g. sarcosine, ornithine, etc.), frequently employed three- or four-character codes are employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (γ-glutamic acid), Gaba (γ-aminobutanoic acid), 3-Pro (pyrrolidine-3-carboxylic acid), and 8Ado (8-amino-3,6-dioxaoctanoic acid), Abu (4-amino butyric acid), bhPro (β-homoproline), bhPhe (β-homophenylalanine) and Dpa (β,β diphenylalanine), and Ida (Iminodiacetic acid).

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom [e.g., $R^1$, $R^{1\prime}$, or $R^{1\prime\prime}$=hydrogen (Hy-) in formula I, I', or I", respectively, corresponding to the presence of a free primary or secondary amino group at the N-terminus], while an "—OH" or an "—NH$_2$" moiety at the C-terminus of the sequence indicates a hydroxy group [e.g., $R^2$, $R^{2\prime}$, or $R^{2\prime\prime}$=OH in formula I, I', or I", respectively, corresponding to the presence of a carboxy (COOH) group at the C-terminus] or an amino group [e.g., $R^2$, $R^{2\prime}$, or $R^{2\prime\prime}$=NH$_2$ in formula I, I', or I", respectively, corresponding to the presence of an amido (CONH$_2$) group at the C-terminus], respectively. In each sequence of the invention, a C-terminal "—OH" moiety may be substituted for a C-terminal "—NH$_2$" moiety, and vice-versa. Furthermore, $R^1$, $R^{1\prime}$, or $R^{1\prime\prime}$ can in all sequences be substituted with isovaleric acids or equivalent. In some embodiments, wherein a peptide of the present invention is conjugated to an acidic compound such as, e.g., isovaleric acid, isobutyric acid, valeric acid, and the like, the presence of such a conjugation is referenced in the acid form. So, for example, but not to be limited in any way, instead of indicating a conjugation of isovaleric acid to a peptide DTHFPCIKFCK (SEQ ID NO:215) by referencing isovaleroyl (e.g., isovaleroyl-DTHFPCIKFCK [SEQ ID NO:215]), in some embodiments, the present application references such a conjugation as isovaleric acid-DTHFPCIKFCK (SEQ ID NO:215). Unless otherwise indicated, reference is made to the L-isomeric forms of the amino acids in question.

Where appropriate, the D-isomeric form of an amino acid is indicated in the conventional manner by the prefix "D" before the conventional three-letter code (e.g., DAsp or D-Asp; DPhe or D-Phe).

In some embodiments, the invention provides peptides, which may be isolated and/or purified, comprising, consisting essentially of, or consisting of, the following structural formula:

(I)

$R^1$-X-Y-$R^2$ (SEQ ID NO: 12)

or a pharmaceutically acceptable salt or solvate thereof, wherein
$R^1$ is hydrogen, an C1-C6 alkyl, C6-C12 aryl, C6-C12 aryl C1-C6 alkyl, C1-C20 alkanoyl (e.g., methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g., PEG3 to PEG11), alone or as spacers of any of the foregoing;
$R^2$ is —NH$_2$ or —OH;

X is a peptide sequence having the formula (Ia)

(Ia)
(SEQ ID NO: 1)
X1-X2-X3-X4-X5-X6-X7-X8-X9-X10 wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, bhPhe, or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
Y is absent or Y is a peptide having the formula (IIa)

(IIa)
(SEQ ID NO: 5)
Y1-Y2-Y3-Y4-Y5-Y6-Y7-Y8-Y9-Y10-Y11-Y12-Y13-Y14-Y15 wherein
Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Arg, Ala, Pro, Val or absent;
Y7 is Trp, Lys, Gly, Ala Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein if Y is absent from the peptide of formula (I), X7 is Ile; and
wherein said compound of formula (I) is optionally PEGylated on $R^1$, X, or Y.

In some embodiments, the compound or peptide of formula (I) comprises two or more cysteine residues, wherein at least two of said cysteine residues are linked via a disulfide bond.

In some embodiments, X is a peptide sequence according to formula (Ia), described herein,
wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, or bhPhe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;

X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent.
In some embodiments, X is a peptide sequence according to formula (Ia), described herein, wherein
X1 is Asp, Ala, Ida, pGlu, bhAsp, Leu, D-Asp or absent;
X2 is Thr, Ala, or D-Thr;
X3 is His, Lys, or D-His;
X4 is Phe, Ala, or Dpa;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.
In some embodiments, X is a peptide sequence having the formula (Ib)

```
                                    (SEQ ID NO: 2)
(Ib)
X1-Thr-His-X4-X5-X6-X7-X8-Phe-X10
``` wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys, Phe or absent;
In some embodiments, X is a peptide sequence according to formula (Ib), as described herein, wherein
X1 is Asp, Glu, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys or absent.
In some embodiments, X is a peptide sequence having the formula (Ic)

```
                                    (SEQ ID NO: 3)
(Ic)
X1-Thr-His-X4-X5-Cys-Ile-X8-Phe-X10
``` wherein
X1 is Asp, Glu, Ida, pGlu, bhAsp or absent;
X4 is: Phe or Dpa;
X5 is Pro or bhPro;
X8 is Ile Lys, Glu, Phe, Gln or Arg; and
X10 is Lys or absent.
In some embodiments, X is a peptide sequence having the formula (Id)

```
                                    (SEQ ID NO: 4)
(Id)
X1-Thr-His-Phe-X5-Cys-Ile-X8-Phe-X10
``` wherein
X1 is Asp, Glu, or Ida;
X4 is: Phe;
X5 is Pro or bhPro;
X8 is Ile, Lys or Phe; and
X10 is absent.

In some embodiments, Y is a peptide sequence having the formula IIb

```
(IIb)
                                    (SEQ ID NO: 6)
Y1-Y2-Y3-Y4-Y5-Y6-Y7-Y8-Cys-Y10
``` wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp, Ala or absent;
Y8 is Val, Thr, Lys, Ala, Glu or absent; and
Y10 is Met, Lys or absent.
In some embodiments, Y is a peptide sequence according to formula (IIb), as described herein,
wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp or Ala;
Y8 is Val, Thr, Ala, or Glu; and
Y10 is Met, Lys or absent.
In some embodiments, Y is a peptide sequence having the formula (IIc)

```
(IIc)
                                    (SEQ ID NO: 7)
Y1-Y2-Y3-Ser-Lys-Gly-Trp-Y8-Cys-Y10
``` wherein
Y1 is Gly, Pro or D-Pro;
Y2 is Pro or Gly;
Y3 is Arg or Lys;
Y8 is Val or Thr; and
Y10 is Met, Lys or absent.
In some embodiments, Y is a peptide sequence having the formula (IId)

```
(IId)
                                    (SEQ ID NO: 8)
Y1-Cys-Y3-Y4-Arg-Y6-Y7-Y8-Cys-Y10-Y11-Y12-Y13-Y14-
Y15
``` wherein
Y1 is Val, Ala or absent;
Y3 is Gly, Pro or absent;
Y4 is His, Trp or Tyr;
Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

In some embodiments, Y is a peptide sequence having the formula (IIe)

(IIe)
(SEQ ID NO: 9)
Val-Cys-Y3-His-Arg-Y6-Y7-Y8-Cys-Tyr-Arg-Y12-Y13-
Y14-Y15 wherein
Y3 is Gly or absent;
Y6 is Ser or Pro;
Y7 is Ile or Lys;
Y8 is Gly or absent;
Y12 is Arg or Ala;
Y13 is Cys, Val or absent;
Y14 is Cys, Arg, Thr or absent; and
Y15 is Arg or absent.

In some embodiments, Y is a peptide sequence having the formula (IIf)

(IIf)
(SEQ ID NO: 10)
Y1-Pro-Y3-Ser-Y5-Y6-Y7-Y8-Cys-Y10 wherein
Y1 is Gly, Glu, Val, or Lys;
Y3 is Arg or Lys;
Y5 is Arg or Lys;
Y6 is Gly, Ser, Lys, Ile or Arg;
Y7 is Trp or absent;
Y8 is Val, Thr, Asp, Glu or absent; and
Y10 is Lys or absent.

In some embodiments, Y is a peptide sequence having the formula (IIg)

(IIg)
(SEQ ID NO: 11)
Y1-Pro-Y3-Ser-Y5-Y6-Y7-Y8-Cys-Y10 wherein
Y1 is Glu or Lys;
Y3 is Arg or Lys;
Y5 is Arg or Lys;
Y6 is Gly, Ser, Lys, Ile or Arg;
Y7 is Trp or absent;
Y8 is Val or absent; and
Y10 is Lys or absent.

In some embodiments, the peptide of formula (I) comprises at least three, at least four, at least five, at least six, at least seven, at least eight, at least nine, at least ten, at least eleven, at least twelve, at least thirteen, at least fourteen or at least fifteen Y residues in Y.

In some embodiments, Y1 to Y3 are present and Y4 to Y15 are absent.

In some embodiments, Y1 to Y11 are present and Y12 to Y15 are absent.

In some embodiments, Y1 to Y10 are present and Y11 to Y15 are absent.

In some embodiments, Y8 and Y15 are absent.
In some embodiments, Y3 and Y15 are absent
In some embodiments, Y3, Y14 and Y15 are absent.
In some embodiment Y5 is absent.
In some embodiments Y1, Y5, Y7, Y12, Y13, Y14 and Y15 are absent.
In some embodiments Y1, Y5, and Y7 are absent. In some embodiments, Y8 is absent. In some embodiments, Y3 is absent. In some embodiments Y1, Y5, Y7, and Y11-Y15 are absent. In some embodiments, Y8 and Y11-Y15 are absent. In some embodiments, Y3 and Y11-Y15 are absent.

In some embodiments, the present invention provides a compound of formula (I), wherein the compound comprises any one of the X/Y peptide sequence formula combinations presented in Table 1 below.

TABLE 1

Illustrative combinations of X and Y peptides of a compound of Formula (I)
Formula I combinations

| Combination Number | X Peptide Sequence Formula | Y Peptide Sequence Formula |
| --- | --- | --- |
| 1 | Ia | IIa |
| 2 | Ia | IIb |
| 3 | Ia | IIc |
| 4 | Ia | IId |
| 5 | Ia | IIe |
| 6 | Ia | IIf |
| 7 | Ia | IIg |
| 8 | Ib | IIa |
| 9 | Ib | IIb |
| 10 | Ib | IIc |
| 11 | Ib | IId |
| 12 | Ib | IIe |
| 13 | Ib | IIf |
| 14 | Ib | IIg |
| 15 | Ic | IIa |
| 16 | Ic | IIb |
| 17 | Ic | IIc |
| 18 | Ic | IId |
| 19 | Ic | IIe |
| 20 | Ic | IIf |
| 21 | Ic | IIg |
| 22 | Id | IIa |
| 23 | Id | IIb |
| 24 | Id | IIc |
| 25 | Id | IId |
| 26 | Id | IIe |
| 27 | Id | IIf |
| 28 | Id | IIg |

In some embodiments, the invention provides peptides, which may be isolated and/or purified, comprising, consisting essentially of, or consisting of, the following structural formula:

(I')
(SEQ ID NO: 21)
R$^{1'}$-X'-Y'-R$^{2'}$ or a pharmaceutically acceptable salt or solvate thereof, wherein R$^{1'}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g., methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g., PEG3 to PEG11), alone or as spacers of any of the foregoing;

R$^{2'}$ is —NH$_2$ or —OH;

X' is a peptide sequence having the formula (Ia')

(Ia')
(SEQ ID NO: 13)
X1-X2-X3-X4-X5-X6-X7-X8-X9-X10 wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg or Dapa;
X9 is Phe, Ala, Ile, Tyr, Lys, Arg, bhPhe or D-Phe; and
X10 is Lys, Phe or absent;
and provided that if Y' is absent, X7 is Ile; and
Y' is a peptide having the formula (IIa')

(IIa')
(SEQ ID NO: 16)
Y1-Y2-Y3-Y4-Y5-Y6-Y7-Y8-Y9-Y10-Y11-Y12-Y13-Y14-Y15 wherein
Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Arg, Ala, Pro, Val or absent;
Y7 is Trp, Lys, Gly, Ala Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein said compound of formula (I') is optionally PEGylated on R$^{1'}$, X', or Y'; and
wherein when said compound of formula (I') comprises two or more cysteine residues, at least two of said cysteine residues being linked via a disulfide bond.

In some embodiments, R$^{1'}$ is hydrogen, isovaleric acid, isobutyric acid or acetyl.

In some embodiments of the peptide compound of formula (I'), X' is a peptide sequence according to formula (Ia'), wherein
X1 is Asp, Ala, Ida, pGlu, bhAsp, Leu, D-Asp or absent;
X2 is Thr, Ala, or D-Thr;
X3 is His, Lys, D-His or Lys;
X4 is Phe, Ala, Dpa or D-Phe;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.

In some embodiments of the peptide compound of formula I', X' is a peptide sequence having the formula (Ib')

(Ib')
(SEQ ID NO: 14)
X1-Thr-His-X4-X5-X6-X7-X8-Phe-X10 wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile Lys, Glu, Phe, Gln or Arg; and
X10 is Lys or absent.

In some embodiments of the peptide compound of formula I', X' is a peptide sequence having the formula (Ic')

(Ic')
(SEQ ID NO: 15)
X1-Thr-His-X4-X5-Cys-Ile-X8-Phe-X10 wherein
X1 is Asp, Ida, pGlu, bhAsp or absent;
X4 is: Phe or Dpa;
X5 is Pro or bhPro;
X8 is Ile Lys, Glu, Phe, Gln or Arg; and
X10 is Lys or absent;

In some embodiments of the peptide compound of formula I', X' is a peptide sequence having the formula (Id')

(Id')
(SEQ ID NO: 4)
X1-Thr-His-Phe-X5-Cys-Ile-X8-Phe-X10 wherein
X1 is Asp, Glu, or Ida;
X4 is: Phe;
X5 is Pro or bhPro;
X8 is Ile, Lys, or Phe; and
X10 is absent;

In some embodiments of the peptide compound of formula I', Y' is a peptide sequence having the formula (IIb')

(IIb')
(SEQ ID NO: 17)
Y1-Y2-Y3-Y4-Y5-Y6-Y7-Y8-Cys-Y10 wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp or Ala;
Y8 is Val, Thr, Ala or Glu; and
Y10 is Met, Lys or absent.

In some embodiments of the peptide compound of formula I', Y' is a peptide sequence having the formula (IIc')

(IIc')
(SEQ ID NO: 18)
Y1-Y2-Y3-Ser-Lys-Gly-Trp-Y8-Cys-Y10 wherein
Y1 is Gly, Pro or D-Pro;
Y2 is Pro or Gly;
Y3 is Arg or Lys;
Y8 is Val or Thr; and
Y10 is Met, Lys or absent.

In some embodiments of the peptide compound of formula I', Y' is a peptide sequence having the formula (IId')

(IId')
(SEQ ID NO: 19)
Y1-Cys-Y3-Y4-Arg-Y6-Y7-Y8-Cys-Y10-Y11-Y12-Y13-Y14-Y15 wherein
Y1 is Val or Ala or absent;
Y3 is Gly, Pro or absent;
Y4 is His, Trp or Tyr;
Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

In some embodiments of the peptide compound of formula I', Y' is a peptide sequence having the formula (IIe')

(IIe')
(SEQ ID NO: 20)
Val-Cys-Y3-His-Arg-Y6-Y7-Y8-Cys-Tyr-Arg-Y12-Y13-Y14-Y15 wherein
Y3 is Gly or absent;
Y6 is Ser or Pro;
Y7 is Ile or Lys;
Y8 is Gly or absent;
Y12 is Arg or Ala;
Y13 is Cys, Val or absent;
Y14 is Cys, Arg, Thr or absent; and
Y15 is Arg or absent.

In some embodiments of the peptide compound of formula I', Y' is a peptide sequence having the formula (IIf')

(IIf')
(SEQ ID NO: 10)
Y1-Pro-Y3-Ser-Y5-Y6-Y7-Y8-Cys-Y10 wherein
Y1 is Gly, Glu, Val, or Lys;
Y3 is Arg or Lys;
Y5 is Arg or Lys;
Y6 is Gly, Ser, Lys, Ile or Arg;
Y7 is Trp or absent;
Y8 is Val, Thr, Asp, Glu or absent; and
Y10 is Lys or absent.

In some embodiments of the peptide compound of formula I', Y' is a peptide sequence having the formula (IIg')

(IIg')
(SEQ ID NO: 11)
Y1-Pro-Y3-Ser-Y5-Y6-Y7-Y8-Cys-Y10 wherein
Y1 is Glu or Lys;
Y3 is Arg or Lys;
Y5 is Arg or Lys;
Y6 is Gly, Ser, Lys, Ile or Arg;
Y7 is Trp or absent;
Y8 is Val or absent; and
Y10 is Lys or absent.

In some embodiments, the peptide of formula I' comprises at least three, at least four, at least five, at least six, at least seven, at least eight, at least nine, at least ten, at least eleven, at least twelve, at least thirteen, at least fourteen or at least fifteen Y residues in Y'.

In some embodiments, Y1 to Y3 are present and Y4 to Y15 are absent.

In some embodiments, Y1 to Y11 are present and Y12 to Y15 are absent.

In some embodiments, Y1 to Y10 are present and Y11 to Y15 are absent.

In some embodiments, Y8 and Y15 are absent.

In some embodiments, Y3 and Y15 are absent

In some embodiments, Y3, Y14 and Y15 are absent.

In some embodiment Y5 is absent.

In some embodiments Y1, Y5, Y7, Y12, Y13, Y14 and Y15 are absent.

In some embodiments, the present invention provides a compound of formula (I'), wherein the compound comprises any one of the X'/Y' peptide sequence formula combinations presented in Table 2 below.

TABLE 2

Illustrative combinations of X' and Y' peptides of a compound of Formula (I')
Formula I' combinations

| Combination Number | X' Peptide Sequence Formula | Y' Peptide Sequence Formula |
|---|---|---|
| 1 | Ia' | IIa' |
| 2 | Ia' | IIb' |
| 3 | Ia' | IIc' |
| 4 | Ia' | IId' |
| 5 | Ia' | IIe' |
| 6 | Ia' | IIf' |
| 7 | Ia' | IIg' |
| 8 | Ib' | IIa' |
| 9 | Ib' | IIb' |
| 10 | Ib' | IIc' |
| 11 | Ib' | IId' |
| 12 | Ib' | IIe' |
| 13 | Ib' | IIf' |
| 14 | Ib' | IIg' |
| 15 | Ic' | IIa' |
| 16 | Ic' | IIb' |
| 17 | Ic' | IIe' |
| 18 | Ic' | IId' |
| 19 | Ic' | IIe' |
| 20 | Ic' | IIf' |
| 21 | Ic' | IIg' |
| 22 | Id' | IIa' |
| 23 | Id' | IIb' |
| 24 | Id' | IIc' |
| 25 | Id' | IId' |
| 26 | Id' | IIe' |
| 27 | Id' | IIf' |
| 28 | Id' | IIg' |

In some embodiments, the invention provides peptides, which may be isolated and/or purified, comprising, consist ing essentially of, or consisting of, the following structural formula:

$$R^{1\prime\prime}-X^{\prime\prime}-Y^{\prime\prime}-R^{2\prime\prime} \quad (I^{\prime\prime})$$

(SEQ ID NO: 27)

or a pharmaceutically acceptable salt or solvate thereof, wherein $R^{1\prime\prime}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g., methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g., PEG3 to PEG11), alone or as spacers of any of the foregoing;

$R^{2\prime\prime}$ is —$NH_2$ or —OH;

X" is a peptide sequence having the formula (Ia")

$$X1-X2-X3-X4-X5-X6-X7-X8-X9-X10 \quad (Ia^{\prime\prime})$$

(SEQ ID NO: 22)

wherein

X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, D-His or Lys;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
and provided that if Y" is absent, X7 is Ile;
wherein said compound of formula I" is optionally PEGylated on $R^{1\prime\prime}$, X", or Y"; and
wherein when said compound of formula I" comprises two or more cysteine residues, at least two of said cysteine residues being linked via a disulfide bond.

In some embodiments, Y" is absent.

In some embodiments, $R^{1\prime\prime}$ is hydrogen, isovaleric acid, isobutyric acid or acetyl.

In some embodiments of the compound of formula (I"), X" is a peptide sequence according to formula (Ia"), wherein
X1 is Asp, Ala, Ida, pGlu, bhAsp, Leu, D-Asp or absent;
X2 is Thr, Ala, or D-Thr;
X3 is His, Lys, or D-His;
X4 is Phe, Ala, or Dpa;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys or absent.

In some embodiments of the compound of formula (I"), X" is a peptide sequence having the formula (Ib")

$$X1-Thr-His-X4-X5-X6-X7-X8-Phe-X10 \quad (Ib^{\prime\prime})$$

(SEQ ID NO: 23)

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys, Phe or absent.

In some embodiments of the compound of formula (I"), X" is a peptide sequence having the formula (Ic")

$$X1-Thr-His-X4-X5-Cys-Ile-X8-Phe-X10 \quad (Ic^{\prime\prime})$$

(SEQ ID NO: 24)

wherein
X1 is Asp, Ida, pGlu, bhAsp or absent;
X4 is Phe or Dpa;
X5 is Pro or bhPro;
X8 is Ile, Lys, Glu, Phe, Gln or Arg; and
X10 is Lys or absent.

In some embodiments of the compound of formula (I"), X" is a peptide sequence having the formula (Id")

$$X1-Thr-His-Phe-X5-Cys-Ile-X8-Phe-X10 \quad (Id^{\prime\prime})$$

(SEQ ID NO: 4)

wherein
X1 is Asp, Glu or Ida;
X4 is Phe;
X5 is Pro or bhPro;
X8 is Ile, Lys, or Phe; and
X10 is absent.

In some embodiments of the compound of formula (I"), Y" is a peptide having the formula (IIa")

$$Y1-Y2-Y3-Y4-Y5-Y6-Y7-Y8-Cys-Y10 \quad (IIa^{\prime\prime})$$

(SEQ ID NO: 25)

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp Ala or absent;
Y8 is Val, Thr, Lys, Ala, Glu or absent; and
Y10 is Met, Lys or absent.

In some embodiments of the compound of formula (I'), Y" is a peptide sequence according to formula (IIa") (SEQ ID NO:25)
wherein
Y1 is Gly, Glu, Val, or Lys
Y2 is Pro
Y3 is Arg or Lys;
Y4 is Ser
Y5 is Arg or Lys;
Y6 is Gly, Ser, Lys, Ile or Arg
Y7 is Trp or absent
Y8 is Val, Thr, Asp, Glu or absent;
Y10 is Lys or absent In some embodiments of the compound of formula (I″), Y″ is a peptide sequence according to formula (IIa″) (SEQ ID NO:25)
wherein
Y1 is Glu or Lys
Y2 is Pro
Y3 is Arg or Lys;
Y4 is Ser
Y5 is Arg or Lys;
Y6 is Gly, Ser, Lys, Ile or Arg;
Y7 is Trp or absent;
Y8 is Val or absent;
Y10 is Lys or absent In some embodiments of the compound of formula (I″), Y″ is a peptide sequence according to formula (IIa″) (SEQ ID NO:25)
wherein
Y1 is Gly, Pro or D-Pro;
Y2 is Pro or Gly;
Y3 is Arg or Lys;
Y4 is Ser;
Y5 is Lys;
Y6 is Gly;
Y7 is Trp;
Y8 is Val or Thr; and
Y10 is Met, Lys or absent.

In some embodiments of the compound of formula (I″), Y″ is a peptide sequence having the formula (IIb″)

```
                              (IIb'')
                              (SEQ ID NO: 26)
Y1-Y2-Y3-Ser-Lys-Gly-Trp-Y8-Cys-Y10
``` wherein
Y1 is Gly, Pro or D-Pro;
Y2 is Pro or Gly;
Y3 is Arg or Lys;
Y8 is Val or Thr; and
Y10 is Met, Lys or absent.

In some embodiments, the present invention provides a compound of formula (I″), wherein the compound comprises any one of the X″/Y″ peptide sequence formula combinations presented in Table 3 below.

TABLE 3

Illustrative combinations of X″ and Y″ peptides of a compound of Formula (I″)
Formula I″ combinations

| Combination Number | X″ Peptide Sequence Formula | Y″ Peptide Sequence Formula |
|---|---|---|
| 1 | Ia″ | IIa″ |
| 2 | Ia″ | IIb″ |
| 3 | Ib″ | IIa″ |
| 4 | Ib″ | IIb″ |
| 5 | Ic″ | IIa″ |
| 6 | Ic″ | IIb″ |
| 7 | Id″ | IIa″ |
| 8 | Id″ | IIb″ |

In some embodiments the peptide of formula (I″) comprises at least three, at least four, at least five, at least six, at least seven, at least eight, at least nine, or at least ten Y residues in Y″. In some embodiments, Y1 to Y3 are present and Y4 to Y10 are absent. In some embodiments Y5 is absent. In some embodiments Y1, Y5, and Y7 are absent. In some embodiments, Y8 is absent. In some embodiments, Y3 is absent.

In some embodiments, the present invention provides a compound of formula (I), (I′), or (I″), as described herein, each respectively comprising an X, X′, or X″ peptide sequence, according to the present disclosure, wherein X7 is Leu. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X7 is Val. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X7 is Cys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X7 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys and X7 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Ile and X7 is Cys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Cys and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Ile, X7 is Cys, and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys and C7 is Leu. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys and C7 is Val. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Ile and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Leu and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Val and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Leu and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, Leu, or Val. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is ASP or IDA, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp or IDA, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X2 is Thr, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X3 is His, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X4 is Phe, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X5 is Pro, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, Leu, or Val, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X2 is Thr, X6 is Cys, X7 is Ile and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X3 is His, X6 is Cys, X7 is Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X4 is Phe, X6 is Cys, X7 Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X5 is Pro, X6 is Cys, X7 is Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X2 is Thr, X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp or IDA, X2 is Thr, X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp or IDA, X2 is Thr, X3 is His, X4 is Phe, X5 is Pro, X6 is Cys, X7 is Ile, Leu, or Val, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is IDA, X2 is Thr, X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, wherein the compound comprises an $R^1$ that is isovaleric acid.

In some embodiments, the present invention provides a compound of formula (I), (I'), or (I"), as described herein, each respectively comprising an X, X', or X" peptide sequence, according to the present disclosure, wherein X1 is Asp or IDA, X2 is Thr, X3 is His, X4 is Phe, X5 is Pro, X6 is Cys, X7 is Ile, Leu, or Val, X8 is Lys, and X9 is Phe; wherein said peptide further comprises an $R^1$ that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro, X6 is Cys, X7 is Ile, Leu, or Val, and X8 is Lys; wherein said peptide further comprises an $R^1$ that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro, X6 is Cys, X7 is Ile, Leu, or Val, X8 is Lys, and X9 is Phe; wherein said peptide further comprises an R group that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro, X6 is Cys, X7 is Ile, X8 is Lys, and X9 is Phe; wherein said peptide further comprises an R group that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, wherein the compound comprises a peptide sequence that is 85% or higher (e.g., 85%, 90%, 91%, 92%, 93%, 94%, 95%, 96%, 97%, 98%, 99%, or 99.5%) homologous to an amino acid sequence set forth in any one of Tables 5-15. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf, or IIg', as described herein. In particular embodiments, formula (I") comprises (i) Ia", Ib", Ic", or Id" and, optionally, (ii) IIa" or IIb', as described herein.

In certain embodiments, a peptide or a peptide dimer of the present invention comprises any one of the compounds shown in any one of Tables 5-15.

In certain embodiments, a peptide or a peptide dimer of the present invention comprises any one of the amino acid sequences provided as SEQ ID NOS: 1-334 and 338-375, or as shown in any one of Tables 5-15

In certain embodiments, a peptide or a peptide dimer of the present invention comprises an amino acid sequence set forth in any one of Tables 5-15.

In certain embodiments, a peptide or a peptide dimer of the present invention has a structure shown in any one of Tables 5-15, e.g., Tables 7 or 12-15. In one certain embodiment, a peptide or a peptide dimer of the present invention comprises an amino acid sequence set forth in any one of Tables 5-15, e.g., Tables 7 or 12-15. In some embodiments, a peptide of the present invention comprises an amino acid sequence having at least about 85% identical or at least about 90%, 95%, 97%, 98%, 99% identical to any amino acid sequence set forth in any one of Tables 5-15, e.g., Tables 7 or 12-15, or any one of SEQ ID NOS: 1-334 and 338-375. In one certain embodiment, a peptide or a peptide dimer of the present invention comprises an amino acid sequence having at least about 85% identical or at least about 90%, 95%, 97%, 98%, 99% identical to any amino acid sequence set forth in Table 7 or any one of Tables 5-15.

It is understood that in the context of the invention, a peptide or peptide dimer comprising a peptide sequence shown in one of the accompanying Tables or sequence listing may have certain minor alterations to one or more amino acid residues of the peptide sequence, as compared to the native amino acid, yet still be considered to comprises the peptide sequence shown in the Tables or sequence listing. For example, one or more side chains of one or more amino acid residues present in the peptide or peptide dimer may be slightly altered due to the attachment of a linker or dimerization via cysteine residues, or an N-terminal or C-terminal amino acid may be amidated.

In some embodiments, a peptide or a peptide dimer of the present invention exhibits hepcidin activity. In some embodiments, a peptide or a peptide dimer of the present invention exhibits at least about 50%, 60%, 70%, 80%, 90%, 95%, 97%, 98%, 99%, greater than 99%, greater than 100%, greater than 110%, greater than 120%, greater than 150%, greater than 200% greater than 500%, or greater than 1000% of the activity of a reference hepcidin, (e.g., any one of the hepcidin reference compounds provided in Table 4). In some embodiments, the activity is an in vitro or an in vivo activity as described herein.

In some embodiments, a peptide or a peptide dimer of the present invention exhibits at least about 50%, 60%, 70%, 80%, 90%, 95%, 97%, 98%, 99%, or greater than 99% of the in vitro activity for inducing the degradation of human ferroportin protein as that of a reference hepcidin, (e.g., any one of the hepcidin reference compounds provided in Table 4), wherein the activity is measured according to the methods described herein (e.g., according to Example 2).

In some embodiments, a peptide or a peptide dimer of the present invention exhibits at least about 50%, 60%, 70%, 80%, 90%, 95%, 97%, 98%, 99%, or greater than 99% of the in vivo activity for inducing the reduction of free plasma iron in an individual as does a reference hepcidin, (e.g., any one of the hepcidin reference compounds provided in Table 4), wherein the activity is measured according to the methods described herein (e.g., according to Example 8).

In some embodiments, a peptide or a peptide dimer of the present invention exhibits increased hepcidin activity as compared to a hepcidin reference peptide, (e.g., any one of the hepcidin reference compounds provided in Table 4). In certain embodiments, a peptide or a peptide dimer of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, 500%, 700%, or 1000% greater activity than a reference hepcidin, (e.g., any one of the hepcidin reference compounds provided in Table 4). In some embodiments, a peptide or a peptide dimer of the present invention exhibits at least about 50%, 60%, 70%, 80%, 90%, 95%, 97%, 98%, 99%, or greater than 99% of the activity exhibited by a hepcidin reference compound. In some embodiments, the activity is an in vitro or an in vivo activity, e.g., an in vivo or an in vitro activity described herein. In certain embodiments, a peptide or a peptide dimer of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, 500%, 700%, or 1000% greater activity than a reference hepcidin, (e.g., any one of the hepcidin reference compounds provided in Table 4), wherein the activity is an in vitro activity for inducing the degradation of ferropontin, e.g., as measured according to Example 2; or wherein the activity is an in vivo activity for reducing free plasma iron, e.g., as measured according to Example 8.

In some embodiments, a peptide or a peptide dimer of the present invention binds ferroportin, e.g., human ferroportin. In some embodiments, a peptide or a peptide dimer of the present invention exhibits at least about 50%, 60%, 70%, 80%, 90%, 95%, 97%, 98%, 99%, or greater than 99% of the ferroportin binding ability that is exhibited by a reference hepcidin (e.g., any one of the hepcidin reference compounds provided in Table 4). In some embodiments, a peptide or a peptide dimer of the present invention has a lower $IC_{50}$ (i.e., higher binding affinity) for binding to ferroportin, (e.g., human ferroportin) compared to a reference hepcidin, (e.g., any one of the hepcidin reference compounds provided in Table 4). In some embodiments, the peptide of the present invention has an $IC_{50}$ in a ferroportin competitive binding assay which is at least about 10%, 20%, 30%, 40%, 50%, 60%, 70%, 80%, 90%, 100%, 200%, 300%, 400%, 500%, 700%, or 1000% lower than a reference hepcidin, (e.g., any one of the hepcidin reference compounds provided in Table 4).

In some embodiments, the present invention provides a compound of formula I, I', or I", as described herein, wherein the peptide exhibits increased stability (e.g., as measured by half-life, rate of protein degradation) as compared to a reference hepcidin, (e.g., any one of the hepcidin reference compounds provided in Table 4). In some embodiments, the present invention provides a dimer of such a compound, and in certain embodiments the dimer is a homodimer. In certain embodiments, the stability of a peptide or a peptide dimer of the present invention is increased at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a reference hepcidin, (e.g., any one of the hepcidin reference compounds provided in Table 4). In some embodiments, the stability is a stability that is described herein. In some embodiments, the stability is a plasma stability, e.g., as optionally measured according to the method described in Example 7.

In particular embodiments, the present invention provides a compound of formula I, I', or I", as described herein, wherein the peptide exhibits a longer half-life than a reference hepcidin, (e.g., any one of the hepcidin reference compounds provided in Table 4). In some embodiments, the present invention provides a dimer of such a compound, and in certain embodiments the dimer is a homodimer. In particular embodiments, a peptide or a peptide dimer of the present invention has a half-life under a given set of conditions (e.g., temperature, pH) of at least about 5 minutes, at least about 10 minutes, at least about 20 minutes, at least about 30 minutes, at least about 45 minutes, at least about 1 hour, at least about 2 hour, at least about 3 hours, at least about 4 hours, at least about 5 hours, at least about 6 hours, at least about 12 hours, at least about 18 hours, at least about 1 day, at least about 2 days, at least about 4 days, at least about 7 days, at least about 10 days, at least about two weeks, at least about three weeks, at least about 1 month, at least about 2 months, at least about 3 months, or more, or any intervening half-life or range in between, about 5 minutes, about 10 minutes, about 20 minutes, about 30 minutes, about 45 minutes, about 1 hour, about 2 hour, about 3 hours, about 4 hours, about 5 hours, about 6 hours, about 12 hours, about 18 hours, about 1 day, about 2 days, about 4 days, about 7 days, about 10 days, about two weeks, about three weeks, about 1 month, about 2 months, about 3 months, or more, or any intervening half-life or range in between. In some embodiments, the half life of a peptide or a peptide dimer of the present invention is extended due to its conjugation to one or more lipophilic substituent, e.g., any of the lipophilic substituents disclosed herein. In some embodiments, the half life of a peptide or a peptide dimer of the present invention is extended due to its conjugation to one or more polymeric moieties, e.g., any of the polymeric moieties disclosed herein. In certain embodiments, the temperature is about 25° C., about 4° C., or about 37° C., and the pH is a physiological pH, or a pH about 7.4.

In some embodiments, the half-life is measured in vitro using any suitable method known in the art, e.g., in some embodiments, the stability of a peptide or a peptide dimer of the present invention is determined by incubating the peptide or the peptide dimer with pre-warmed human serum (Sigma) at 37° C. Samples are taken at various time points, typically up to 24 hours, and the stability of the sample is analyzed by separating the peptide or peptide dimer from the serum proteins and then analyzing for the presence of the peptide or peptide dimer of interest using LC-MS.

In some embodiments, the stability of the peptide is measured in vivo using any suitable method known in the art, e.g., in some embodiments, the stability of a peptide or a peptide dimer is determined in vivo by administering the peptide or peptide dimer to a subject such as a human or any mammal (e.g., mouse) and then samples are taken from the subject via blood draw at various time points, typically up to 24 hours. Samples are then analyzed as described above in regard to the in vitro method of measuring half-life. In some embodiments, in vivo stability of a peptide or a peptide dimer of the present invention is determined via the method disclosed in Example 7.

In some embodiments, the present invention provides a compound of formula I, I', or I", as described herein, or a dimer thereof, wherein the peptide or the dimer exhibits improved solubility or improved aggregation characteristics as compared to a reference hepcidin, (e.g., any one of the hepcidin reference compounds provided in Table 4). Solubility may be determined via any suitable method known in the art. In some embodiments, suitable methods known in the art for determining solubility include incubating peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide is more soluble in a given liquid than is a reference hepcidin (e.g., any one of the hepcidin reference compounds provided in Table 4).

In some embodiments, the present invention provides a compound of formula I, I', or I", as described herein, or a dimer thereof, wherein the peptide or the dimer exhibits less degradation (i.e., more degradation stability), e.g., greater than or about 10% less, greater than or about 20% less, greater than or about 30% less, greater than or about 40 less, or greater than or about 50% less than a reference hepcidin (e.g., any one of the hepcidin reference compounds provided in Table 4). In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent sequences with enhanced shelf lifes.

In some embodiments, the present invention provides compositions and medicaments comprising at least one peptide or peptide dimer as disclosed herein. In some embodiments, the present invention provides a method of manufacturing medicaments comprising at least one peptide or peptide dimer as disclosed herein for the treatment of diseases of iron metabolism, such as iron overload diseases. In some embodiments, the present invention provides a method of manufacturing medicaments comprising at least one peptide or peptide dimer as disclosed herein for the treatment of diabetes (Type I or Type II), insulin resistance, or glucose intolerance.

Also provided are methods of treating a disease of iron metabolism in a subject, such as a mammalian subject, and preferably a human subject, comprising administering at least one peptide, peptide dimer, or composition as disclosed herein to the subject. In some embodiments, the peptide, peptide dimer, or the composition is administered in a therapeutically effective amount. Also provided are methods of treating diabetes (Type I or Type II), insulin resistance, or glucose intolerance in a subject, such as a mammalian subject, and preferably a human subject, comprising administering at least one peptide, peptide dimer, or composition as disclosed herein to the subject. In some embodiments, the peptide, peptide dimer, or composition is administered in a therapeutically effective amount.

In some embodiments, the peptide, or peptide dimer of this invention is synthetically manufactured. In other embodiments, the peptide or peptide dimer of this invention is recombinantly manufactured.

In some embodiments, the invention provides a process for manufacturing a compound, peptide, peptide analogue, peptide dimer, or pharmaceutical composition as disclosed herein.

In some embodiments, the invention provides a device comprising at least one peptide, peptide analogue, or peptide dimer of the present invention, or pharmaceutically acceptable salt or solvate thereof for delivery of the peptide analogue or the peptide dimer to a subject.

In some embodiments, the present invention provides methods of binding a ferroportin or inducing ferroportin internalization and degradation which comprises contacting the ferroportin with at least one peptide or peptide analogue, peptide dimer, or composition as disclosed herein.

In some embodiments, the present invention provides kits comprising at least one peptide, peptide analogue, peptide dimer, or composition as disclosed herein packaged together with a reagent, a device, instructional material, or a combination thereof.

In some embodiments, the present invention provides complexes which comprise at least one peptide or peptide dimer as disclosed herein bound to a ferroportin, preferably a human ferroportin, or an antibody, such as an antibody which specifically binds a peptide or a peptide dimer as disclosed herein, Hep25, or a combination thereof.

In some embodiments, the compound has a measurement (e.g., an EC50) of less than 500 nM within the Fpn internalization assay. As a skilled person will realize, the function of the peptide is dependent on the tertiary structure of the peptide and the binding surface presented. It is then possible to make minor changes of the sequence that do not affect the fold or are not on the binding surface and maintain function. In other embodiments, the compound of the invention is a peptide or peptidomimetic compound, or a dimer thereof having 85% or higher (e.g., 85%, 90%, 91%, 92%, 93%, 94%, 95%, 96%, 97%, 98%, 99%, or 99.5%) identity or homology to an amino acid sequence of any compound of formula I, I', or I" that exhibits an activity, or lessens a symptom of a disease or indication for which hepcidin is involved.

In some embodiments, the peptide, peptide analogue, or dimer thereof of the invention may comprise functional fragments or variants thereof that have at most 10, 9, 8, 7, 6, 5, 4, 3, 2, or 1 amino acid substitutions compared to one or more of the specific sequences recited below.

In addition to the methods disclosed herein in Example 1, the peptides and the peptide dimers of the present invention may be produced using methods known in the art including chemical synthesis, biosynthesis or in vitro synthesis using recombinant DNA methods, and solid phase synthesis. See e.g. Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, IL, which are herein incorporated by reference. The peptides of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) Protein Purification, Springer-Verlag, NY, which are herein incorporated by reference. Alternatively, the peptides of the present invention may be made by recombinant DNA techniques known in the art. Thus, polynucleotides that encode the polypeptides of the present invention are contemplated herein. In preferred embodiments, the polynucleotides are isolated. As used herein "isolated polynucleotides" refers to polynucleotides that are in an environment different from that in which the polynucleotide naturally occurs.

In certain embodiments, peptides of the present invention bind ferroportin, preferably human ferroportin. Preferred peptides of the present invention specifically bind human ferroportin. As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The peptides of the present invention that mimic the hepcidin activity of Hep25, the bioactive human 25-amino acid form, are herein referred to as "mini-hepcidins". As used herein, in certain embodiments, a compound having "hepcidin activity" means that the compound has the ability to lower plasma iron concentrations in subjects (e.g. mice or humans), when administered thereto (e.g. parenterally injected or orally administered), in a dose-dependent and time-dependent manner. See e.g. as demonstrated in Rivera et al. (2005), Blood 106:2196-9. In some embodiments, the peptides of the present invention lower the plasma iron concentration in a subject by at least about 1.2, 1.5, 2, 3, 4, 5, 6, 7, 8, 9, or 10-fold, or at least about 5%, 10%, 20%, 25%, 30%, 40%, 50%, 60%, 70%, 80%, 90%, or about 99%.

In some embodiments, the peptides of the present invention have in vitro activity as assayed by the ability to cause the internalization and degradation of ferroportin in a ferroportin-expressing cell line as taught in Nemeth et al. (2006) Blood 107:328-33. In vitro activity may be measured by the dose-dependent loss of fluorescence of cells engineered to display ferroportin fused to green fluorescent protein as in Nemeth et al. (2006) Blood 107:328-33. Aliquots of cells are incubated for 24 hours with graded concentrations of a reference preparation of Hep25 or a mini-hepcidin. As provided herein, the EC50 values are provided as the concentration of a given compound (e.g. peptide) that elicits 50% of the maximal loss of fluorescence generated by the reference Hep25 preparation. EC50 of Hep25 preparations in this assay range from 5 to 15 nM and preferred mini-hepcidins have EC50 values in in vitro activity assays of about 1,000 nM or less. In certain embodiments, a peptide of the present invention has an EC50 in an in vitro activity assay (e.g., as described in Nemeth et al. (2006) Blood 107:328-33 or Example 2 herein) of less than about any one of 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, a peptide analogue or biotherapeutic composition has an $EC_{50}$ value of about 1 nM or less.

Other methods known in the art for calculating the hepcidin activity and in vitro activity of peptides according to the present invention may be used. For example, the in vitro activity of compounds may be measured by their ability to internalize cellular ferroportin, which is determined by immunohistochemistry or flow cytometry using antibodies which recognizes extracellular epitopes of ferroportin. Alternatively, the in vitro activity of compounds may be measured by their dose-dependent ability to inhibit the efflux of iron from ferroportin-expressing cells that are preloaded with radioisotopes or stable isotopes of iron, as in Nemeth et al. (2006) Blood 107:328-33.

Conjugation

The skilled person will be well aware of suitable techniques for preparing the compounds employed in the context of the invention. For examples of suitable chemistry, see, e.g., WO98/08871, WO00/55184, WO00/55119, Madsen et al (J. Med. Chem. 2007, 50, 6126-32), and Knudsen et al. 2000 (J. Med Chem. 43, 1664-1669).

The side chains of one or more amino acid residues (e.g. Lys residues) in a compound of the invention may be further conjugated (i.e. covalently attached) to a lipophilic substituent. The lipophilic substituent may be covalently bonded to an atom in the amino acid side chain, or alternatively may be conjugated to the amino acid side chain via one or more spacers. The amino acid(s) in question may be part of the peptide moiety X, or a part of the peptide moiety Y.

Without wishing to be bound by any particular theory, it is believed that the lipophilic substituent binds to albumin in the blood stream, thereby shielding the peptide analogue of the invention from enzymatic degradation, and thus enhancing its half-life. The spacer, when present, may provide spacing between the peptide analogue and the lipophilic substituent.

In certain embodiments, the lipophilic substituent may comprise a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A lipophilic substituent may be conjugated to any amino acid side chain in a compound of the invention. In certain embodiment, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. In certain embodiments, the lipophilic substituent is conjugated to Lys. An amino acid shown as Lys in any of the formulae provided herein may be replaced by, e.g., Dbu, Dpr or Orn where a lipophilic substituent is added.

In further embodiments of the present invention, alternatively or additionally, the side-chains of one or more amino acid residues in the compound of the invention may be conjugated to a polymeric moiety, for example, in order to increase solubility and/or half-life in vivo (e.g. in plasma) and/or bioavailability. Such modifications are also known to reduce clearance (e.g. renal clearance) of therapeutic proteins and peptides.

As used herein, "Polyethylene glycol" or "PEG" is a polyether compound of general formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or copolymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are peptides that are prepared for purpose of half life extension, for example, mono-activated, alkoxy-terminated polyalkylene oxides (POA's) such as mono-methoxy-terminated polyethyelene glycols (mPEG's); bis activated polyethylene oxides (glycols) or other PEG derivatives are also contemplated. Suitable polymers will vary substantially by weights ranging from about 70 to about 40,000 or from about 200 to about 40,000 are usually selected for the purposes of the present invention. Molecular weights from 200 to 2,000 are preferred and 200 to 500 are particularly preferred. There are different forms of PEG are also available, depending on the initiator used for the polymerization process—the most common initiator is a monofunctional methyl ether PEG, or methoxypoly(ethylene glycol), abbreviated mPEG.

As used herein, lower-molecular-weight PEGs are also available as pure oligomers, referred to as monodisperse, uniform, or discrete. These are used in certain embodiments of the present invention.

PEGs are also available with different geometries: Branched PEGs have three to ten PEG chains emanating from a central core group; Star PEGs have 10 to 100 PEG chains emanating from a central core group; Comb PEGs have multiple PEG chains normally grafted onto a polymer backbone. PEGs can also be linear. The numbers that are often included in the names of PEGs indicate their average molecular weights (e.g. a PEG with n=9 would have an average molecular weight of approximately 400 daltons, and would be labeled PEG 400.

As used herein, "PEGylation" is the act of covalently coupling a PEG structure to the peptide of the invention, which is then referred to as a "PEGylated peptide". In some embodiments, the X moiety of formula I, the Y moiety of formula I, the $R^1$ moiety of formula I, the $R^2$ moiety of formula I, or any combination thereof, is PEGylated. In some embodiments, the X' moiety of formula I', the Y' moiety of formula I', the $R^{1'}$ moiety of formula I', the $R^{2'}$ moiety of formula I', or any combination thereof, is PEGylated. In some embodiments, the X" moiety of formula I", the Y" moiety of formula I", the $R^{1''}$ moiety of formula I", the $R^{2''}$ moiety of formula I", or any combination thereof, is PEGylated. In some embodiments, one or more side chains of an amino acid in the peptide of formula I, formula I', or formula I" is PEGylated. In certain embodiments, the PEG of the PEGylated side chain is a PEG with a molecular weight from about 200 to about 40,000. In some embodiments, a spacer of a peptide of formula I, formula I', or formula I" is PEGylated. In certain embodiments, the PEG of a PEGylated spacer is PEG3, PEG4, PEG5, PEG6, PEG7, PEG8, PEG9, PEG10, or PEG11. In certain embodiments, the PEG of a PEGylated spacer is PEG3 or PEG8. In certain embodiments, the PEG of a PEGylated spacer is PEG3 or PEG8.

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57 and Tsukada, et al. (1984), J. Natl. Cancer Inst., vol. 73, 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a compound of the invention may comprise two or more such polymeric moieties, in which case the total molecular weight of all such moieties will generally fall within the ranges provided above.

In some embodiments, the polymeric moiety may be coupled (by covalent linkage) to an amino, carboxyl or thiol group of an amino acid side chain. Preferred examples are the thiol group of Cys residues and the epsilon amino group of Lys residues, and the carboxyl groups of Asp and Glu residues may also be involved.

The skilled worker will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two step process. As used herein, for a single oxidation step the trityl protecting group is often employed during assembly, allowing deprotection during cleavage, followed by solution oxidation. When a second disulfide bond is required one has the option of native or selective oxidation. For selective oxidation requiring orthogonal protecting groups Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation the trityl protecting group is used for all cysteines, allowing for natural folding of the peptide.

A skilled worker will be well aware of suitable techniques which can be used to perform the oxidation step.

Peptide Dimers

The term "dimer," as in a peptide dimer, refers to compounds in which two peptide chains are linked, either identical (homo-dimer) or non-identical (hetero-dimer) through a linking moiety. A cysteine dimer is then two peptides chains linked through the amino acid cysteine disulfide bond.

In some embodiments, the peptides of the present invention may be active in a dimer conformation or a hetero-dimer conformation, in particular when free cysteine residues are present in the peptide. In certain embodiments, this occurs either as a synthesized dimer or, in particular, when a free cysteine monomer peptide is present and under oxidizing conditions, dimerizes. In some embodiments, the dimer is a homodimer. In other embodiments, the dimer is a heterodimer.

In certain embodiments, a peptide analogue of the present invention is a peptide dimer comprising a peptide of the invention. In particular embodiments, the peptide dimers comprise a peptide of formula I, a peptide of formula I', or a peptide of formula I". In particular embodiments, the peptide dimers comprise two peptides of formula I, two peptides of formula I', or two peptides of formula I". In certain embodiments, the peptide dimers are homodimers. In particular embodiments wherein the peptide dimer comprises a peptide of formula I, X has the formula Ia, Ib, Ic, or Id. In particular embodiments wherein the peptide dimer comprises a peptide of formula I, Y has the formula IIa, IIb, IIc, IId, IIe, IIf, or IIg. In particular embodiments wherein the peptide dimer comprises a peptide of formula I', X' has the formula Ia', Ib', Ic', or Id'. In particular embodiments wherein the peptide dimer comprises a peptide of formula I', Y' has the formula IIa', IIb', IIc', IId', IIe', IIf, or IIg'. In particular embodiments wherein the peptide dimer comprises a peptide of formula I", X" has the formula Ia", Ib", Ic", or Id". In particular embodiments wherein the peptide dimer comprises a peptide of formula I", Y" has the formula IIa" or IIb".

In some embodiments, the dimer is between two X groups of formula I, two X' groups of formula I', or two X" groups of formula I", e.g., the two peptides of the dimer are linked through two X groups of formula I, two X' groups of formula I', or two X" groups of formula I". In some embodiments, the dimer comprises two X groups of formula I, two X' groups of formula I', or two X" groups of formula I". In some embodiments, the two X groups, X' groups, or X" groups in the dimers comprise the same amino acid residues. In some embodiments, the two X groups, X' groups, or X" groups in the dimers comprise different amino acid residues (i.e., each amino acid in each of the two X, X' or X" groups is independently selected). In some embodiments, the dimer is between two Y groups of formula I, two Y groups of formula I', or two Y" groups of formula I", e.g., the two peptides of the dimer are linked through two Y groups of formula I, two Y' groups of formula I', or two Y" groups of formula I". In some embodiments, the dimer comprises two Y groups of formula I, two Y groups of formula I', or two Y" groups of formula I". In some embodiments, the two Y groups, Y' groups, or Y" groups in the dimer comprise the same amino acid residues. In some embodiments, the two Y groups, Y' groups or Y" groups in the dimer comprise different amino acid residues (i.e., each amino acid in each of the Y, Y' or Y" groups is independently selected). In some embodiments, a dimer is between an X group of formula I and a Y group of formula I (e.g., the two peptides of the dimer are linked through an X group of formula I and a Y group of formula I), an X' group of formula I' and a Y' group of formula I (e.g., the two peptides of the dimer are linked through an X' group of formula I' and a Y' group of formula I'), or an X" group of formula I" and a Y" group of formula I" (e.g., the two peptides of the dimer are linked through an X" group of formula I" and a Y" group of formula I").

In particular embodiments, a peptide dimer of the present invention comprises a peptide comprising: a peptide sequence set forth in any one of Tables 5-15 or SEQ ID NOs: 1-334 and 338-375; or a peptide sequence having at least 85%, at least 90%, at least 91%, at least 92%, at least 93%, at least 94%, at least 95%, at least 96%, at least 97%, at least 98%, or at least 99% identity to a peptide sequence set forth in any one of Tables 5-15 or SEQ ID NOs: 1-334 and 338-375. In particular embodiments, a peptide dimer of the present invention is a homodimer comprising two peptides, each comprising: a peptide sequence set forth in any one of Tables 5-15 or SEQ ID NOs: 1-334 and 338-375; or a peptide sequence having at least 85%, at least 90%, at least 91%, at least 92%, at least 93%, at least 94%, at least 95%, at least 96%, at least 97%, at least 98%, or at least 99% identity to a peptide sequence set forth in any one of Tables 5-15 or SEQ ID NOs: 1-334 and 338-375. In particular embodiments, a peptide dimer of the present invention comprises a compound set forth in any one of Tables 5-15. In particular embodiments, a peptide dimer of the present invention is a homodimer comprising two peptides, each comprising a compound set forth in any one of Tables 5-15.

In certain embodiments, the peptide dimers comprise two peptides dimerized via a disulfide linkage between a cysteine residue present in one of the peptides and a cysteine residue present in the second peptide, i.e., an intermolecular disulfide bond between these cysteine residues.

In certain embodiments, the peptide dimers comprise two peptides dimerized by covalent attachment of each peptide to a common linking moeity, i.e., a linker. A variety of linkers suitable for dimerizing two peptides are known in the art and commercially available, including, e.g., diethylene glycol (DIG), iminodiacetic acid (IDA), β-Ala-IDA, PEG13, and PEG25. In particular embodiments, peptide dimers include any of the linking moieties shown below or have any of the structures shown below. In particular embodiments, peptide dimers are dimerized via both a linking moiety and a disulphide bond between a cysteine residue in one peptide and a cysteine residue in the other peptide of the dimer.

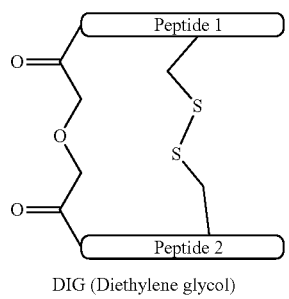

DIG (Diethylene glycol)

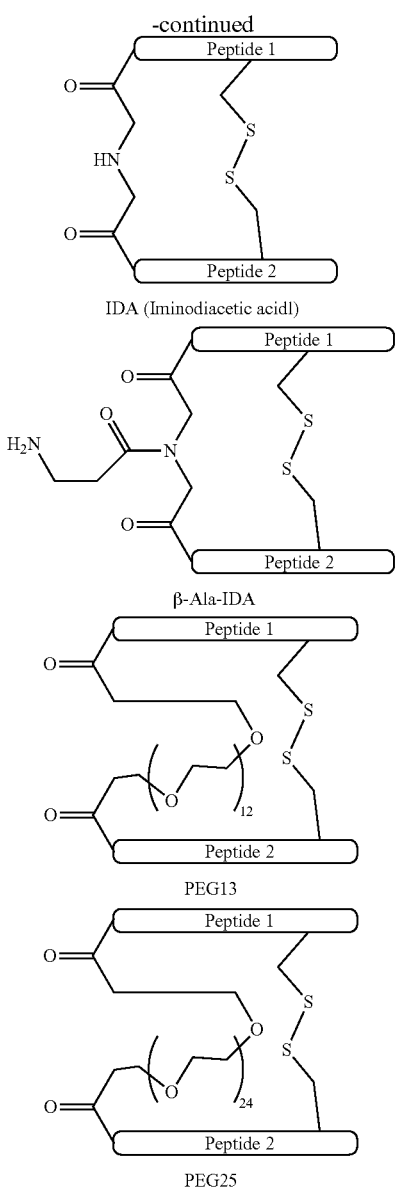

In certain embodiments, the linking moiety comprises the formula: —NH—$R_{20}$—NH—, wherein $R_{20}$ is a lower ($C_{1-20}$) alkyl. In certain embodiments, the linking moiety comprises the formula: —CO—$(CH_2)$n-(X—$(CH_2)$m)o-X—$(CH_2)$pCO—, wherein n is 1-3, m is 1-3, p is 1-3, o is 0-24, and X is O or NH. In one embodiment, n, m and p are each 2, o is 1-25, X is O.

In certain embodiments, the linking moiety comprises the formula: —NH—$(CH_2)$α-[O—$(CH_2)$p]-O—$(CH_2)$s-Y—, wherein α, β and ε are each integers whose values are independently selected from 1 to 6, δ is 0 or 1, γ is an integer selected from 0 to 10, and γ is selected from NH or CO, provided that P is 2 when γ is greater than 1.

In various embodiments, the linker is attached to the N-terminal amino acid of one or both peptides of the dimer, the linker is attached to the C-terminal amino acid of one or both peptides of the dimer, or the linker is attached to an internal amino acid of one or both peptides of the dimer. In one embodiment, the linker is attached to lysine residues in each of the peptides of the dimer. In particular embodiments, the linker is not attached to the N-terminal amino acid of one or both peptides of the dimer.

In particular embodiments, one or both peptides present in a dimer comprise an amino acid residue that is conjugated (i.e., covalently attached) to a lipophilic substituent, including any of those described herein. In certain embodiments, one or both peptides present in a dimer comprise an amino acid residue that is conjugated to a polymeric moiety, including any of those described herein. In certain embodiments, one or both of the peptides present in the peptide dimers is conjugated to an acidic compound, e.g., isovaleric acid, isobutyric acid, valeric acid, or the like.

In particular embodiments, a linking moiety present in a dimer is conjugated (i.e., covalently attached) to a lipophilic substituent, including any of those described herein. In certain embodiments, a linking moiety present in a dimer is conjugated to a polymeric moiety, including any of those described herein. In certain embodiments, a linking moiety present in a peptide dimer is conjugated to an acidic compound, e.g., isovaleric acid, isobutyric acid, valeric acid, or the like.

Pharmaceutical Compositions

It is to be understood that the inclusion of a peptide analogue or a dimer thereof of the invention (i.e., one or more peptide analogues of the invention or one or more peptide dimers of the present invention) in a pharmaceutical composition also encompasses inclusion of a pharmaceutically acceptable salt or solvate of a peptide analogue or a peptide dimer of the invention.

The invention also provides a pharmaceutical composition comprising a peptide analogue, or a pharmaceutically acceptable salt or solvate thereof, according to the invention. In particular embodiments, the invention provides a pharmaceutical composition comprising a peptide dimer, or a pharmaceutically acceptable salt or solvate thereof, according to the invention. In particular embodiments, the pharmaceutical compositions further comprise one or more pharmaceutically acceptable carrier, excipient, or vehicle.

The invention also provides a pharmaceutical composition comprising a peptide analogue, or a pharmaceutically acceptable salt or solvate thereof, for treating a variety of conditions, diseases, or disorders as disclosed herein elsewhere (see, e.g., therapeutic uses, supra). In particular embodiments, the invention provides a pharmaceutical composition comprising a peptide dimer, or a pharmaceutically acceptable salt or solvate thereof, for treating a variety of conditions, diseases, or disorders as disclosed herein elsewhere (see, e.g., therapeutic uses, supra).

The peptide analogues, including the peptide dimers, of the present invention may be formulated as pharmaceutical compositions which are suited for administration with or without storage, and which typically comprise a therapeutically effective amount of at least one peptide analogue of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, PA, USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration. Pharmaceutically acceptable carriers or diluents include those used in formulations suitable for e.g. oral, intravitreal, rectal, vaginal, nasal, topical, enteral or parenteral (including subcutaneous (SC), intramuscular (IM), intravenous (IV), intradermal and transdermal) administration or administration by inhalation. The formulations may conveniently be presented in unit dosage form and may be prepared by any of the methods well known in the art of pharmaceutical formulation.

Subcutaneous or transdermal modes of administration may be particularly suitable for the peptide analogues of the invention.

Further embodiments of the invention relate to devices, dosage forms and packages used to deliver the pharmaceutical formulations of the present invention. Thus, at least one peptide analogue or specified portion or variant in either the stable or preserved formulations or solutions described herein, can be administered to a patient in accordance with the present invention via a variety of delivery methods, including SC or IM injection; transdermal, pulmonary, transmucosal, implant, osmotic pump, cartridge, micro pump, or other means appreciated by the skilled artisan as well-known in the art.

Still further embodiments of the invention relate to oral formulations and oral administration. Formulations for oral administration may rely on the co-administration of adjuvants (e.g. resorcinols and/or nonionic surfactants such as polyoxyethylene oleyl ether and n-hexadecylpolyethylene ether) to artificially increase the permeability of the intestinal walls, and/or the co-administration of enzymatic inhibitors (e.g. pancreatic trypsin inhibitors, diisopropylfluorophosphate (DFF) or trasylol) to inhibit enzymatic degradation. The active constituent compound of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

Dosages

A typical dosage of a peptide analogue, e.g., a peptide or a dimer of the invention, as employed in the context of the present invention may be in the range from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. As already indicated to some extent above, the exact dosage employed will depend, inter alia, on: the nature and severity of the disease or disorder to be treated; the sex, age, body weight and general condition of the subject to be treated; possible other, concomitant, disease or disorder that is undergoing or is to undergo treatment; as well as other factors that will be known to a medical practitioner of skill in the art.

A peptide analogue, e.g., a peptide or a dimer, of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like.

Such regular peptide analogue, peptide, or dimer administration regimens of the invention may, in certain circumstances such as, e.g., during chronic long-term administration, be advantageously interrupted for a period of time so that the medicated subject reduces the level of or stops taking the medication, often referred to as taking a "drug holiday." Drug holidays are useful for, e.g., maintaining or regaining sensitivity to a drug especially during long-term chronic treatment, or to reduce unwanted side-effects of long-term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long-term administration). In some embodiments, the drug holiday may be a reduction in the dosage of the drug (e.g. to below the therapeutically effective amount for a certain interval of time). In other embodiments, administration of the drug is stopped for a certain interval of time before administration is started again using the same or a different dosing regimen (e.g. at a lower or higher dose and/or frequency of administration). A drug holiday of the invention may thus be selected from a wide range of time-periods and dosage regimens. An exemplary drug holiday is two or more days, one or more weeks, or one or more months, up to about 24 months of drug holiday. So, for example, a regular daily dosing regimen with a peptide, a peptide analogue, or a dimer of the invention may, for example, be interrupted by a drug holiday of a week, or two weeks, or four weeks, after which time the preceding, regular dosage regimen (e.g. a daily or a weekly dosing regimen) is resumed. A variety of other drug holiday regimens are envisioned to be useful for administering the peptides, the dimers, and the peptide analogues of the invention.

Thus, the peptide analogue, peptide, or dimer may be delivered via an administration regime which comprises two or more administration phases separated by respective drug holiday phases.

During each administration phase, the peptide analogue, peptide, or dimer is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the peptide analogue to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the peptide analogue the peptide, or the peptide dimer of the present invention.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of the following drug holiday phase is longer than the dosing interval used in that administration pattern. Where the dosing interval is irregular, the duration of the drug holiday phase may be greater than the mean interval between doses over the course of the administration phase. Alternatively the duration of the drug holiday may be longer than the longest interval between consecutive doses during the administration phase.

The duration of the drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime comprises at least 2 administration phases. Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with a peptide analogue, a peptide or a peptide dimer of the invention, then typically the same combination of drugs or active agents is given in consecutive administration phases. In certain embodiments, the recipient subject is human.

Devices and Kits

In some embodiments, the invention relates to a device comprising one or more peptides, peptide analogues, peptide dimers or pharmaceutically acceptable salts or solvates thereof of the invention, for delivery of the compound of the present invention to a subject. Thus, one or more peptide analogues, peptides, dimers, or pharmaceutically acceptable salts or solvates thereof can be administered to a patient in accordance with the present invention via a variety of delivery methods including intravenous, subcutaneous, intramuscular, or intraperitoneal injection; oral administration, transdermally, by pulmonary or transmucosal administration, by implant or osmotic pump, by cartridge or micro pump, or by other means appreciated by the skilled artisan, as well-known in the art.

In some embodiments, the invention relates to a kit comprising one or more peptide analogues or pharmaceutically acceptable salts or solvates thereof of the invention. In some embodiments, the invention relates to a kit comprising one or more peptide dimer of the present invention, or pharmaceutically acceptable salts or solvates thereof. In other embodiments, the kit comprises one or more pharmaceutical compositions comprising one or more peptide analogues or pharmaceutically acceptable salts or solvates thereof. In certain embodiments, the kit further comprises packaging or instructions for use. In other embodiments, the kit comprises one or more pharmaceutical compositions comprising one or more peptide dimer of the present invention, or pharmaceutically acceptable salts or solvates thereof. In certain embodiments, the kit further comprises packaging or instructions for use.

Combination Therapy

As noted above, it will be understood that reference in the following to a peptide analogue of the invention (e.g., the compounds listed in any one of Tables 5-15, for example compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 66, 67, 68, 69, 70, 71, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 105, 106, 107, 108, 109, 110, 111, 112, 113, 114, 115, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 293, 297, 298, 299, 300, 301, 302, 303, 304, 305, 306, 307, 308, 309, 310, 355, 356, 357, 358, 359, 360, 361 or dimers thereof, e.g., any one of the peptide dimers disclosed in Tables 12-15, for example compounds 311-353 also extends to a pharmaceutically acceptable salt or solvate thereof, as well as to a composition comprising more than one different peptide, peptide analogue, or peptide dimer of the invention.

In certain embodiments, a peptide analogue or a peptide dimer of the invention may have some benefit if administered in combination with an iron chelator, such as Deferoxamine and Deferasirox (Exjade™)

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

Abbreviations

DCM: dichloromethane
DMF: N,N-dimethylformamide
NMP: N-methylpyrolidone
HBTU: O-(Benzotriazol-1-yl)-N,N,N',N'-tetramethyluronium hexafluorophosphate
HATU: 2-(7-aza-1H-benzotriazole-1-yl)-1,1,3,3-tetramethyluronium hexafluorophosphate
DCC: Dicyclohexylcarbodiimide
NHS: N-hydoxysuccinimide
DIPEA: diisopropylethylamine
EtOH: ethanol
Et2O: diethyl ether
Hy: hydrogen
TFA: trifluoroacetic acid
TIS: triisopropylsilane
ACN: acetonitrile
HPLC: high performance liquid chromatography
ESI-MS: electron spray ionization mass spectrometry
PBS: phosphate-buffered saline
Boc: t-butoxycarbonyl
Fmoc: Fluorenylmethyloxycarbonyl
Acm: acetamidomethyl
IVA: Isovaleric acid (or Isovaleryl)
K( ): In the peptide sequences provided herein, wherein a compound or chemical group is presented in parentheses directly after a Lysine residue, it is to be understood that the compound or chemical group in the parentheses is a side chain conjugated to the Lysine residue. So, e.g., but not to be limited in any way, K(PEG8) indicates that a PEG8 moiety is conjugated to a side chain of this Lysine. For a few non-limiting examples of such a conjugated Lysines, please see, e.g., compounds 54 and 90.
Palm: Indicates conjugation of a palmitic acid (palmitoyl).

As used herein "C( )" refers to a cysteine residue involved in a particular disulfide bridge. For example, in Hepcidin, there are four disulfide bridges: the first between the two C(1) residues; the second between the two C(2) residues; the third between the two C(3) residues; and the fourth between the two C(4) residues. Accordingly, in some embodiments, the sequence for Hepcidin is written as follows: Hy-DTHFPIC(1)IFC(2)C(3)GC(2)C(4)HRSKC(3)GMC(4)C(1)KT-OH (SEQ ID NO:335); and the sequence for other peptides may also optionally be written in the same manner.

The following examples are provided to illustrate certain embodiments of the invention and are not intended to limit the scope of the invention.

Example 1

Synthesis of Compounds

Unless otherwise specified, reagents and solvents employed in the following were available commercially in standard laboratory reagent or analytical grade, and were used without further purification.

Procedure for Solid-Phase Synthesis of Peptides

Illustrative compounds of the invention (e.g., Compound No. 2) were chemically synthesized using optimized 9-fluorenylmethoxy carbonyl (Fmoc) solid phase peptide synthesis protocols. For C-terminal amides, rink-amide resin was used, although wang and trityl resins were also used to produce C-terminal acids. The side chain protecting groups were as follows: Glu, Thr and Tyr: O-tButyl; Trp and Lys: t-Boc (t-butyloxycarbonyl); Arg: N-gamma-2,2,4,6,7-pentamethyldihydrobenzofuran-5-sulfonyl; His, Gln, Asn, Cys: Trityl. For selective disulfide bridge formation, Acm (acetamidomethyl) was also used as a Cys protecting group. For coupling, a four to ten-fold excess of a solution containing Fmoc amino acid, HBTU and DIPEA (1:1:1.1) in DMF was added to swelled resin [HBTU: O-(Benzotriazol-1-yl)-N,N,N',N'-tetramethyluronium hexafluorophosphate; DIPEA: diisopropylethylamine; DMF: dimethylformamide]. HATU (O-(7-azabenzotriazol-1-yl)-1,1,3,3,-tetramethyluronium hexafluorophosphate) was used instead of HBTU to improve coupling efficiency in difficult regions. Fmoc protecting group removal was achieved by treatment with a DMF, piperidine (2:1) solution.

Procedure for Cleavage of Peptides Off Resin

Side chain deprotection and cleavage of the peptides of the invention (e.g., Compound No. 2) was achieved by stirring dry resin in a solution containing trifluoroacetic acid, water, ethanedithiol and tri-isopropylsilane (90:5:2.5:2.5) for 2 to 4 hours. Following TFA removal, peptide was precipitated using ice-cold diethyl ether. The solution was centrifuged and the ether was decanted, followed by a second diethyl ether wash. The peptide was dissolved in an acetonitrile, water solution (1:1) containing 0.1% TFA (trifluoroacetic acid) and the resulting solution was filtered. The linear peptide quality was assessed using electrospray ionisation mass spectrometry (ESI-MS).

Procedure for Purification of Peptides

Purification of the peptides of the invention (e.g., Compound No. 2) was achieved using reverse-phase high performance liquid chromatography (RP-HPLC). Analysis was performed using a C18 column (3 μm, 50×2 mm) with a flow rate of 1 mL/min. Purification of the linear peptides was achieved using preparative RP-HPLC with a C18 column (5 μm, 250×21.2 mm) with a flow rate of 20 mL/min. Separation was achieved using linear gradients of buffer B in A (Buffer A: Aqueous 0.05% TFA; Buffer B: 0.043% TFA, 90% acetonitrile in water).

Procedure for Oxidation of Peptides

Method A (Single disulfide oxidation). Oxidation of the unprotected peptides of the invention (e.g., Compound No. 2) was achieved by adding drop-wise iodine in MeOH (1 mg per 1 mL) to the peptide in a solution (ACN: $H_2O$, 7: 3, 0.5% TFA). After stirring for 2 min, ascorbic acid portion wise was added until the solution was clear and the sample was immediately loaded onto the HPLC for purification.

Method B (Selective oxidation of two disulfides). When more than one disulfide was present (e.g., Compound 30), selective oxidation was often performed. Oxidation of the free cysteines was achieved at pH 7.6 $NH_4CO_3$ solution at 1 mg/10 mL of peptide. After 24 h stirring and prior to purification the solution was acidified to pH 3 with TFA followed by lyophilization. The resulting single oxidized peptides (with ACM protected cysteines) were then oxidized/selective deprotection using iodine solution. The peptide (1 mg per 2 mL) was dissolved in MeOH/$H_2O$, 80:20 iodine dissolved in the reaction solvent was added to the reaction (final concentration: 5 mg/mL) at room temperature. The solution was stirred for 7 minutes before ascorbic acid was added portion wise until the solution is clear. The solution was then loaded directly onto the HPLC.

Method C (Native oxidation). When more than one disulfide was present and when not performing selective oxidations, native oxidation was performed (e.g., this method was used for Compound 19). Native oxidation was achieved with 100 mM $NH_4CO_3$ (pH7.4) solution in the presence of oxidized and reduced glutathione (peptide/GSH/GSSG, 1:100:10 molar ratio) of (peptide: GSSG: GSH, 1:10, 100). After 24 h stirring and prior to RP-HPLC purification the solution was acidified to pH 3 with TFA followed by lyophilization.

Procedure of Cysteine oxidation to produce dimers. Oxidation of the unprotected peptides of the invention (e.g., Compound No. 1) was achieved by adding drop-wise iodine in MeOH (1 mg per 1 mL) to the peptide in a solution (ACN: $H_2O$, 7: 3, 0.5% TFA). After stirring for 2 min, ascorbic acid portion wise was added until the solution was clear and the sample was immediately loaded onto the HPLC for purification.

Procedure for Dimerization. Glyxoylic acid, IDA, or Fmoc-β-Ala-IDA was pre-activated as the N-hydroxysuccinimide ester by treating the acid (1 equiv) with 2.2 eq of both N-hydoxysuccinimide (NHS) and dicyclohexyl carbodiimide (DCC) in NMP (N-methyl pyrolidone) at a 0.1 M final concentration. For the PEG13 and PEG25 linkers, these chemical entities were purchased pre-formed as the activated succinimide ester. The activated ester ~ 0.4 eq was added slowly to the peptide in NMP (1 mg/mL) portionwise. The solution was left stirring for 10 min before 2-3 additional aliquots of the linker ~0.05 eq were slowly added. The solution was left stirring for a further 3 h before the solvent was removed under vaccuo and the residue was purified by reverse phase HPLC. An additional step of stirring the peptide in 20% piperidine in DMF (2×10 min) before an additional reverse phase HPLC purification was performed.

One of skill in the art will appreciate that standard methods of peptide synthesis may be used to generate the compounds of the invention.

Example 2

Activity Assays Methodology

The designed peptides were tested in vitro for induction of degradation of the human ferroportin protein.

The cDNA encoding the human ferroportin (SLC40A1) was cloned from a cDNA clone from Origene (NM_014585). The DNA encoding the ferroportin was amplified by PCR using primers also encoding terminal restriction sites for subcloning, but without the termination codon. The ferroportin receptor was subcloned into a mammalian GFP expression vector containing a neomycin (G418) resistance marker in such that the reading frame of the ferroportin was fused in frame with the GFP protein. The fidelity of the DNA encoding the protein was confirmed by DNA sequencing. HEK293 cells were used for transfection of the ferroportin-GFP receptor expression plasmid. The cells were grown according to standard protocol in growth medium and transfected with the plasmids using Lipofectamine (manufacturer's protocol, Invitrogen). The cells stably expressing ferroportin-GFP were selected using G418 in the growth medium (in that only cells that have taken up and incorporated the cDNA expression plasmid survive) and sorted several times on a Cytomation MoFlo™ cell sorter to obtain the GFP-positive cells (488 nm/530 nm). The cells were propagated and frozen in aliquots.

To determine compound activity on the human ferroportin, the cells were incubated in 96 well plates in standard media, without phenol red. Compound was added to desired final concentration for at least 18 hours in the incubator. Following incubation, the remaining GFP-fluorescence was determined either by whole cell GFP fluorescence (Envision plate reader, 485/535 filter pair), or by Beckman Coulter Quanta™ flow cytometer (express as Geometric mean of fluorescence intensity at 485 nm/525 nm). Compound was added to desired final concentration for at least 18 hours but no more than 24 hours in the incubator.

Reference compounds included native Hepcidin, Mini-Hepcidin, and RI-Mini-Hepcidin, which is an analog of mini-hepcidin. The "RI" in RI-Mini-Hepcidin refers to Retro Inverse. A retro inverse peptide is a peptide with a reversed sequence in all D amino acids. An example is that Hy-Glu-Thr-His-NH2 becomes Hy-DHis-DThr-Dglu-NH2. The EC50 of these reference compounds for ferroportin degradation was determined according to the activity assay described above. These peptides served as control standards for many of the subsequence studies.

TABLE 4

Reference compounds

| Name | Sequence | SEQ ID No. | EC50 (nM) |
|---|---|---|---|
| Hepcidin | Hy-DTHFPIC(1)IFC(2)C(3)GC(2)C(4)HRSK C(3)GMC(4)C(1)KT-OH | 335 | 169 |
| Mini-Hepcidin 1-9 | Hy-DTHFPICIF-NH$_2$ | 336 | 712 |
| RI-Mini Hepcidin | Hy-DPhe-DIle-DCys-DIle-DPro-DPhe-DHis-DThr-DAsp-NH$_2$ | 337 | >10 µM |

To determine whether a given peptide modifies the internalization and degradation of endogenous ferroportin, the protein levels and cellular distribution of ferroportin in hepatocytes and macrophages treated with the peptide may be assayed using Western blotting, immunohistochemistry and ferroportin antibodies known in the art.

Example 3

Cysteine Replacement Scan of Mini-Hepcidin

Previous studies indicate that the N-terminal segment of Hep25 is important for its hepcidin activity and is likely to form the interface with ferroportin. Furthermore, it was thought that Cys in the 7$^{th}$ position is critical for activity. Disulfide bonds can act by structural, catalytic or by functional means. It is postulated that Hepcidin binds to Ferroportin through a disulphide linkage which subsequently internalizes the receptor. A closer inspection of hepcidin reveled that there are 4 disulfides present and that, any one of these cysteine might be responsible for binding to ferroportin. As such, the free thiol of ferroportin possesses a "functional, allosteric bond" equivalent. In order to more thoroughly understand the structure activity relationship with respect to the position of the cysteines within Hepcidin, we performed a cysteine scan up to the 15$^{th}$ residue of a mini-hepcidin peptide and we analyzed the peptides for their ability to exhibit hepcidin activity. Peptides were synthesized using the methods described in Example 1, and their potency for ferroportin degradation was tested as described in Example 2. Results of this study are shown in Table 5, with potency indicated by EC50 values.

TABLE 5

Cysteine replacement scan of Mini-Hepcidin derivatives

| Compound Number | SEQ ID No. | Sequence | EC50 (nM) (n > 3) |
|---|---|---|---|
| 269 | 292 | DTHFPIAIFAAGICI-NH$_2$ | Not active |
| 270 | 293 | DTHFPIAIFAAICI-NH$_2$ | Not active |
| 271 | 294 | DTHFPIAIFAICI-NH$_2$ | Not active |
| 272 | 295 | DTHFPIAIFICI-NH$_2$ | Not active |
| 273 | 296 | DTHFPIAIICI-NH$_2$ | Not active |
| 274 | 297 | DTHFPIAICI-NH$_2$ | Not active |
| 275 | 298 | DTHFPIICI-NH$_2$ | Not active |
| Mini-Hepcidin 1-9 | 336 | Hy-DTHFPICIF-NH$_2$ | 712 nM |
| 1 | 28 | DTHFPCIIF-NH$_2$ | 133 nM |
| 276 | 299 | DTHICIAIF-NH$_2$ | Not active |
| 277 | 300 | DTHCPIAIF-NH$_2$ | Not active |

Inactive = Not active at 30 µM and/or lowest dose

Inactive=Not active at 30 µM and/or lowest dose

Altering the position of the cysteine ablated activity for most of the peptides that were tested; however these data surprisingly demonstrated that Compound 1 is active despite having a Cysteine at the 6$^{th}$, position. FIG. 1 shows a comparison of the dose response curves for Compound 1, as compared to Hepcidin, and the Mini-Hepcidin control. These data clearly demonstrate that Compound 1 has similar in-vitro potency as Hepcidin.

Example 4

Ala Scans of Compound 1 Identified in Cysteine Scan

To validate the results from Example 3, an Ala scan was performed on Compound 1. Peptides were synthesized as described in Example 1, and they were tested for activity as described in Example 2. The results of this study are shown in Table 6. By comparing this result with known structure activity relationships with hepcidin and other mini-hepcidin analogs, we have increased potency. Moreover, these data clearly demonstrate the importance of several residues for activity. Conversely, these date also identify a number of residues that can be modified without ablating activity.

TABLE 6

Alanine scan of Compound 1

| Compound Number | SEQ ID No. | Sequence | EC50 (nM) (n > 3) |
|---|---|---|---|
| 1 | 28 | DTHFPCIIF-NH$_2$ | 133 nM |
| 278 | 301 | DTHFPCIIA-NH$_2$ | >1 µM |

TABLE 6-continued

Alanine scan of Compound 1

| Compound Number | SEQ ID No. | Sequence | EC50 (nM) (n > 3) |
|---|---|---|---|
| 51 | 78 | DTHFPCIAF-NH$_2$ | 382 nM |
| 279 | 302 | DTHFPCAIF-NH$_2$ | >1 µm |
| 280 | 303 | DTHFACIIF-NH$_2$ | >1 µM |
| 282 | 305 | DTHAPCIIF-NH$_2$ | Not active |
| 283 | 306 | DTAFPCIIF-NH$_2$ | 739 nM |
| 52 | 79 | DAHFPCIIF-NH$_2$ | 388 nM |
| 284 | 307 | ATHFPCIIF-NH$_2$ | >1 µM |
| 281 | 304 | DTHF-[(D)-AlA]-CIIF-NH$_2$ | Not active |

Example 5

Analysis of Peptide Activities In Vitro

Based in part on the structure activity relationships (SAR) determined from the results of the experiments described in Examples 3 and 4, a variety of Hepcidin-like peptides of the present invention were synthesized using the method described in Example 1, and in vitro activity was tested as described in Example 2. Reference compounds (shown in Table 4) included native Hepcidin, Mini-Hepcidin, and R1-Mini-Hepcidin. EC50 values of the peptides are shown in summary Table 7.

TABLE 7

In vitro activity of Hepcidin analog peptides

| No. | SEQ ID No. | Sequence | Potency EC$_{50}$ (nM) |
|---|---|---|---|
| 1 | 28 | Hy-DTHFPCIIF-NH$_2$ | 133 |
| 2 | 29 | Isovaleric acid-DTHFPICIFGPRSKGWVC-NH$_2$ | 5 |
| 3 | 30 | Isovaleric acid-DTHFPCIIFGPRSRGWVCK-NH$_2$ | 15 |
| 4 | 31 | Isovaleric acid-DTHFPCIIFGPRSKGWVC-NH$_2$ | 19 |
| 5 | 32 | [Ida]-TH-[Dpa]-[bhPro]-ICIFGPRSKGWVCM-NH$_2$ | 17 |
| 6 | 33 | Isovaleric acid-DTHFPCIFFGPRSKGWVCK-NH$_2$ | 23 |
| 7 | 34 | Isovaleric acid-DTHFPCIIFGPRSKGWTCK-NH$_2$ | 24 |
| 8 | 35 | [Ida]-TH-[Dpa]-[bh-Pro]-CIIFGPRSRGWVCK-NH$_2$ | 29 |
| 9 | 36 | Isovaleric acid-DTHFPCIKFGPRSKGWVCK-NH$_2$ | 32 |
| 10 | 37 | Isovaleric acid-DTHFPCIQFGPRSKGWVCK-NH$_2$ | 35 |
| 11 | 38 | Isovaleric acid-DTHFPCIIFGPRSKGWVCK-NH$_2$ | 9 |
| 12 | 39 | Hy-DTHFPIC$_1$IFVC$_2$GHRSIC$_2$YRRC$_1$R-NH$_2$ | 77 |
| 13 | 40 | Isobutyric acid-DTHFPIC$_1$IFVC$_2$HRSKGC$_2$YRRC$_1$R-NH$_2$ | 63 |
| 14 | 41 | Hy-DTHFPIC$_1$IFVC$_2$HRSKGC$_2$YRAC$_1$-NH$_2$ | 69 |
| 15 | 42 | Isovaleric acid-DTHFPCIEFGPRSKGWVCK-NH$_2$ | 79 |
| 16 | 43 | Hy-DTHFPICIFGPRAKGWVCM-NH$_2$ | 88 |
| 17 | 44 | Isobutyric acid-DTHFPIC$_1$IFVC$_2$HRSKGC$_2$YRRC$_1$R-NH$_2$ | 93 |
| 18 | 45 | Hy-DTHFPICIFGPRSKGWVCM-NH$_2$ | 125 |
| 19 | 46 | Hy-DTHFPIC$_1$IFVC$_2$HRSKGC$_2$YRRC$_1$R-NH$_2$ | 140 |
| 20 | 47 | Hy-DTHFPICIFGPRSRGWVCK-NH$_2$ | 101 |
| 21 | 48 | Hy-DTHFPCIIFGPRSKGWVCM-NH$_2$ | 46 |
| 22 | 49 | Hy-DTHFPICIFAPRSKGWVCM-NH$_2$ | 9430 |
| 23 | 50 | Hy-DTHFPICIFGPRSKGWVCM-OH | 131 |

TABLE 7-continued

In vitro activity of Hepcidin analog peptides

| No. | SEQ ID No. | Sequence | Potency $EC_{50}$ (nM) |
|---|---|---|---|
| 24 | 51 | Hy-DTHFPCIQF-$NH_2$ | 138 |
| 25 | 52 | Hy-DTHFPIC$_1$IFVC$_2$GHRSKGC$_2$YRRC$_1$R-$NH_2$ | 144 |
| 26 | 53 | Hy-DTHFAICIFGPRSKGWVCM-$NH_2$ | 147 |
| 27 | 54 | Hy-DTHFPICIFGPHRSKGWVCM-$NH_2$ | 149 |
| 28 | 55 | Hy-DTHFPICIFGPRAKGWVCM-$NH_2$ | 88 |
| 29 | 56 | Hy-DTHFPACIFGPRSKGWVCM-$NH_2$ | 157 |
| 30 | 57 | Hy-DTHFPC$_1$IIFVC$_2$HRPKGC$_2$YRRVC$_1$R-$NH_2$ | 173 |
| 31 | 58 | Hy-DTHFPICIFGPRSKAWVCM-$NH_2$ | 175 |
| 32 | 59 | Hy-DTHFPIC$_1$IFVC$_2$GHRGKGC$_2$YRRC$_1$R-$NH_2$ | 182 |
| 33 | 60 | Hy-ATHFPICIFGPRSKGWVCM-$NH_2$ | 184 |
| 34 | 61 | Hy-DTHFPICIFGPASKGWVCM-$NH_2$ | 206 |
| 35 | 62 | Hy-DTHFPIC$_1$IFVC$_2$HRSKGC$_2$YARC$_1$-$NH_2$ | 214 |
| 36 | 63 | Ac-DTHFPICIFGPRSKGWVCM-$NH_2$ | 239 |
| 37 | 64 | Hy-DTHFPICIFGPRSAGWVCM-$NH_2$ | 239 |
| 38 | 65 | Hy-DTHAPICIFGPRSKGWVCM-$NH_2$ | 254 |
| 39 | 66 | Hy-DTHFPIC$_1$IFVC$_2$HRSKGC$_2$YRRC$_1$-$NH_2$ | 256 |
| 40 | 67 | pGlu-THFPIC$_1$IFVC$_2$HRSKGC$_2$YRRC$_1$R-$NH_2$ | 260 |
| 41 | 68 | Ac-DTHFPICIFKPRSKGWVCM-$NH_2$ | 262 |
| 42 | 69 | Hy-DTHFPIC$_1$IFVC$_2$GHRSKGC$_2$YMRC$_1$KT-$NH_2$ | 265 |
| 43 | 70 | Hy-DAHFPICIFGPRSKGWVCM-$NH_2$ | 265 |
| 44 | 71 | Hy-DTHFPIC$_1$IFVC$_2$YRGIC$_2$YRRC$_1$R-$NH_2$ | 269 |
| 45 | 72 | Ac-DTHFPICIFGPRSKGWVCM-$NH_2$ | 272 |
| 46 | 73 | Hy-[bhAsp]-THFPICIFGPRSKGWVC-$NH_2$ | 274 |
| 47 | 74 | Hy-DTHFPICIFGPRSKGWACM-$NH_2$ | 313 |
| 48 | 75 | [Ida]-TH-[Dpa]-[bhPro]-RCR-[bhPhe]-GPRSKGWVCM-$NH_2$ | 331 |
| 49 | 76 | Hy-DTHFPCIRF-$NH_2$ | 334 |
| 50 | 77 | Isovaleric acid-THFPCIIFGPRSKGWVCM-$NH_2$ | 345 |
| 51 | 78 | Hy-DTHFPCIAF-$NH_2$ | 382 |
| 52 | 79 | Hy-DAHFPCIIF-$NH_2$ | 388 |
| 53 | 80 | Hy-DTHFPIC$_1$IFVC$_2$HRPKGC$_2$YRRC$_1$P-$NH_2$ | 393 |
| 54 | 81 | Ac-DTHFPICIFKPRS-K(PEG8)-GWVCM-$NH_2$ | 479 |
| 55 | 82 | Hy-DTHFPCIIFK-$NH_2$ | 419 |
| 56 | 83 | Hy-DTHFPCIFF-$NH_2$ | 441 |
| 57 | 84 | Hy-DTHFPICIFGPRSK-K(PEG8)-WVCM-$NH_2$ | 462 |
| 58 | 85 | Ac-DTHFPICIFGPRSKKWVCM-$NH_2$ | 472 |
| 59 | 86 | Hy-DTHFPIC$_1$IFC$_2$PWGMC$_2$C$_1$K-$NH_2$ | 495 |
| 60 | 87 | Hy-DTAFPICIFGPRSKGWVCM-$NH_2$ | 498 |
| 65 | 88 | Hy-DTHFPIC$_1$IFVC$_2$YRGIC$_1$YMRC$_2$KT-$NH_2$ | 763 |

TABLE 7-continued

In vitro activity of Hepcidin analog peptides

| No. | SEQ ID No. | Sequence | Potency EC$_{50}$ (nM) |
|---|---|---|---|
| 66 | 89 | Hy-DTHFPICIFGPRSKGAVCM-NH$_2$ | 520 |
| 67 | 90 | Hy-DTHFPICIAGPRSKGWVCM-NH$_2$ | 2466 |
| 68 | 91 | Hy-DTHFPICAFGPRSKGWVCM-NH$_2$ | >10 µM |
| 69 | 92 | Hy-DTHFPIAIFGPRSKGWVAM-NH$_2$ | Inactive |
| 70 | 93 | Hy-DTHFPCRRFGPRSKGWVC-NH$_2$ | Inactive |
| 71 | 94 | [Ida]-THF-[bh-Pro]-CRR-[bh-Phe]-GPRSKGWVC-NH$_2$ | N/A |
| 73 | 96 | Hy-DTHFPC$_1$IIFVC$_2$HRSKGC$_2$YWAVC$_1$-NH$_2$ | 2640 |
| 74 | 97 | Hy-DTHFP-(D)Cys$_1$-IIFVC$_2$HRSKGC$_2$YWAV-(D)Cys$_1$-F-NH$_2$ | 356 |
| 75 | 98 | Hy-DTHFPC$_1$IIFVC$_2$HRSKGC$_2$YWAVC$_1$FW-NH$_2$ | Not Tested |
| 76 | 99 | Ac-DTHFPICIF-K(PEG8)-PRSKGWVCM-NH$_2$ | 610 |
| 78 | 101 | Hy-DTH-[Dpa]-PCIIFGPRSRGWVCK-NH$_2$ | >1 µM |
| 79 | 102 | Hy-DTHF[bh-Pro]-CIIFGPRSRGWVCK-NH$_2$ | >1 µM |
| 80 | 103 | Hy-DTHFPCIIFGPRSRGWRCK-NH$_2$ | >1 µM |
| 81 | 104 | Hy-DTHFPCIRFGPRSRGWVCK-NH$_2$ | >1 µM |
| 82 | 105 | Hy-DTHFPCIRFGPRSRGWRCK-NH$_2$ | >1 µM |
| 83 | 106 | Hy-DTHFPCIIFGPRSRGWVCK-NH$_2$ | >1 µM |
| 84 | 107 | Hy-DTHFPCIIFGPRSRGVCK-NH$_2$ | >1 µM |
| 85 | 108 | Hy-DTHFPCIYFGPRSKGWVCK-NH$_2$ | 705 |
| 86 | 109 | Hy-DTHFPCIIFGPRSKGWVCK-NH$_2$ | >1 µM |
| 87 | 110 | Hy-DTHFPCIIFGPRARGWVCK-NH$_2$ | >1 µM |
| 88 | 111 | Octanoic acid-DTHFPCIIFGPRSRGWVCK-NH$_2$ | >1 µM |
| 89 | 112 | Palm-PEG11-DTHFPCIIFGPRSRGWVCK-NH$_2$ | >1 µM |
| 90 | 113 | Ac-DTHFPICIF-K(2K PEG)-PRSKGWVCK-NH$_2$ | 107 |
| 91 | 114 | Hy-DTHFPCIIFGPRSKGWKCK-NH$_2$ | Not Tested |
| 92 | 115 | Hy-DTHFPCIKFGPRSKGWKCK-NH$_2$ | Not Tested |
| 93 | 116 | Isovaleric acid-DTHFPCLIFGPRSKGWVCK-NH$_2$ | 19 |
| 94 | 117 | Isovaleric acid-DTHFPCVIFGPRSKGWVCK-NH$_2$ | 41 |
| 95 | 118 | Isovaleric acid-DTHFPCSIFGPRSKGWVCK-NH$_2$ | 78 |
| 96 | 119 | Isovaleric acid-DTHFPCQIFGPRSKGWVCK-NH$_2$ | 157 |
| 97 | 120 | Hy-THFPCIIFGPRSKGWVCK-NH$_2$ | Inactive |
| 98 | 121 | Isovaleric acid-THFPCIIFGPRSKGWVCK-NH$_2$ | Inactive |
| 99 | 122 | Hy-HFPCIIFGPRSKGWVCK-NH$_2$ | Inactive |
| 100 | 123 | Isovaleric acid-HFPCIIFGPRSKGWVCK-NH$_2$ | Inactive |
| 101 | 124 | Hy-DTHFPCISFGPRSKGWVCK-NH$_2$ | >1 µM |
| 102 | 125 | Hy-DTHFPCIKFGPRSKGWVCK-NH$_2$ | >1 µM |
| 103 | 126 | Hy-EDTHFPCIIFGPRSKGWVCK-NH$_2$ | >1 µM |
| 105 | 128 | Isovaleric acid-DTHFPCIIFEPRSKGWVCK-NH$_2$ | 10 |

TABLE 7-continued

In vitro activity of Hepcidin analog peptides

| No. | SEQ ID No. | Sequence | Potency EC$_{50}$ (nM) |
|---|---|---|---|
| 106 | 129 | Isovaleric acid-DTHFPCIIFSPRSKGWVCK-NH$_2$ | 44 |
| 107 | 130 | Isovaleric acid-DTHFSCIIFGPRSKGWVCK-NH$_2$ | 50 |
| 108 | 131 | Octanoic acid-PEG11-DTHFPCIIFGPRSRGWVCK-NH$_2$ | >1 µM |
| 109 | 132 | Isobutyric acid-PEG11-DTHFPCIIFGPRSRGWVCK-NH$_2$ | >1 µM |
| 110 | 133 | [Ida]-THFPCIIFGPRSRGWVCK-NH$_2$ | >300 nM |
| 111 | 134 | Isovaleric acid-DTHFPCIIFGPKSKGWVCK-NH$_2$ | 12 |
| 112 | 135 | Isovaleric acid-DTHFPCIKFGPKSKGWVCK-NH$_2$ | 15 |
| 113 | 136 | Isovaleric acid-DTHFPCIIFGPRSKGWCK-NH$_2$ | 15 |
| 114 | 137 | Isovaleric acid-DTHFPCIIFGPRSKGVC-NH$_2$ | 18 |
| 115 | 138 | Isovaleric acid-DTHFPCIIFGPRSKGCK-NH$_2$ | 21 |
| 117 | 140 | Isovaleric acid-DTHFPC-[Dapa]-IFGPRSKGWDCK-NH$_2$ | 65 |
| 118 | 141 | Isovaleric acid-DTHFPCI-[Dapa]-FGPRSKGWDCK-NH$_2$ | 17 |
| 119 | 142 | Isovaleric acid-DTHFPC-[Dapa]-IFGPRSKGWECK-NH$_2$ | 151 |
| 120 | 143 | Isovaleric acid-DTHFPCI-[Dapa]-FGPRSKGWECK-NH$_2$ | 15 |
| 121 | 144 | Isovaleric acid-DTHFPCIKFGPRSKGWECK-NH$_2$ | 14 |
| 122 | 145 | Isovaleric acid-DTHFGCIIFGPRSKGWVCK-NH$_2$ | 57 |
| 123 | 146 | Hy-DTHFGCIIFGPRSKGWVCK-NH$_2$ | Inactive |
| 124 | 147 | Isovaleric acid-DTHFRCIIFGPRSKGWVCK-NH$_2$ | 106 |
| 125 | 148 | Hy-DTHFRCIIFGPRSKGWVCK-NH$_2$ | Inactive |
| 126 | 149 | Isovaleric acid-DTHF-[Sarc]-CIIFGPRSKGWVCK-NH$_2$ | 31 |
| 127 | 150 | Hy-DTHF-[Sarc]-CIIFGPRSKGWVCK-NH$_2$ | Inactive |
| 128 | 151 | Isovaleric acid-DTHF-[+62-Ala]-CIIFGPRSKGWVCK-NH$_2$ | 264 |
| 129 | 152 | Hy-DTHF-[+62-Ala]-CIIFGPRSKGWVCK-NH$_2$ | Inactive |
| 130 | 153 | Isovaleric acid-DTHFKCIIFGPRSKGWVCK-NH$_2$ | 150 |
| 131 | 154 | Hy-DTHFKCIIFGPRSKGWVCK-NH$_2$ | Inactive |
| 132 | 155 | Hy-THFPCIIFGPRSKGWVCM-NH$_2$ | >1 µM |
| 133 | 156 | Hy-HFPCIIFGPRSKGWVCM-NH$_2$ | >1 µM |
| 134 | 157 | Isovaleric acid-HFPCIIFGPRSKGWVCM-NH$_2$ | >1 µM |
| 135 | 158 | Hy-DTHFPCISFGPRSKGWVCM-NH$_2$ | 545 |
| 136 | 159 | Hy-DTHFPCIKFGPRSKGWVCM-NH$_2$ | 669 |
| 137 | 160 | Hy-EDTHFPCIIFGPRSKGWVCM-NH$_2$ | 873 |
| 139 | 162 | Hy-DTHFPCIIFEPRSKGWVCM-NH$_2$ | N/A |
| 140 | 163 | Isovaleric acid-DTHFKCIEFGPRSKGWVCK-NH$_2$ | >1 µM |
| 141 | 164 | Isovaleric acid-DTHFPCIIFGPRSKGWACK-NH$_2$ | 11 |
| 142 | 165 | Isovaleric acid-DTHFPCIIFEPRSKGWVCK-NH$_2$ | 9 |
| 143 | 166 | Isovaleric acid-DTHFPCIIFGPRSKGWVCKKKK-NH$_2$ | 24 |
| 144 | 167 | Isovaleric acid-DTHFPCIIFEPRSKGWVCKKKK-NH$_2$ | 15 |
| 145 | 168 | Isovaleric acid-DTHFPCIIFGPRSKGWVCKK-NH$_2$ | 9 |

TABLE 7-continued

In vitro activity of Hepcidin analog peptides

| No. | SEQ ID No. | Sequence | Potency EC$_{50}$ (nM) |
|---|---|---|---|
| 146 | 169 | Isovaleric acid-DTAFPCIIFGPRSKGWVCK-NH$_2$ | 24 |
| 147 | 170 | Isovaleric acid-DTKFPCIIFGPRSKGWVCK-NH$_2$ | 20 |
| 148 | 171 | Isovaleric acid-DTHFPC$_1$IIFVC$_2$HRPKGC$_2$YRRVC$_1$R-NH$_2$ | 2.2 |
| 149 | 172 | Isovaleric acid-DTHFPCI-K(PEG8)-FGPRSKGWVCK-NH$_2$ | 9 |
| 150 | 173 | Isovaleric acid-DTHFPCIKF-K(PEG8)-PRSKGWVCK-NH$_2$ | 7 |
| 151 | 174 | Isovaleric acid-DTHFPCIKFGP-K(PEG8)-SKGWVCK-NH$_2$ | 13 |
| 152 | 175 | Isovaleric acid-DTHFPCIKFGPRS-K(PEG8)-GWVCK-NH$_2$ | 16 |
| 153 | 176 | Isovaleric acid-DTHFPCIKFGPRSKGWVC-K(PEG8)-NH$_2$ | 18 |
| 154 | 177 | Isovaleric acid-DTHFPCIKFGPRSKGWTCK-NH$_2$ | 18 |
| 155 | 178 | Isovaleric acid-DTHFPCIEFGPRSKGWTCK-NH$_2$ | 38 |
| 156 | 179 | Isovaleric acid-DTHFPICIFGPRS-K(Betaine)-GWVC-NH$_2$ | Not Tested |
| 157 | 180 | Isovaleric acid-DTHFPCIKFGPRS-K(Betaine)-GWVCK-NH$_2$ | 18 |
| 158 | 181 | Isovaleric acid-DTHFPCI-K(Betaine)-FGPRSKGWVCK-NH$_2$ | 16 |
| 159 | 182 | Isovaleric acid-DTHFPCIKFGPRSKGWVC-K(Betaine)-NH$_2$ | 17 |
| 160 | 183 | Ac-DTHFPCIKFGPRSKGWVCK-NH$_2$ | 464 |
| 161 | 184 | Isovaleric acid-PEG3-DTHFPCIKFGPRSKGWVCK-NH$_2$ | 666 |
| 162 | 185 | Isobutyric acid-DTHFPCIKFGPRSKGWVCK-NH$_2$ | 41 |
| 163 | 186 | Valeric acid-DTHFPCIKFGPRSKGWVCK-NH$_2$ | 64 |
| 164 | 187 | Hy-VDTHFPCIKFGPRSKGWVCK-NH$_2$ | 146 |
| 165 | 188 | Hy-LDTHFPCIKFGPRSKGWVCK-NH$_2$ | 107 |
| 166 | 189 | Hexanoic acid-DTHFPCIKFGPRSKGWVCK-NH$_2$ | 36 |
| 167 | 190 | 5-Methylpentanoic acid-DTHFPCIKFGPRSKGWVCK-NH$_2$ | 99 |
| 168 | 191 | Cyclohexanoic acid-DTHFPCIKFGPRSKGWVCK-NH$_2$ | 30 |
| 169 | 192 | Heptanoic acid-DTHFPCIKFGPRSKGWVCK-NH$_2$ | 91 |
| 170 | 193 | Octanoic acid-DTHFPCIKFGPRSKGWVCK-NH$_2$ | 183 |
| 171 | 194 | Isovaleric acid-DTHFPCIIFGPRSKGWKCK-NH$_2$ | 48 |
| 172 | 195 | Isovaleric acid-DTHFPCIIFGPRSKGWECK-NH$_2$ | 15 |
| 173 | 196 | Isovaleric acid-DTHFPCRRFGPRSKGWVCK-NH$_2$ | Not Tested |
| 176 | 199 | Isovaleric acid-DTHFPICIFGPRS-K(PEG8)-GWVC-NH$_2$ | 6 |
| 177 | 200 | Isovaleric acid-DTHFPICIFGPRS-K(PEG4)-GWVC-NH$_2$ | 6 |
| 178 | 201 | Isovaleric acid-DTHFPCIIFGPRSRGWVC-K(PEG8)-NH$_2$ | 3 |
| 179 | 202 | Isovaleric acid-DTHFPCIIFGPRSRGWVC-K(PEG4)-NH$_2$ | 4 |
| 180 | 203 | Isovaleric acid-DTHFPCIIFGPRSRGWVC-K(PEG2)-NH$_2$ | 9 |
| 181 | 204 | Isovaleric acid-DTHFPCIKFEPRSKGWVCK-NH$_2$ | 15 |
| 182 | 205 | Isovaleric acid-DTHFPCIKFEPRSKGWTCK-NH$_2$ | 13 |
| 183 | 206 | Isovaleric acid-DTHFPCIKFEPRSKGWCK-NH$_2$ | 17 |
| 184 | 207 | Isovaleric acid-DTHFPCIKFEPRSKGCK-NH$_2$ | 23 |

TABLE 7-continued

In vitro activity of Hepcidin analog peptides

| No. | SEQ ID No. | Sequence | Potency EC$_{50}$ (nM) |
|---|---|---|---|
| 185 | 208 | Isovaleric acid-DTHFPCIFEPRSKGCK-NH$_2$ | 54 |
| 186 | 209 | Isovaleric acid-DTHFPCIFEPRSKGWCK-NH$_2$ | 12 |
| 187 | 210 | Isovaleric acid-DTHFPCIKFGPRSKCK-NH$_2$ | 21 |
| 188 | 211 | Isovaleric acid-DTHFPCIKFGPRSCK-NH$_2$ | 30 |
| 189 | 212 | Isovaleric acid-DTHFPCIKFGPRCK-NH$_2$ | 36 |
| 190 | 213 | Isovaleric acid-DTHFPCIKFGPCK-NH$_2$ | 55 |
| 191 | 214 | Isovaleric acid-DTHFPCIKFGCK-NH$_2$ | 97 |
| 192 | 215 | Isovaleric acid-DTHFPCIKFCK-NH$_2$ | 48 |
| 193 | 216 | Isovaleric acid-DTHFPCIKFC-NH$_2$ | 80 |
| 194 | 217 | Isovaleric acid-DTHFPCI-K(Palm)-FGPRSKGWVCK-NH$_2$ | 4 |
| 195 | 218 | Isovaleric acid-DTHFPCIKF-K(Palm)-PRSKGWVCK-NH$_2$ | 9 |
| 196 | 219 | Isovaleric acid-DTHFPCIKFGP-K(Palm)-SKGWVCK-NH$_2$ | 2 |
| 197 | 220 | Isovaleric acid-DTHFPCIKFGPRS-K(Palm)-GWVCK-NH$_2$ | 1 |
| 198 | 221 | Isovaleric acid-DTHFPCIKFGPRSKGWVC-K(Palm)-NH$_2$ | 7 |
| 199 | 222 | Isovaleric acid-DTHFPCI-K(PEG3-Palm)-FGPRSKGWVCK-NH$_2$ | 7 |
| 200 | 223 | Isovaleric acid-DTHFPCIKF-K(PEG3-Palm)-PRSKGWVCK-NH$_2$ | 6 |
| 201 | 224 | Isovaleric acid-DTHFPCIKFGP-K(PEG3-Palm)-SKGWVCK-NH$_2$ | 4 |
| 202 | 225 | Isovaleric acid-DTHFPCIKFGPRS-K(PEG3-Palm)-GWVCK-NH$_2$ | 3 |
| 203 | 226 | Isovaleric acid-DTHFPCIKFGPRSKGWVC-K(PEG3-Palm)-NH$_2$ | 4 |
| 204 | 227 | Hy-DTHFPCI-K(IVA)-FGPRSKGWVCK-NH$_2$ | >300 nM |
| 205 | 228 | Hy-DTHFPCIKF-K(IVA)-PRSKGWVCK-NH$_2$ | >300 nM |
| 206 | 229 | Hy-DTHFPCIKFGP-K(IVA)-SKGWVCK-NH$_2$ | 624 |
| 207 | 230 | Hy-DTHFPCIKFGPRS-K(IVA)-GWVCK-NH$_2$ | 318 |
| 208 | 231 | Hy-DTHFPCIKFGPRSKGWVC-K(IVA)-NH$_2$ | 109 |
| 209 | 232 | Hy-DTHFPCI-K(PEG3-IVA)-FGPRSKGWVCK-NH$_2$ | 342 |
| 210 | 233 | Hy-DTHFPCIKF-K(PEG3-IVA)-PRSKGWVCK-NH$_2$ | 457 |
| 211 | 234 | Hy-DTHFPCIKFGP-K(PEG3-IVA)-SKGWVCK-NH$_2$ | >300 nM |
| 212 | 235 | Hy-DTHFPCIKFGPRS-K(PEG3-IVA)-GWVCK-NH$_2$ | >300 nM |
| 213 | 236 | Hy-DTHFPCIKFGPRSKGWVC-K(PEG3-IVA)-NH$_2$ | 233 |
| 214 | 237 | Isovaleric acid-DTHFPCIKFEPRSKKWVCK-NH$_2$ | 15 |
| 215 | 238 | Hy-DTHFPCIKFGPRSKGWVCK-NH$_2$ | >1 µM |
| 216 | 239 | Palm-DTHFPCIKFGPRSKGWVCK-NH$_2$ | >1 µM |
| 217 | 240 | Palm-PEG3-DTHFPCIKFGPRSKGWVCK-NH$_2$ | >1 µM |
| 218 | 241 | Isovaleric acid-DTHFPCI-K(isoglu-Palm)-FEPRSKGCK-NH$_2$ | 10 |
| 219 | 242 | Isovaleric acid-DTHFPCIKF-K(isoglu-Palm)-PRSKGCK-NH$_2$ | 9 |
| 220 | 243 | Isovaleric acid-DTHFPCIKFEP-K(isoglu-Palm)-SKGCK-NH$_2$ | 5 |
| 221 | 244 | Isovaleric acid-DTHFPCIKFEPRS-K(isoglu-Palm)-GCK-NH$_2$ | 4 |
| 222 | 245 | Isovaleric acid-DTHFPCIKFEPRSK-K(isoglu-Palm)-CK-NH$_2$ | 4 |

TABLE 7-continued

In vitro activity of Hepcidin analog peptides

| No. | SEQ ID No. | Sequence | Potency EC$_{50}$ (nM) |
|---|---|---|---|
| 223 | 246 | Isovaleric acid-DTHFPCIKFEPRSKGC-K(isoglu-Palm)-NH$_2$ | 5 |
| 224 | 247 | Isovaleric acid-DTHFPCIKFEPRSKGCK-K(isoglu-Palm)-NH$_2$ | 4 |
| 225 | 248 | Isovaleric acid-DTHFPCI-K(dapa-Palm)-FEPRSKGCK-NH$_2$ | 17 |
| 226 | 249 | Isovaleric acid-DTHFPCIKF-K(dapa-Palm)-PRSKGCK-NH$_2$ | 14 |
| 227 | 250 | Isovaleric acid-DTHFPCIKFEP-K(dapa-Palm)-SKGCK-NH$_2$ | 10 |
| 228 | 251 | Isovaleric acid-DTHFPCIKFEPRS-K(dapa-Palm)-GCK-NH$_2$ | 7 |
| 229 | 252 | Isovaleric acid-DTHFPCIKFEPRSK-K(dapa-Palm)-CK-NH$_2$ | 13 |
| 230 | 253 | Isovaleric acid-DTHFPCIKFEPRSKGC-K(dapa-Palm)-K-NH$_2$ | 10 |
| 231 | 254 | Isovaleric acid-DTHFPCIKFEPRSKGCK-K(dapa-Palm)-NH$_2$ | 11 |
| 232 | 255 | Isovaleric acid-DTHFPCIKFGPRSKGWVCK-NH$_2$ | Not Tested |
| 233 | 256 | Isovaleric acid-AAHFPCIKFGPRSKGWVCK-NH$_2$ | 320 |
| 234 | 257 | Isovaleric acid-ATHFPCIKFGPRSKGWVCK-NH$_2$ | 60 |
| 235 | 258 | Isovaleric acid-DAHFPCIKFGPRSKGWVCK-NH$_2$ | 203 |
| 236 | 259 | Isovaleric acid-DTHAPCIKFGPRSKGWVCK-NH$_2$ | >500 nM |
| 237 | 260 | Isovaleric acid-DTHFPCIKAGPRSKGWVCK-NH$_2$ | 50 |
| 238 | 261 | Isovaleric acid-DTHFPCIKFEPRSKGWVCK-OH | 47 |
| 239 | 262 | Isovaleric acid-DTHFPCIKFEPRSKGWECK-OH | 101 |
| 240 | 263 | Isovaleric acid-DTHFPCIIFEPRSKGWEC-OH | 139 |
| 241 | 264 | Isovaleric acid-DTHFPCIKFK(isoGlu-Palm)-PRSKGWECK-NH$_2$ | 6 |
| 242 | 265 | Isovaleric acid-DTHFPCIKFEPK(isoGlu-Palm)-SKGWECK-NH$_2$ | 8 |
| 243 | 266 | Isovaleric acid-DTHAPCIKFEPRSKGWECK-NH$_2$ | Inactive |
| 244 | 267 | Ida-THFPCIKFEPRSK-K(isoGlu-Palm)CK-NH$_2$ | 25 |
| 245 | 268 | Isovaleric acid-DTHFPCI-K(isoGlu-Palm)-FEPRSKGWEC-OH | 131 |
| 246 | 269 | 4,4-5,5-6,6,6-Heptafluorohexanoic acid-DTHFPCIKFGPRSKGWVCK-NH$_2$ | 480 |
| 247 | 270 | Isovaleric acid-DTHFPCIKF-K(mysteric acid)-PRSKGWVC-NH$_2$ | 7 |
| 248 | 271 | Isovaleric acid-DTHFPCIKF-K(lauric acid)-PRSKGWVC-NH$_2$ | 10 |
| 249 | 272 | Isovaleric acid-DTHFPCIKF-K(decanoic acid)-PRSKGWVC-NH$_2$ | 22 |
| 250 | 273 | Isovaleric acid-DTHFPCIKF-K(octanoic acid)-PRSKGWVC-NH$_2$ | 30 |
| 251 | 274 | Isovaleric acid-DTHFPCIKF-K(hexanoic acid)-PRSKGWVC-NH$_2$ | 21 |
| 252 | 275 | Isovaleric acid-DTHFPCIKF-K(butyric acid)-PRSKGWVC-NH$_2$ | 37 |
| 253 | 276 | Isovaleric acid-DTHFPCIKF-K(Ac)-PRSKGWVC-NH$_2$ | 29 |
| 254 | 277 | Ida-THFPCIKFEPRSKGWVC-K(mysteric acid)-NH$_2$ | 20 |
| 255 | 278 | [Ida]-THFPCIKFEPRSKGWVC-K(lauric acid)-NH$_2$ | 52 |
| 256 | 279 | [Ida]-THFPCIKFEPRSKGWVC-K(decanoic acid)-NH$_2$ | 116 |

TABLE 7-continued

In vitro activity of Hepcidin analog peptides

| No. | SEQ ID No. | Sequence | Potency EC$_{50}$ (nM) |
|---|---|---|---|
| 257 | 280 | [Ida]-THFPCIKFEPRSKGWVC-K(octanoic acid)-NH$_2$ | 129 |
| 258 | 281 | [Ida]-THFPCIKFEPRSKGWVC-K(hexanoic acid)-NH$_2$ | 191 |
| 259 | 282 | [Ida]-THFPCIKFEPRSKGWVC-K(butyric acid)-NH$_2$ | 355 |
| 260 | 283 | [Ida]-THFPCIKFEPRSKGWVC-K(Ac)-N+562 | 502 |
| 261 | 284 | Isovaleric acid-HFPCIKFEPRSKGWVC-K(octanoic acid)-NH$_2$ | >300 nM |
| 262 | 285 | Isovaleric acid-HFPCIKFEPRSKGWVC-K(lauric acid)-NH$_2$ | 77 |
| 263 | 286 | Isovaleric acid-DTHFPCIKFEPHSKGCK-NH$_2$ | 62 |
| 264 | 287 | Isovaleric acid-DTHFPCIHFEPHSKGC-NH$_2$ | 118 |
| 265 | 288 | Isovaleric acid-DTHFPCIKFEPHS-K(Albu)-GCK-NH$_2$ | 6 |
| 266 | 289 | Isovaleric acid-DTHFPCIKFEPREKEC-NH$_2$ | 183 |
| 267 | 290 | Isovaleric acid-DTAFPCIKFEPRSKEC-NH$_2$ | >1 µM |
| 268 | 291 | Isovaleric acid-DTHFPCIKFECK-NH$_2$ | 107 |
| 269 | 292 | Hy-DTHFPIAIFAAGICI-NH$_2$ | Inactive |
| 270 | 293 | Hy-DTHFPIAIFAAICI-NH$_2$ | Inactive |
| 271 | 294 | Hy-DTHFPIAIFAICI-NH$_2$ | Inactive |
| 272 | 295 | Hy-DTHFPIAIFICI-NH$_2$ | Inactive |
| 273 | 296 | Hy-DTHFPIAIICI-NH$_2$ | Inactive |
| 274 | 297 | Hy-DTHFPIAICI-NH$_2$ | Inactive |
| 275 | 298 | Hy-DTHFPIICI-NH$_2$ | Inactive |
| 276 | 299 | Hy-DTHICIAIF-NH$_2$ | Inactive |
| 277 | 300 | Hy-DTHCPIAIF-NH$_2$ | Inactive |
| 278 | 301 | Hy-DTHFPCIIA-NH$_2$ | >1 µM |
| 279 | 302 | Hy-DTHFPCAIF-NH$_2$ | >1 µM |
| 280 | 303 | Hy-DTHFACIIF-NH$_2$ | >1 µM |
| 281 | 304 | Hy-DTHF-(D)--Ala-CIIF-NH$_2$ | Inactive |
| 282 | 305 | Hy-DTHAPCIIF-NH$_2$ | Inactive |
| 283 | 306 | Hy-DTAFPCIIF-NH$_2$ | 739 nM |
| 284 | 307 | Hy-ATHFPCIIF-NH$_2$ | >1 µM |
| 285 | 308 | [Ida]-THF-[bh-Pro]-CIIF-NH$_2$ | >1 µM |
| 287 | 310 | Hy-DTHFPCIEF-NH$_2$ | >1 µM |
| 288 | 311 | Isovaleric acid-DTHFPCIIF-NH$_2$ | 16 nM |
| 289 | 312 | Isovaleric acid-DTHFPAIIF-NH$_2$ | Inactive |
| 290 | 313 | Isovaleric acid-DTHFPSIIF-NH$_2$ | Inactive |
| 291 | 314 | Isovaleric acid-DTHFPCIKF-NH$_2$ | 7 nM |
| 293 | 316 | Hy-DTHFPCIF-NH$_2$ | 52% at 1 µM |
| 297 | 320 | Hy-DTHFPCIKFF-NH$_2$ | 64% at 1 µM |
| 298 | 321 | Hy-YTHFPCIIF-NH$_2$ | Not Tested |

TABLE 7-continued

In vitro activity of Hepcidin analog peptides

| No. | SEQ ID No. | Sequence | Potency EC$_{50}$ (nM) |
|---|---|---|---|
| 299 | 322 | Hy-LTHFPCIIF-NH$_2$ | 64% at 1 µM |
| 300 | 323 | Hy-ETHFPCIIF-NH$_2$ | 77% at 1 µM |
| 301 | 324 | Hy-DRHFPCIIF-NH$_2$ | Not Tested |
| 302 | 325 | Hy-DTKFPCIIF-NH$_2$ | 60% at 1 µM |
| 303 | 326 | Hy-DTHFECIIF-NH$_2$ | Not Tested |
| 304 | 327 | Hy-DTHFPCIIK-NH$_2$ | 55% at 1 µM |
| 305 | 328 | Hy-DTHFPCIIR-NH$_2$ | 62% at 1 µM |
| 306 | 329 | Hy-DTHFPCIEF-NH$_2$ | Not Tested |
| 307 | 330 | Hy-DTHFPCIVF-NH$_2$ | 75% at 1 µM |
| 308 | 331 | Hy-DTHFPCILF-NH$_2$ | 89% at 1 µM |
| 309 | 332 | Hy-DTHFPCILK-NH$_2$ | 55% at 1 µM |
| 310 | 333 | Hy-DTHFPCIEK-NH$_2$ | 0% at 1 µM |
| 355 | 369 | Isovaleric acid-DTHFPCIKFEPRSKECK-NH$_2$ | 48 |
| 356 | 370 | Isovaleric acid-DTHFPCIKFEPHSKECK-NH$_2$ | 181 |
| 357 | 371 | Isovaleric acid-DTHFPCIKKEPHSKECK-NH$_2$ | >1 µM |
| 358 | 372 | Isovaleric acid-DTHFPCIKF-K(isoglu-Palm)-PHSKECK-NH$_2$ | 6 |
| 359 | 373 | Isovaleric acid-DTHFPCIKFEPRECK-NH$_2$ | 64 |
| 360 | 374 | Isovaleric acid-DTHFPCIKFEPHECK-NH$_2$ | 138 |
| 361 | 375 | Isovaleric acid-DTHFPCIKFEPRCK-NH$_2$ | 29 |

Inactive = Not active at 30 µM and/or lowest dose.
For Table 7, parentheticals, e.g., (_), represent side chain conjugations and brackets, e.g., [ ], represent unnatural amino acid substitutions.

For certain compounds comprising an N-terminal PEG11 moiety (e.g., compounds 89, 108, and 109), the following was used in their synthesis:

Fmoc-Amino PEG Propionic Acid

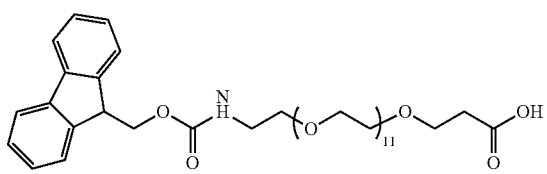

Example 6

Alanine Scan of Compound 18

To further understand Hepcidin's structure activity relationship, an alanine scan was performed on Compound 18, which is a Hepcidin analogue of the present invention that comprises a cysteine in the 7 position. Peptides were synthesized as described in Example 1 and tested for activity as described in Example 2; results are shown in Table 8 herein.

TABLE 8

Alanine scan of Coupound 18

| Compound Number | SEQ ID No. | Sequence | EC50 (nM) (n > 3) |
|---|---|---|---|
| 18 | 45 | DTHFPICIFGPRSKGWVCM-NH$_2$ | 125 |
| 47 | 74 | DTHFPICIFGPRSKGWACM-NH$_2$ | 313 |
| 66 | 89 | DTHFPICIFGPRSKGAVCM-NH$_2$ | 520 |
| 31 | 58 | DTHFPICIFGPRSKAWVCM-NH$_2$ | 175 |
| 37 | 64 | DTHFPICIFGPRSAGWVCM-NH$_2$ | 239 |
| 16 | 43 | DTHFPICIFGPRAKGWVCM-NH$_2$ | 88 |
| 34 | 61 | DTHFPICIFGPASKGWVCM-NH$_2$ | 206 |
| 354 | 334 | DTHFPICIFGARSKGWVCM-NH$_2$ | 153 |
| 22 | 49 | DTHFPICIFAPRSKGWVCM-NH$_2$ | 9430 |
| 67 | 90 | DTHFPICIAGPRSKGWVCM-NH$_2$ | 2466 |
| 68 | 91 | DTHFPICAFGPRSKGWVCM-NH$_2$ | >10 µM |
| 69 | 92 | DTHFPIAIFGPRSKGWVAM-NH$_2$ | Inactive |

TABLE 8-continued

Alanine scan of Compound 18

| Compound Number | SEQ ID No. | Sequence | EC50 (nM) (n > 3) |
|---|---|---|---|
| 29 | 56 | DTHFPACIFGPRSKGWVCM-NH$_2$ | 157 |
| 26 | 53 | DTHFAICIFGPRSKGWVCM-NH$_2$ | 147 |
| 38 | 65 | DTHAPICIFGPRSKGWVCM-NH$_2$ | 254 |
| 60 | 87 | DTAFPICIFGPRSKGWVCM-NH$_2$ | 498 |
| 43 | 70 | DAHFPICIFGPRSKGWVCM-NH$_2$ | 265 |
| 33 | 60 | ATHFPICIFGPRSKGWVCM-NH$_2$ | 184 |

Inactive = Not active at 30 µM and/or lowest dose

As was the case with the alanine scan of compound 1 (cysteine in position 6) this scan identified residues within compound 18 (cysteine in position 7) that are important for activity, as well as several residues that appear to be less important for activity and thus may modified without ablating activity.

Example 7

Plasma Stability

Serum stability experiments were undertaken to complement the in vivo results and assist in the design of potent, stable Ferroportin agonists. In order to predict the stability in humans, ex vivo stability studies were initially performed in human serum.

Key peptides (10 µM) were incubated with pre-warmed human serum (Sigma) at 37 degrees C. Samples were taken at various time points up to 24 hours. The samples were separated from serum proteins and analysed for the presence of the peptide of interest using LC-MS. The amount of intact peptide in each sample was calculated using the analyte peak area in relation to the zero time point. Table 9 shows the results of this study.

TABLE 9

Stability of key compounds in human serum

| Compound No. | t½ (h) |
|---|---|
| Hepcidin | 2.76 |
| Mini Hepcidin 1-9 | 0.10 |
| 1 | 0.18 |
| 18 | 2.32 |
| 46 | 2.10 |
| 2 | 1.99 |
| 47 | ~40 |
| 8 | 0.51 |
| 3 | 0.51 |

Example 8

Reduction of Free Plasma Iron in Rats

To investigate whether the hepcidin mimetic Compound No. 2 was effective in decreasing free $Fe^{2+}$ in serum, Retro Inverse mini Hepcidin was used as a reference peptide. Although RI mini-Hep has a very low potency in vitro it is highly active in vivo as reported by Presza et al. J Clin Invest. 2011.

At Day 1, the animals were monitored for free $Fe^{2+}$ in serum. In order to reach a homogenous serum level, $Fe^{2+}$ was analyzed and a homogenous cohort of 7 or 8 animals randomized to each treatment group. At Day 2, an acute experiment where the animals were subjected to i.p. dosing of test compound and subsequent tail vein blood samples. Prior to dosing, the animals were put under a heating lamp for 3-5 minutes. Blood samples were drawn from the tail vein from all animals in order to determine serum iron levels prior to vehicle or compound dosing. Animals were dosed i.p. with 1 ml of test substance in vehicle or just vehicle and blood samples of 250 µl was drawn from each animal at t=0, 60, 120, 240, 360 min and 24 hours in the study of the reference compound. The dose response study performed with Retro Inverse (RI) mini-Hepcidin (Reference compound), and the efficacy study performed with Compound No. 2 were performed as two separate experiments.

Analysis of $Fe^{2+}$ from Day 0 and 1 was done at a later time point not later than 10 days after. The chemicals and equipment used in this example are shown in Table 10.

TABLE 10

Chemicals and equipment used in this example

| Drug Name | Cmpd. No. | SEQ ID No. | MW (g/mol) | Peptide Content Calculated % | Peptide Content Determined % | Purity % | Solvent |
|---|---|---|---|---|---|---|---|
| Isovaleric acid-DTHFPICIFGPRSKGWVC-NH$_2$ | 2 | 29 | 2144.52 | 86.2 | 86.2 | 90 | Na-Acetate buffer |
| RI-Hepcidin1-9 | | 337 | 1091.3 | 82.7 | 82.7 | 94.2 | Strong PBS |

Initially, a peptides were solubilized in acidic H₂O in pH=2.5 an to a concentration of 3 mg/ml API. Compounds were thereafter either dissolved in Na-Acetate buffer (50 mM Acetic Acid, 125 mM NaCl, pH 5.0) or strong PBS, (25 mM sodium phosphate, 125 mM NaCl, pH 7.4).

Male Sprague-Dawley rats weighing 200-250 g were used in the study. They were housed in groups for n=2 in a light-, temperature- and humidity-controlled room (12-hour light: 12-hour dark cycle, lights on/off at 0600/1800 hour; 23 degrees Celcius; 50% relative humidity). Humane endpoints were applied, according to OECD's 'Guidelines for Endpoints in Animal Study Proposals." The animals were monitored daily. In case of significantly affected condition (based on signs such as weight loss >30% (obese animals); abnormal posture; rough hair coat; exudate around eyes and/or nose; skin lesions; abnormal breathing; difficulty with ambulation; abnormal food or water intake; or self mutilation), or other conditions causing significant pain or distress, the animals were euthanized immediately.

Iron content in plasma/serum is measured for iron content using a colorimetric assay on the Cobas c 111 according to instructions from the manufacturer of the assay (assay: IRON2: ACN 661).

The data obtained from the cobas Iron2 analysis are presented as mean values+/−SEM.

Figure 2:
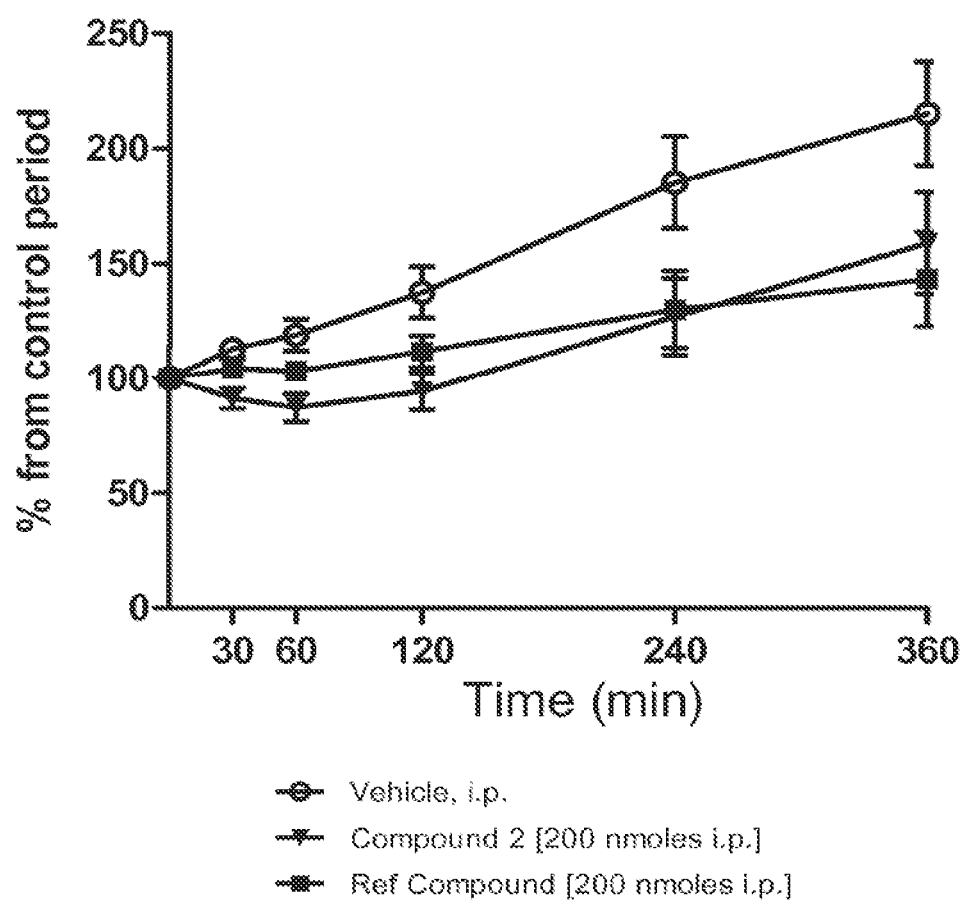
FIG. 2 shows time dependent changes in serum iron following animal exposure to vehicle, Compound No. 2 and reference compound RI Mini-Hepcidin. The responses are normalized to the initial (t=0) levels.
Figure 3:
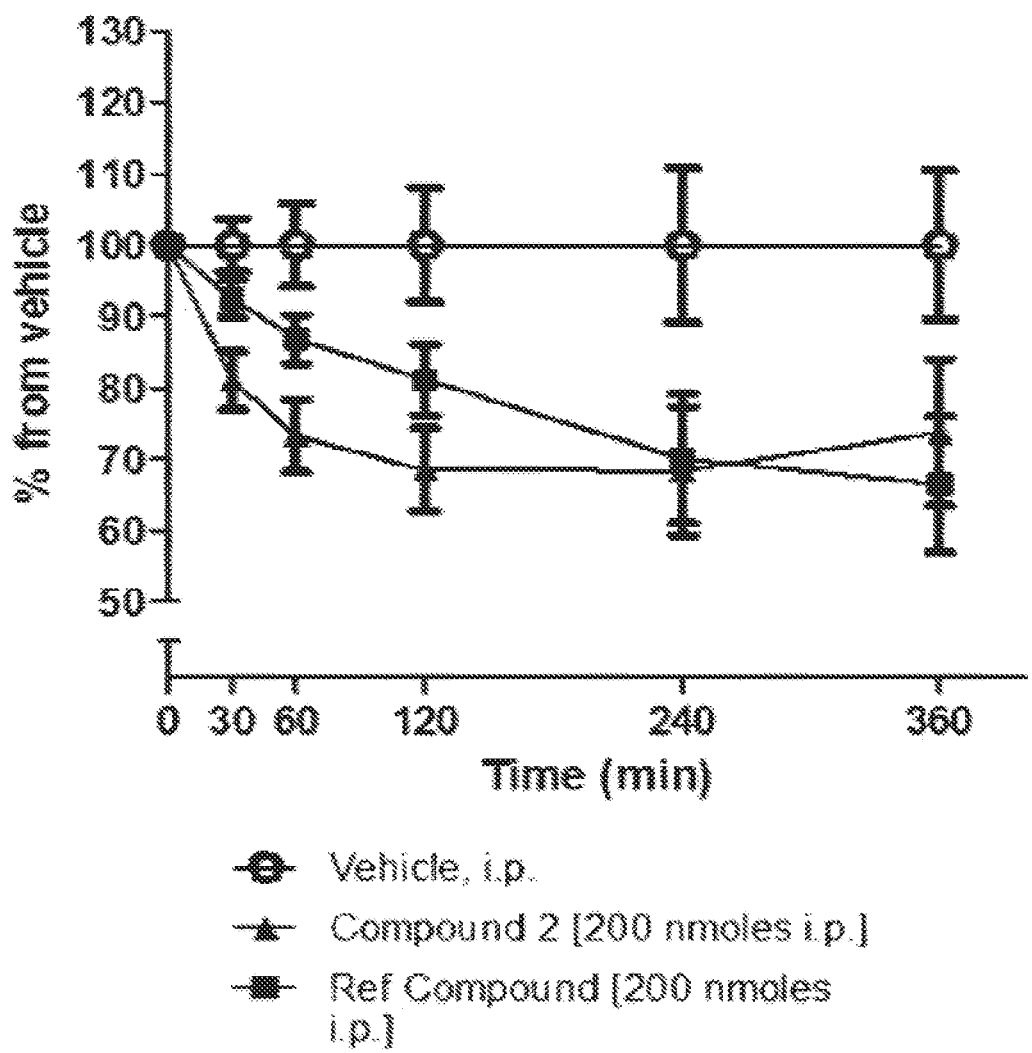
FIG. 3 shows relative decrease of serum iron relative to vehicle control measured with Compound No. 2 as well as the reference compound RI-Mini-Hepcidin at timepoints 0, 30, 60, 120, 240 and 360 minutes. 100% represents the measured average level of serum iron in the vehicle treated animals.

As shown in FIGS. 2 and 3, IP dosing of compound 2 resulted in a decrease in serum iron level that was comparable to that observed after injection of the positive control Retro Inverse mini Hepcidin (RI-Mini-Hepcidin). The decrease induced by RI-Mini-Hepcidin and compound 2 was in neither case significant, which was probably due to a large intergroup variance in the measurements.

Example 9

In Vivo Validation of Selected Peptides

Figure 4:
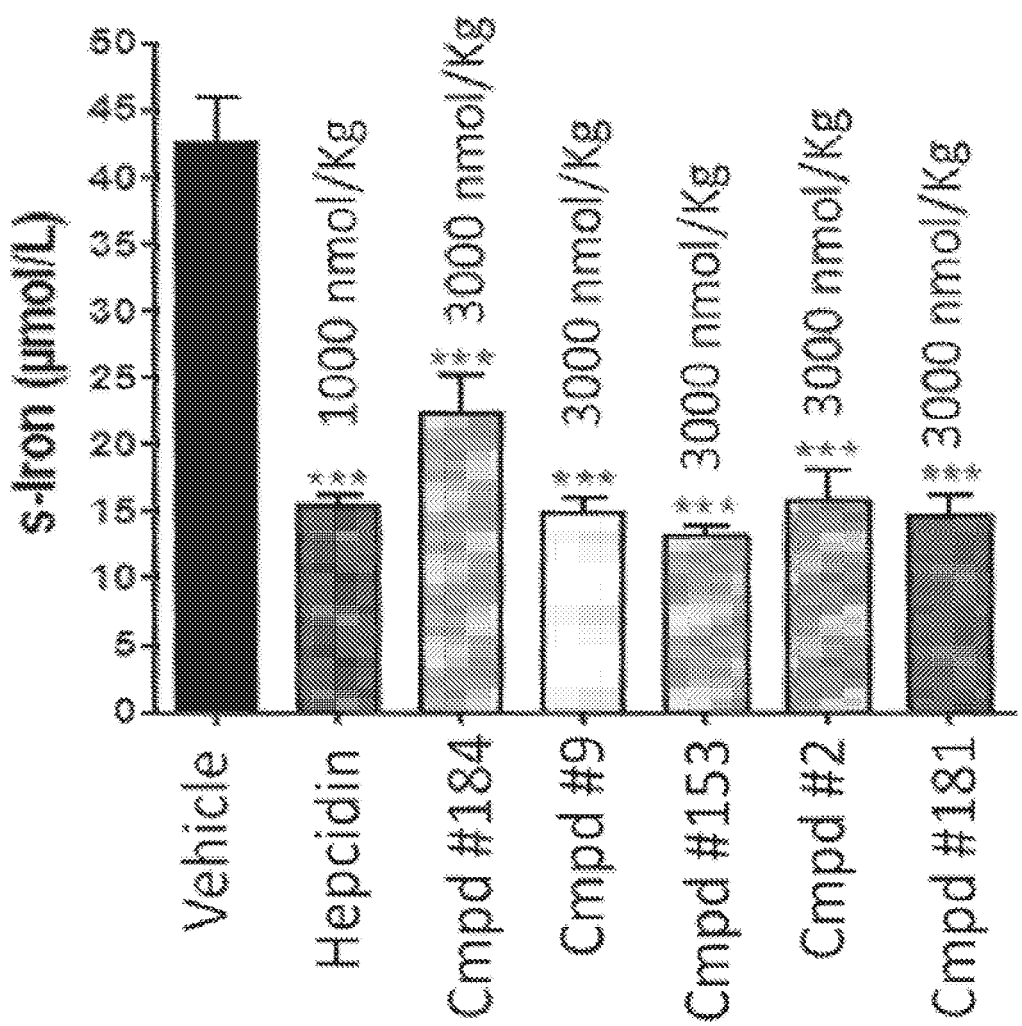
FIG. 4 shows the in vivo serum iron reducing abilities of selected peptides of the present invention and Hepcidin.

Selected peptides of the present invention were tested for in vivo activity, as described in Example 8, with the following changes. Instead of rats, mice (C57-BL6) were tested. Peptides or vehicle controls were administered to the mice (n=8/group) with the compounds of the present invention dosed at 3000 nmol/kg, and a hepcidin control administered via subcutaneous injection at 1000 nmol/kg. The primary goal of this experiment was to validate, in a mouse model, the activity of several peptides that were shown to be active in rat. Serum iron levels were assessed as in Example 8 two hours after peptide or vehicle administration. As shown in FIG. 4, at these doses, a significant reduction in serum iron was observed in compound-treated animals as compared to the vehicle control. Furthermore, the max-dose responses of the compounds of the invention were very similar to the max-dose response achieved with Hepcidin.

Figure 5:
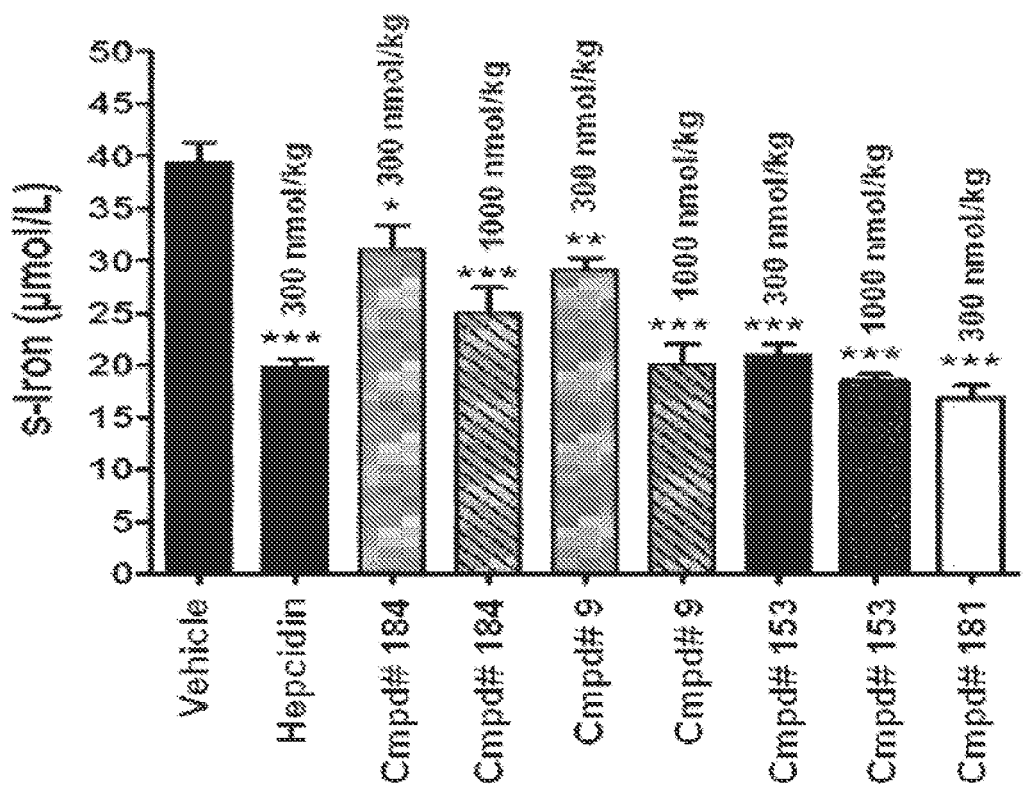
FIG. 5 shows a dose response of the in vivo serum iron reducing abilities of selected peptides of the present invention and Hepcidin.

A similar experiment was performed with lower doses to assess the dose response of these compounds for inducing serum iron reduction. Methods were as described above in this Example, except for the following parameters: n=4 mice/group, however n=8 for the vehicle, as two groups were pooled. Mice were administered test compounds at two separate dosages (300 nmol/kg or 1000 nmol/kg), via subcutaneous injection. Serum iron levels were assessed as in Example 8 two hours after peptide or vehicle injection. As shown in FIG. 5, these peptides induced similar iron reductions as did native hepcidin in vivo. Moreover, it was clear that several of the compounds were able to induce maximum effects at dosages as low as 300 nmol/kg.

Other peptides were tested similarly, either in rats as described in Example 8, or in mice as described above in the present Example, and the results of these tests are presented in Table 11, herein, in the column having the heading "in vivo activity." In this table, dosing is indicated in the sub-headings listed in the first row of the "in vivo activity" column; in vivo activity data is reported as a "yes" or "no" determination, with yes indicating that in vivo activity for serum iron reduction was observed, and with "no" indicating that no such activity was observed. The route of peptide administration was via subcutaneous injection, unless otherwise indicated as having been via intraperitoneal injection (this is noted on the table by "i.p." in parentheses following the "yes" or "no" determination).

Figure 6:
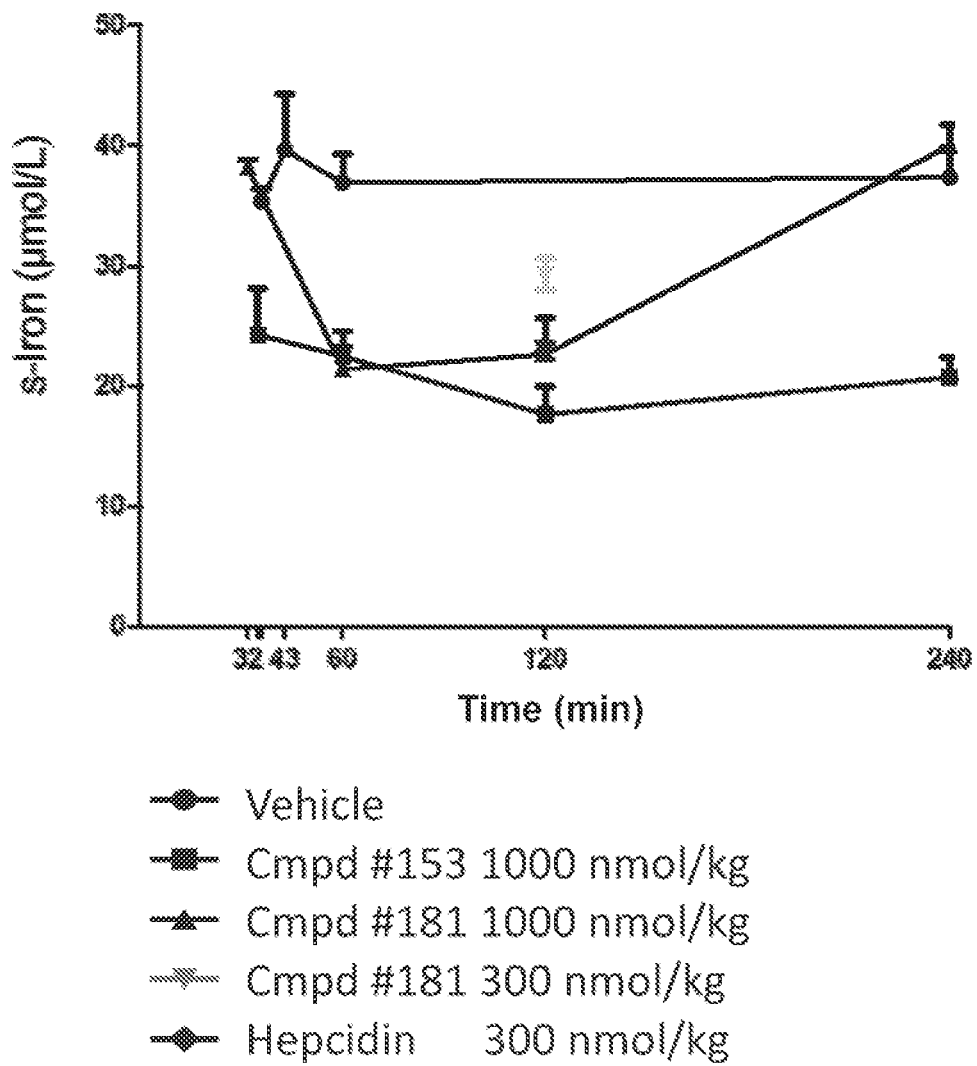
FIG. 6 shows the PK/PD effects for the in vivo serum iron reducing abilities of selected peptides of the present invention and Hepcidin. For Hepcidin and the 300 nmol/kg treatment with compound #181, only one timepoint was taken at t=120 min. The Hepcidin response is not clearly visible on this graph, as it overlapped with the Cmpd #181 1000 nmol/kg plot at the t-120 min point. The single data point for compound #181 300 nmol/kg is located directly above the Hepcidin point.

The peptides were also tested for other pharmacokinetic/pharmacodynamic (PK/PD) parameters using methods commonly know by the skilled artisan. The results of these tests are also indicated on Table 11. These parameters included determinations regarding stability (hours stable in plasma from the indicated human or rat subject), half-life in mice, and in vitro activity (EC$_{50}$), tested as described in Example 2. One example of such a study is presented in FIG. 6, wherein the PK/PD properties of two compounds of the present invention (#153 and #181) were compared with hepcidin to determine their PK/PD effects in C57BL6 mice. Each of these compounds produced a rapid decrease in serum iron, which was transient in the case of Cmpd #181, and sustained in the case of Cmpd #153.

These data, in addition to the data presented herein in Table 11, demonstrated the activity and beneficial PK/PD properties of the peptides of the present invention, a plurality of which show similar or improved PK/PD profiles as compared to hepcidin.

TABLE 11

| | | Peptide activities in vivo | | | | | |
|---|---|---|---|---|---|---|---|
| | | | | Mouse PK | In Vitro Activity | In Vivo Activity (s.c.) | |
| Cmpd No | Sequence | Stability | | $T_{1/2}$ | EC50 | 300 | 1000 |
| | | Rat | Human | (min) | (nM) | nmol/kg | nmol/kg |
| Hepcidin | Hy-DTHFPICIFCCGCCHRSKCGMCCKT-OH SEQ ID NO: 335 | Var | 2.76 | | 34 | Yes | Yes |
| 2 | Isovaleric acid-DTHFPICIFGPRSKGWVC-NH₂ (SEQ ID NO: 29) | 0.15 | 1.99 | 17.4 | 5 | Yes | Yes |

TABLE 11-continued

Peptide activities in vivo

| Cmpd No | Sequence | Stability Rat | Stability Human | Mouse PK $T_{1/2}$ (min) | In Vitro Activity EC50 (nM) | In Vivo Activity (s.c.) 300 nmol/kg | In Vivo Activity (s.c.) 1000 nmol/kg |
|---|---|---|---|---|---|---|---|
| 3 | Isovaleric acid-DTHFPCIIFGPRSRGWVCK-NH$_2$ (SEQ ID NO: 30) | 0.08 | 0.43 | | 15 | No (i.p.) | No (i.p.) |
| 105 | Isovaleric acid-DTHFPCIIFEPRSKGWVCK-NH$_2$ (SEQ ID NO: 128) | 0.68 | 2.22 | 36.9 | 10 | Yes | Yes |
| 9 | Isovaleric acid-DTHFPCIKFGPRSKGWVCK-NH$_2$ (SEQ ID NO: 36) | 0.14 | 0.57 | 22.5 | 32 | Yes | Yes |
| 10 | Isovaleric acid-DTHFPCIQFGPRSKGWVCK-NH$_2$ (SEQ ID NO: 37) | 0.12 | | | 35 | — | Minor |
| 15 | Isovaleric acid-DTHFPICIEFGPRSKGWVCK-NH$_2$ (SEQ ID NO: 42) | 0.15 | | | 79 | — | Minor |
| 115 | Isovaleric acid-DTHFPCIIFGPRSKGCK-NH$_2$ (SEQ ID NO: 138) | | | | 21 | — | No |
| 150 | Isovaleric acid-DTHFPCIKFK(PEG8)PRSKGWVCK-NH$_2$ (SEQ ID NO: 173) | 0.42 | 1.35 | 31.6 | 7 | Yes | |
| 153 | Isovaleric acid-DTHFPCIKFGPRSKGWVCK(PEG8)-NH$_2$ (SEQ ID NO: 176) | 0.41 | 3.36 | | 18 | Yes | Yes |
| 176 | Isovaleric acid-DTHFPICIFGPRSK(PEG8)GWVC-NH$_2$ (SEQ ID NO: 199) | 1.62 | 15 | | 6 | Yes | |
| 184 | Isovaleric acid-DTHFPCIKFEPRSKGCK-NH$_2$ (SEQ ID NO: 207) | 2.12 | 8.16 | 36.9 | 16 | Yes | Yes |
| 181 | Isovaleric acid-DTHFPCIKFEPRSKGWVCK-NH$_2$ (SEQ ID NO: 204) | | | | 15 | Yes | |

Unless otherwise stated all compounds were injected s.c.
Note
Compound 2 was injected I.P.

Example 10

In Vitro Activity of Selected Peptide Dimers

Selected peptide dimers of the present invention were tested for in vitro activity, as described in Example 2. The EC$_{50}$ and % activity at 1 μM were determined for the peptide monomers and peptide dimers shown in Table 12. These peptide dimers were dimerized via a single disulphide linkage between a cysteine residue present in each peptide monomer. The results of these experiments are shown in Table 12.

TABLE 12

In vitro activity of peptides dimerized through a single disulphide linkage between cysteine residues

| Cmpd # | Sequence | $EC_{50}$ (nM) (n = 3) | % Activity At 1 uM | Cmpd # | Sequence | $EC_{50}$ (nM) (n = 3) | % Activity At 1 uM |
|---|---|---|---|---|---|---|---|
| 1 | Hy-DTHFPCIIF-NH$_2$ (SEQ ID NO: 28) | 133 | 92 | 311 | (Hy-DTHFPCIIF-NH$_2$)$_2$ (SEQ ID NO: 338) | 35 | 96 |
| 293 | Hy-DTHFPCIF-NH$_2$ (SEQ ED NO: 316) | >1 µM | 52 | 312 | (Hy-DTHFPCI_F-NH$_2$)$_2$ (SEQ ID NO:339) | >300 nM | 51 |
| 297 | Hy-DTHFPCIKFF-NH$_2$ (SEQ ID NO: 320) | >300 nM | 64 | 314 | (Hy-DTHFPCIKFF-NH$_2$)$_2$ (SEQ ID NO: 341) | 130 | 100 |
| 299 | Hy-LTHFPCIIF-NH$_2$ (SEQ ID NO: 322) | >300 nM | 64 | 315 | (Hy-LTHFPCIIF-NH$_2$)$_2$ (SEQ ID NO: 342) | 35 | 97 |
| 300 | Hy-ETHFPCIIF-NH$_2$ (SEQ ID NO: 323) | >300 nM | 77 | 316 | (Hy-ETHFPCIIF-NH$_2$)$_2$ (SEQ ID NO: 343) | 63 | 100 |
| 302 | Hy-DTKFPCIIF-NH$_2$ (SEQ ID NO: 325) | >1 µM | 60 | 317 | (Hy-DTKFPCIIF-NH$_2$)$_2$ (SEQ ID NO: 344) | 137 | 87 |
| 304 | Hy-DTHFPCIIK-NH$_2$ (SEQ ID NO: 327) | >1 µM | 55 | 318 | (Hy-DTHFPCIEK-NH$_2$)$_2$ (SEQ ID NO:345) | >300 nM | 49 |
| 305 | Hy-DTHFPCIIR-NH$_2$ (SEQ ID NO: 328) | >1 µM | 62 | 319 | (Hy-DTHFPCIIR-NH$_2$)$_2$ (SEQ ID NO:346) | 268 | 79 |
| 307 | Hy-DTHFPCIVF-NH$_2$ (SEQ ID NO: 330) | >300 nM | 75 | 320 | (Hy-DTHFPCIVF-NH$_2$)$_2$ (SEQ ID NO: 347) | 50 | 93 |
| 308 | Hy-DTHFPCILF-NH$_2$ (SEQ ED NO:331) | >300 nM | 89 | 321 | (Hy-DTHFPCILF-NH$_2$)$_2$ (SEQ ID NO: 348) | 83 | 94 |
| 309 | Hy-DTHFPCILK-NH$_2$ (SEQ ID NO: 332) | >300 nM | 55 | 322 | (Hy-DTHFPCILK-NH$_2$)$_2$ (SEQID NO: 349) | >300 nM | 47 |
| 310 | Hy-DTHFPCIEK-NH$_2$ (SEQ ID NO: 333) | >1 µM | 0 | 323 | (Hy-DTHFPCIEK-NH$_2$)$_2$ (SEQ ID NO: 350) | >1 µM | 0 |
| 288 | Isovaleric acid-DTHFPCIIF-NH$_2$ (SEQ ID NO: 311) | 16 | 100 | 325 | (Isovaleric acid-DTHFPCIIF-NH$_2$)$_2$ (SEQ ID NO: 351) | 4 | 100 |
| 291 | Isovaleric acid-DTHFPCIKF-NH$_2$ (SEQ ID NO: 314) | 7 | 100 | 326 | (Isovaleric acid-DTHFPCIKF-NH$_2$)$_2$ (SEQ ID NO: 352) | 3 | 100 |

$EC_{50}$ values were also determined for the peptide dimers having the sequences shown in Table 10. The activity of peptide dimers dimerized only through a disulphide linkage between the two peptide monomers was compared to the activity of peptide dimers of the same monomers dimerized through both the disulphide linkage and also a DIG linking moiety. In addition, the activity of peptide dimers dimerized through a DIG linking moiety coupled to the N-terminus of the monomers, the C-terminus of the monomers, or different internal lysine residues was examined. The results of these experiments are provided in Table 13.

TABLE 13
| Cmpd No. | Sequence | EC$_{50}$ (nM) (n > 3) |
|---|---|---|
| 327 (SEQ ID NO: 353) | (DTHFPCIKF-NH$_2$)$_2$<br>Hy-Asp-Thr-His-Phe-Pro-Cys-Ile-Lys-Phe-NH$_2$<br>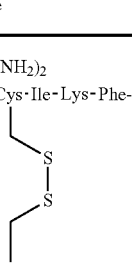<br>Hy-Asp-Thr-His-Phe-Pro-Cys-Ile-Lys-Phe-NH$_2$ | 193 |
| 328 (SEQ ID NO: 354) | DIG-(DTHFPCIKFNH$_2$)$_2$DIG through N-terminus<br>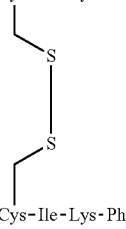 | >1000 |
| 329 (SEQ ID NO: 355) | (Isovaleric acid-DTKFPCIRF-NH$_2$)$_2$<br>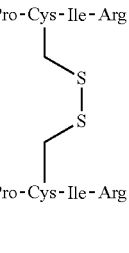 | 9 |
| 340 (SEQ ID NO: 356) | (Isovaleric acid-DTKFPCIRF-NH$_2$)$_2$ DIG through K3<br>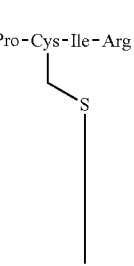 | 212 |

TABLE 13-continued
Dimer Position explored (DIG as the representative linker explored)
| Cmpd No. | Sequence | EC$_{50}$ (nM) (n > 3) |
|---|---|---|
| 326 (SEQ ID NO: 357) | (Isovaleric acid-DTHFPCIKF-NH$_2$)$_2$ | 3 |
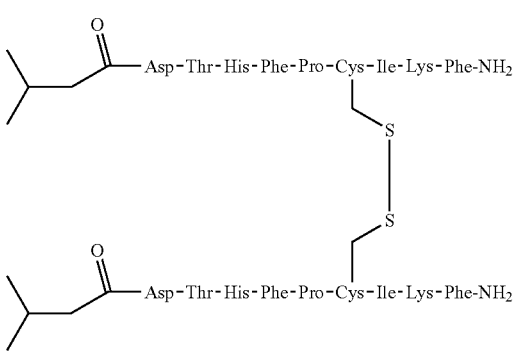
| 342 (SEQ ID NO: 358) | (Isovaleric acid-DTKFPCIRF-NH$_2$)$_2$ DIG through K$_3$ | 10 |
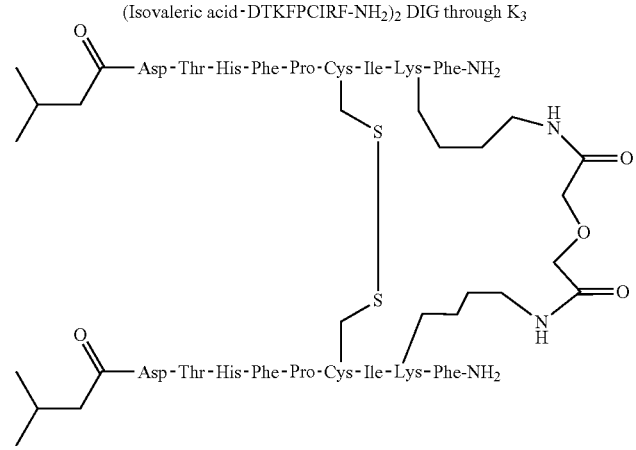
| 343 (SEQ ID NO: 359) | (Isovaleric acid-DTHFPCIRK-NH$_2$)$_2$ | 11 |
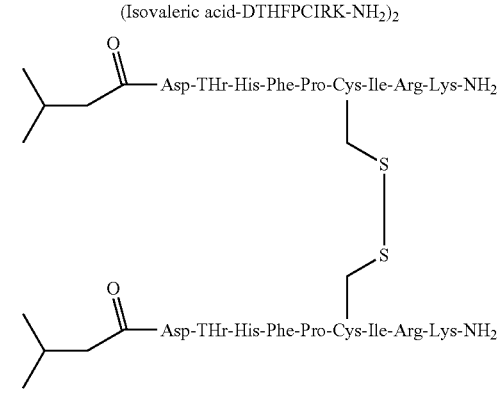

TABLE 13-continued

Dimer Position explored (DIG as the representative linker explored)

| Cmpd No. | Sequence | EC$_{50}$ (nM) (n > 3) |
|---|---|---|
| 344 (SEQ ID NO: 360) | (Isovaleric acid-DTHFPCIRK-NH$_2$)$_2$ DIG through K9 | 45 |
| 345 (SEQ ID NO: 361) | (Isovaleric acid-DTHFPCIKFK-NH$_2$)$_2$ | 8 |
| 346 (SEQ ID NO: 362) | (Isovaleric acid-DTHFPCIKFK-NH$_2$)$_2$ DIG through K$_{10}$ | 15 |

Figure 7:
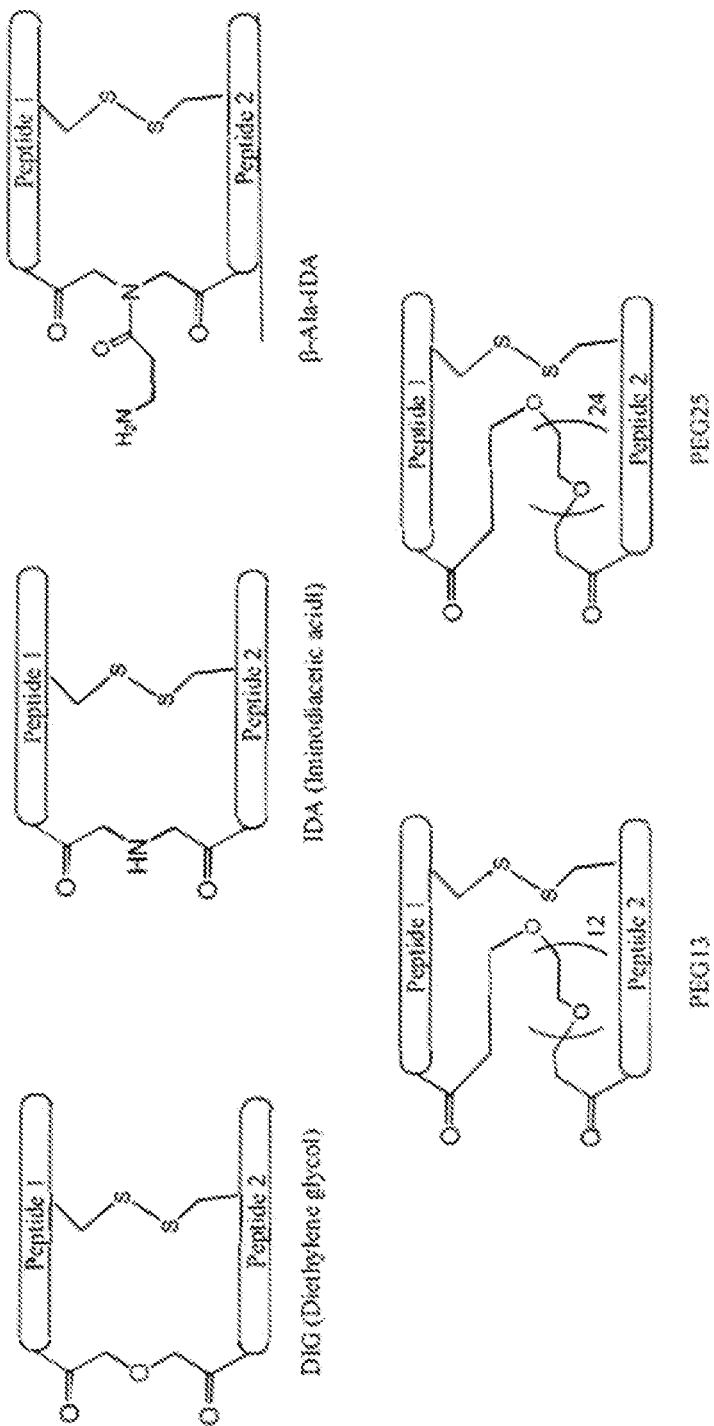
FIG. 7 shows selected examples of linkers that were used to dimerize the peptides.

EC$_{50}$ values were determined for peptide dimers comprising different linking moieties, and as compared to linkage via a disulphide bridge between the two peptide monomers, EC$_{50}$ values were determined for peptide dimers comprising different linking moieties, and as compared to linkage via a disulphide bridge between the two peptide monomers, including the peptide dimers shown in Table 14. Where a particular linking moiety is not indicated, the peptide dimer was dimerized via a disulphide bridge between cysteine residues present in each of the peptide monomers of the peptide dimer. The results of this experiment are shown in Table 14, and various linker types are shown as schematics in FIG. 7.

TABLE 14

Dimerization using various linkers at different positions

| Cmpd. No. | Sequence | Log dilutions EC$_{50}$ (nM) (n > 3) |
|---|---|---|
| 327 | (Hy-DTHFPCIKF-NH$_2$)$_2$ (SEQ ID NO: 353) | 193 |
| 348 | (Hy-DTHFPCIKF-NH$_2$)$_2$-[IDA-(β-Ala)] (SEQ ID NO: 363) | 18 |
| 326 | (Isovaleric acid-DTHFPCIKF-NH$_2$)$_2$ (SEQ ID NO: 357) | 6 |
| 349 | (Isovaleric acid-DTHFPCIKF-NH$_2$)$_2$-[IDA-(β-Ala)-Palm] (SEQ ID NO: 364) | 5 |
| 345 | (Isovaleric acid-DTHFPCIKFK-NH$_2$)$_2$ (SEQ ID NO: 361) | 8 |
| 346 | (Isovaleric acid-DTHFPCIKFK-NH$_2$)$_2$-[DIG] DIG through K10 (SEQ ID NO: 362) | 15 |
| 327 | (Hy-DTHFPCIKF-NH$_2$)$_2$ (SEQ ID NO: 353) | 193 |
| 351 | [PEG25]-(DTHFPCIKF-NH$_2$)$_2$ (SEQ ID NO: 366) | >1000 |

In Table 14, brackets indicate linker and any linker conjugates (if present), e.g., [linker].

EC$_{50}$ values were determined for peptide dimers dimerized via a glycol linker attached to the ε$_N$ of lysine residues within the peptide chains, as compared to the peptide monomers. As shown in Table 15, the peptide dimers had lower EC$_{50}$S than their corresponding peptide monomers. In this case, the disulphide bond exists intramolecularly within each peptide (e.g., cmpd #2 and cmpd #3) moiety before dimerization through using DIG through acylation of the Nε of lysine.

TABLE 15

Dimerization through a glycol linker attached to the εN of lysine within the peptide chain

| Cmpd No. | Sequence | Log dilutions EC50 (nM) (n > 3) |
|---|---|---|
| 3 | Isovaleric acid-DTHFPCIIFGPRSRGWVCK-NH$_2$ (SEQ ID NO: 30) | 15 |
| 352 | (Isovaleric acid-DTHFPCIIFGPRSRGWVCK-NH$_2$)$_2$-[DIG] (SEQ ID NO: 367) | 5 |
| 2 | Isovaleric acid-DTHFPICIFGPRSKGWVC-NH$_2$ (SEQ ID NO: 29) | 4.1 |
| 353 | (Isovaleric acid-DTHFPICIFGPRSKGWVC-NH$_2$)$_2$-[DIG] (SEQ ID NO: 368) | 22 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

The invention claimed is:

1. A method of treating a disease of iron metabolism in a subject in need thereof comprising administering to said subject a peptide comprising the sequence (SEQ ID NO: 241)
Isovaleric acid-DTHFPCI(K(isoGlu-Palm))FEPRSKGCK-NH₂ or a pharmaceutically acceptable salt thereof, and
wherein the peptide of SEQ ID NO: 241 comprises a disulfide bond between two cysteine residues;
wherein the disease of iron metabolism is hereditary hemochromatosis, iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, β-thalassemia, or alpha thalassemia.

2. The method of claim 1, wherein the peptide of SEQ ID NO: 241 comprises the structure 3. The method of claim 1, wherein the subject is a mammal.

4. The method of claim 3, wherein the mammal is a human.

5. The method of claim 1, comprising administering the peptide in a pharmaceutical formulation comprising a pharmaceutically acceptable carrier.

6. The method of claim 5, wherein the pharmaceutical formulation is for oral, intravitreal, rectal, vaginal, nasal, topical, enteral or parenteral-administration.

7. The method of claim 5, wherein the pharmaceutical formulation is for oral administration.

8. The method of claim 5, wherein the pharmaceutical formulation is for subcutaneous administration.

9. The method of claim 5, wherein the pharmaceutical formulation is a capsule, cachet, or tablet.

10. The method of claim 5, wherein the pharmaceutical formulation is a single-dose injectable.

11. The method of claim 1, the method further comprising administering the peptide or the pharmaceutically acceptable salt thereof in a dosage of about 0.0001 to about 100 mg/kg body weight per day.

12. The method of claim 1, the method further comprising administering the peptide or the pharmaceutically acceptable salt thereof in a dosage of about 0.001 to about 10 mg/kg body weight per day.

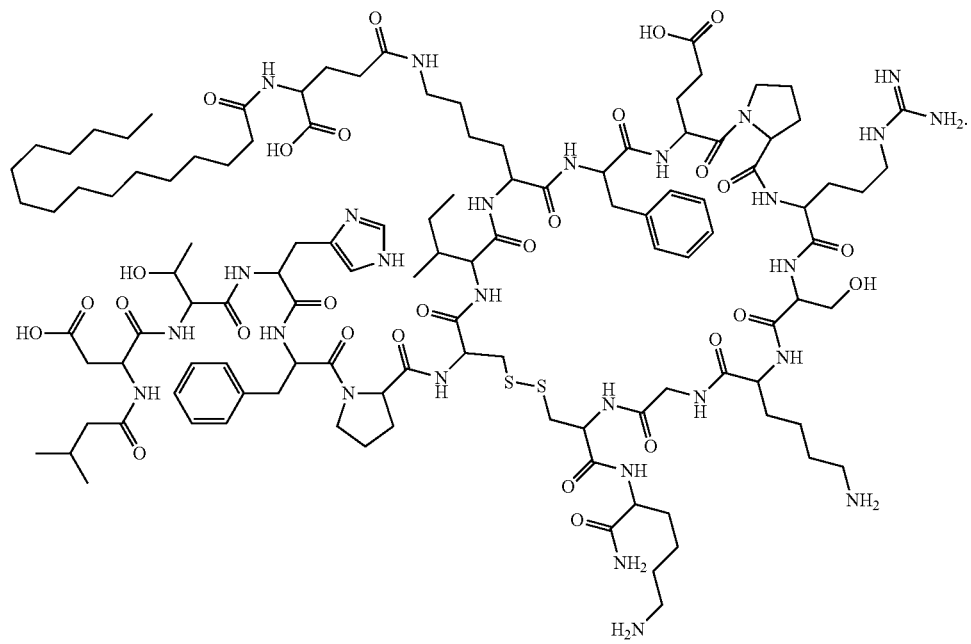 [SMILES: CCCCCCCCCCCCCCCC(=O)NC(CCC(=O)NCCCCC1NC(=O)C(C(C)CC)NC(=O)C(NC(=O)C2CCCN2C(=O)C(Cc2ccccc2)NC(=O)C(Cc2c[nH]cn2)NC(=O)C(NC(=O)C(CC(=O)O)NC(=O)CC(C)C)C(C)O)CSSCC(C(=O)NC(CCCCN)C(N)=O)NC(=O)CNC(=O)C(CCCCN)NC(=O)C(CO)NC(=O)C(CCCNC(=N)N)NC(=O)C2CCCN2C(=O)C(CCC(=O)O)NC(=O)C(Cc2ccccc2)NC1=O)C(=O)O]

13. The method of claim 1, the method further comprising administering the peptide or the pharmaceutically acceptable salt thereof in a dosage of about 0.01 to about 1 mg/kg body weight per day.

14. The method of claim 13, the method further comprising administering the peptide or the pharmaceutically acceptable salt thereof once daily, twice daily, once every two, three, four, five or six days, once or twice weekly, or once or twice monthly.

15. The method of claim 5, wherein the pharmaceutical formulation is for intramuscular, intravenous, intradermal, or transdermal administration.

* * * * *

SEQUENCE LISTING

Sequence total quantity: 375
SEQ ID NO: 1         moltype =     length =
SEQUENCE: 1

```
000

SEQ ID NO: 2              moltype =   length =
SEQUENCE: 2
000

SEQ ID NO: 3              moltype = AA  length = 10
FEATURE                   Location/Qualifiers
REGION                    1..10
                          note = Hepcidin peptide analogue motif
VARIANT                   1
                          note = Xaa = Asp, Glu, Iminodiacetic acid, pyroglutamic
                           acid, beta-homoaspartic acid or absent
VARIANT                   4
                          note = Xaa = Phe or (beta,beta diphenylalanine)
VARIANT                   5
                          note = Xaa = Pro or beta-homoproline
VARIANT                   8
                          note = Xaa = Ile, Lys, Glu, Phe, Gln or Arg
VARIANT                   10
                          note = Xaa = Lys or absent
source                    1..10
                          mol_type = protein
                          organism = synthetic construct
SEQUENCE: 3
XTHXXCIXFX                                                                    10

SEQ ID NO: 4              moltype = AA  length = 10
FEATURE                   Location/Qualifiers
REGION                    1..10
                          note = Hepcidin peptide analogue motif
VARIANT                   1
                          note = Xaa = Asp, Glu or Iminodiacetic acid
VARIANT                   5
                          note = Xaa = Pro or beta-homoproline
VARIANT                   8
                          note = Xaa = Ile Lys or Phe
VARIANT                   10
                          note = Xaa = absent
source                    1..10
                          mol_type = protein
                          organism = synthetic construct
SEQUENCE: 4
XTHFXCIXFX                                                                    10

SEQ ID NO: 5              moltype =   length =
SEQUENCE: 5
000

SEQ ID NO: 6              moltype =   length =
SEQUENCE: 6
000

SEQ ID NO: 7              moltype = AA  length = 10
FEATURE                   Location/Qualifiers
REGION                    1..10
                          note = Hepcidin peptide analogue motif
VARIANT                   1
                          note = Xaa = Gly, Pro or D-Pro
VARIANT                   2
                          note = Xaa = Pro or Gly
VARIANT                   3
                          note = Xaa = Arg or Lys
VARIANT                   8
                          note = Xaa = Val or Thr
VARIANT                   10
                          note = Xaa = Met, Lys or absent
source                    1..10
                          mol_type = protein
                          organism = synthetic construct
SEQUENCE: 7
XXXSKGWXCX                                                                    10

SEQ ID NO: 8              moltype =   length =
SEQUENCE: 8
000

SEQ ID NO: 9              moltype = AA  length = 15
FEATURE                   Location/Qualifiers
```

```
REGION                   1..15
                         note = Hepcidin peptide analogue motif
VARIANT                  3
                         note = Xaa = Gly or absent
VARIANT                  6
                         note = Xaa = Ser or Pro;
VARIANT                  7
                         note = Xaa = Ile or Lys
VARIANT                  8
                         note = Xaa = Gly or absent
VARIANT                  12
                         note = Xaa = Arg or Ala
VARIANT                  13
                         note = Xaa = Cys or Val or absent
VARIANT                  14
                         note = Xaa = Cys, Arg, Thr or absent
VARIANT                  15
                         note = Xaa = Arg or absent
source                   1..15
                         mol_type = protein
                         organism = synthetic construct
SEQUENCE: 9
VCXHRXXXCY RXXXX                                                                   15

SEQ ID NO: 10            moltype =    length =
SEQUENCE: 10
000

SEQ ID NO: 11            moltype =    length =
SEQUENCE: 11
000

SEQ ID NO: 12            moltype =    length =
SEQUENCE: 12
000

SEQ ID NO: 13            moltype =    length =
SEQUENCE: 13
000

SEQ ID NO: 14            moltype =    length =
SEQUENCE: 14
000

SEQ ID NO: 15            moltype = AA  length = 10
FEATURE                  Location/Qualifiers
REGION                   1..10
                         note = Hepcidin peptide analogue motif
VARIANT                  1
                         note = Xaa = Asp, Iminodiacetic acid, pyroglutamic acid,
                          beta-homoaspartic acid or absent
VARIANT                  4
                         note = Xaa = Phe or (beta,beta diphenylalanine)
VARIANT                  5
                         note = Xaa = Pro or beta-homoproline
VARIANT                  8
                         note = Xaa = Ile, Lys, Glu, Phe, Gln or Arg
VARIANT                  10
                         note = Xaa = Lys or absent
source                   1..10
                         mol_type = protein
                         organism = synthetic construct
SEQUENCE: 15
XTHXXCIXFX                                                                         10

SEQ ID NO: 16            moltype =    length =
SEQUENCE: 16
000

SEQ ID NO: 17            moltype =    length =
SEQUENCE: 17
000

SEQ ID NO: 18            moltype = AA  length = 10
FEATURE                  Location/Qualifiers
REGION                   1..10
                         note = Hepcidin peptide analogue motif
VARIANT                  1
                         note = Xaa = Gly, Pro or D-Pro
```

```
VARIANT              2
                     note = Xaa = Pro or Gly
VARIANT              3
                     note = Xaa = Arg or Lys
VARIANT              8
                     note = Xaa = Val or Thr
VARIANT              10
                     note = Xaa = Met, Lys or absent
source               1..10
                     mol_type = protein
                     organism = synthetic construct
SEQUENCE: 18
XXXSKGWXCX                                                                      10

SEQ ID NO: 19        moltype =    length =
SEQUENCE: 19
000

SEQ ID NO: 20        moltype = AA  length = 15
FEATURE              Location/Qualifiers
REGION               1..15
                     note = Hepcidin peptide analogue motif
VARIANT              3
                     note = Xaa = Gly or absent
VARIANT              6
                     note = Xaa = Ser or Pro;
VARIANT              7
                     note = Xaa = Ile or Lys
VARIANT              8
                     note = Xaa = Gly or absent
VARIANT              12
                     note = Xaa = Arg or Ala
VARIANT              13
                     note = Xaa = Cys or Val or absent
VARIANT              14
                     note = Xaa = Cys, Arg, Thr or absent
VARIANT              15
                     note = Xaa = Arg or absent
source               1..15
                     mol_type = protein
                     organism = synthetic construct
SEQUENCE: 20
VCXHRXXXCY RXXXX                                                                15

SEQ ID NO: 21        moltype =    length =
SEQUENCE: 21
000

SEQ ID NO: 22        moltype =    length =
SEQUENCE: 22
000

SEQ ID NO: 23        moltype =    length =
SEQUENCE: 23
000

SEQ ID NO: 24        moltype = AA  length = 10
FEATURE              Location/Qualifiers
REGION               1..10
                     note = Hepcidin peptide analogue motif
VARIANT              1
                     note = Xaa = Asp, Iminodiacetic acid, pyroglutamic acid,
                      beta-homoaspartic acid or absent
VARIANT              4
                     note = Xaa = Phe or (beta,beta diphenylalanine)
VARIANT              5
                     note = Xaa = Pro or beta-homoproline
VARIANT              8
                     note = Xaa = Ile, Lys, Glu, Phe, Gln or Arg
VARIANT              10
                     note = Xaa = Lys or absent
source               1..10
                     mol_type = protein
                     organism = synthetic construct
SEQUENCE: 24
XTHXXCIXFX                                                                      10

SEQ ID NO: 25        moltype =    length =
SEQUENCE: 25
```

```
000

SEQ ID NO: 26           moltype = AA  length = 10
FEATURE                 Location/Qualifiers
REGION                  1..10
                        note = Hepcidin peptide analogue motif
VARIANT                 1
                        note = Xaa = Gly, Pro or D-Pro
VARIANT                 2
                        note = Xaa = Pro or Gly
VARIANT                 3
                        note = Xaa = Arg or Lys
VARIANT                 8
                        note = Xaa = Val or Thr
VARIANT                 10
                        note = Xaa = Met, Lys or absent
source                  1..10
                        mol_type = protein
                        organism = synthetic construct
SEQUENCE: 26
XXXSKGWXCX                                                              10

SEQ ID NO: 27           moltype =   length =
SEQUENCE: 27
000

SEQ ID NO: 28           moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 28
DTHFPCIIF                                                                9

SEQ ID NO: 29           moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 29
DTHFPICIFG PRSKGWVC                                                     18

SEQ ID NO: 30           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 30
DTHFPCIIFG PRSRGWVCK                                                    19

SEQ ID NO: 31           moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 31
DTHFPCIIFG PRSKGWVC                                                     18

SEQ ID NO: 32           moltype = AA  length = 19
FEATURE                 Location/Qualifiers
REGION                  1..19
                        note = Hepcidin peptide analogue
MOD_RES                 1
                        note = Xaa is iminodiacetic acid
MOD_RES                 4
                        note = Xaa is beta,beta diphenylalanine
MOD_RES                 5
                        note = Xaa is beta-homoproline
source                  1..19
                        mol_type = protein
                        organism = synthetic construct
```

```
SEQUENCE: 32
XTHXXICIFG PRSKGWVCM                                                          19

SEQ ID NO: 33           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 33
DTHFPCIFFG PRSKGWVCK                                                          19

SEQ ID NO: 34           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 34
DTHFPCIIFG PRSKGWTCK                                                          19

SEQ ID NO: 35           moltype = AA  length = 19
FEATURE                 Location/Qualifiers
REGION                  1..19
                        note = Hepcidin peptide analogue
MOD_RES                 1
                        note = Xaa is iminodiacetic acid
MOD_RES                 4
                        note = Xaa is beta,beta diphenylalanine
MOD_RES                 5
                        note = Xaa is beta-homoproline
source                  1..19
                        mol_type = protein
                        organism = synthetic construct
SEQUENCE: 35
XTHXXCIIFG PRSRGWVCK                                                          19

SEQ ID NO: 36           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 36
DTHFPCIKFG PRSKGWVCK                                                          19

SEQ ID NO: 37           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 37
DTHFPCIQFG PRSKGWVCK                                                          19

SEQ ID NO: 38           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 38
DTHFPCIIFG PRSKGWVCK                                                          19

SEQ ID NO: 39           moltype = AA  length = 22
FEATURE                 Location/Qualifiers
REGION                  1..22
                        note = Hepcidin peptide analogue
source                  1..22
                        mol_type = protein
                        organism = synthetic construct
SEQUENCE: 39
DTHFPICIFV CGHRSICYRR CR                                                      22
```

```
SEQ ID NO: 40            moltype = AA  length = 23
FEATURE                  Location/Qualifiers
REGION                   1..23
                         note = Hepcidin peptide analogue
source                   1..23
                         mol_type = protein
                         organism = synthetic construct
SEQUENCE: 40
ADTHFPICIF VCHRSKGCYR RCR                                                 23

SEQ ID NO: 41            moltype = AA  length = 21
FEATURE                  Location/Qualifiers
REGION                   1..21
                         note = Hepcidin peptide analogue
source                   1..21
                         mol_type = protein
                         organism = synthetic construct
SEQUENCE: 41
DTHFPICIFV CHRSKGCYRA C                                                   21

SEQ ID NO: 42            moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 42
DTHFPCIEFG PRSKGWVCK                                                      19

SEQ ID NO: 43            moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 43
DTHFPICIFG PRAKGWVCM                                                      19

SEQ ID NO: 44            moltype = AA  length = 23
FEATURE                  Location/Qualifiers
REGION                   1..23
                         note = Hepcidin peptide analogue
source                   1..23
                         mol_type = protein
                         organism = synthetic construct
SEQUENCE: 44
ADTHFPICIF VCHRSKGCYR RCR                                                 23

SEQ ID NO: 45            moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 45
DTHFPICIFG PRSKGWVCM                                                      19

SEQ ID NO: 46            moltype = AA  length = 22
FEATURE                  Location/Qualifiers
REGION                   1..22
                         note = Hepcidin peptide analogue
source                   1..22
                         mol_type = protein
                         organism = synthetic construct
SEQUENCE: 46
DTHFPICIFV CHRSKGCYRR CR                                                  22

SEQ ID NO: 47            moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 47
DTHFPICIFG PRSRGWVCK                                                      19
```

```
SEQ ID NO: 48           moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 48
DTHFPCIIFG PRSKGWVCM                                                    19

SEQ ID NO: 49           moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 49
DTHFPICIFA PRSKGWVCM                                                    19

SEQ ID NO: 50           moltype = AA   length = 20
FEATURE                 Location/Qualifiers
REGION                  1..20
                        note = Hepcidin peptide analogue
source                  1..20
                        mol_type = protein
                        organism = synthetic construct
SEQUENCE: 50
DTHFPICIFG PRSKGWVCMH                                                   20

SEQ ID NO: 51           moltype = AA   length = 9
FEATURE                 Location/Qualifiers
REGION                  1..9
                        note = Hepcidin peptide analogue
source                  1..9
                        mol_type = protein
                        organism = synthetic construct
SEQUENCE: 51
DTHFPCIQF                                                               9

SEQ ID NO: 52           moltype = AA   length = 23
FEATURE                 Location/Qualifiers
REGION                  1..23
                        note = Hepcidin peptide analogue
source                  1..23
                        mol_type = protein
                        organism = synthetic construct
SEQUENCE: 52
DTHFPICIFV CGHRSKGCYR RCR                                               23

SEQ ID NO: 53           moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 53
DTHFAICIFG PRSKGWVCM                                                    19

SEQ ID NO: 54           moltype = AA   length = 20
FEATURE                 Location/Qualifiers
REGION                  1..20
                        note = Hepcidin peptide analogue
source                  1..20
                        mol_type = protein
                        organism = synthetic construct
SEQUENCE: 54
DTHFPICIFG PHRSKGWVCM                                                   20

SEQ ID NO: 55           moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 55
```

```
DTHFPICIFG PRAKGWVCM                                                  19

SEQ ID NO: 56          moltype = AA  length = 19
FEATURE                Location/Qualifiers
REGION                 1..19
                       note = Hepcidin peptide analogue
source                 1..19
                       mol_type = protein
                       organism = synthetic construct
SEQUENCE: 56
DTHFPACIFG PRSKGWVCM                                                  19

SEQ ID NO: 57          moltype = AA  length = 23
FEATURE                Location/Qualifiers
REGION                 1..23
                       note = Hepcidin peptide analogue
source                 1..23
                       mol_type = protein
                       organism = synthetic construct
SEQUENCE: 57
DTHFPCIIFV CHRPKGCYRR VCR                                             23

SEQ ID NO: 58          moltype = AA  length = 19
FEATURE                Location/Qualifiers
REGION                 1..19
                       note = Hepcidin peptide analogue
source                 1..19
                       mol_type = protein
                       organism = synthetic construct
SEQUENCE: 58
DTHFPICIFG PRSKAWVCM                                                  19

SEQ ID NO: 59          moltype = AA  length = 23
FEATURE                Location/Qualifiers
REGION                 1..23
                       note = Hepcidin peptide analogue
source                 1..23
                       mol_type = protein
                       organism = synthetic construct
SEQUENCE: 59
DTHFPICIFV CGHRGKGCYR RCR                                             23

SEQ ID NO: 60          moltype = AA  length = 19
FEATURE                Location/Qualifiers
REGION                 1..19
                       note = Hepcidin peptide analogue
source                 1..19
                       mol_type = protein
                       organism = synthetic construct
SEQUENCE: 60
ATHFPICIFG PRSKGWVCM                                                  19

SEQ ID NO: 61          moltype = AA  length = 19
FEATURE                Location/Qualifiers
REGION                 1..19
                       note = Hepcidin peptide analogue
source                 1..19
                       mol_type = protein
                       organism = synthetic construct
SEQUENCE: 61
DTHFPICIFG PASKGWVCM                                                  19

SEQ ID NO: 62          moltype = AA  length = 21
FEATURE                Location/Qualifiers
REGION                 1..21
                       note = Hepcidin peptide analogue
source                 1..21
                       mol_type = protein
                       organism = synthetic construct
SEQUENCE: 62
DTHFPICIFV CHRSKGCYAR C                                               21

SEQ ID NO: 63          moltype = AA  length = 19
FEATURE                Location/Qualifiers
REGION                 1..19
                       note = Hepcidin peptide analogue
source                 1..19
                       mol_type = protein
                       organism = synthetic construct
```

```
SEQUENCE: 63
DTHFPICIFG PRSKGWVCM                                              19

SEQ ID NO: 64           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 64
DTHFPICIFG PRSAGWVCM                                              19

SEQ ID NO: 65           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 65
DTHAPICIFG PRSKGWVCM                                              19

SEQ ID NO: 66           moltype = AA  length = 21
FEATURE                 Location/Qualifiers
REGION                  1..21
                        note = Hepcidin peptide analogue
source                  1..21
                        mol_type = protein
                        organism = synthetic construct
SEQUENCE: 66
DTHFPICIFV CHRSKGCYRR C                                           21

SEQ ID NO: 67           moltype = AA  length = 22
FEATURE                 Location/Qualifiers
REGION                  1..22
                        note = Hepcidin peptide analogue
MOD_RES                 1
                        note = Xaa is pyroglutamic acid
source                  1..22
                        mol_type = protein
                        organism = synthetic construct
SEQUENCE: 67
XTHFPICIFV CHRSKGCYRR CR                                          22

SEQ ID NO: 68           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 68
DTHFPICIFK PRSKGWVCM                                              19

SEQ ID NO: 69           moltype = AA  length = 24
FEATURE                 Location/Qualifiers
REGION                  1..24
                        note = Hepcidin peptide analogue
source                  1..24
                        mol_type = protein
                        organism = synthetic construct
SEQUENCE: 69
DTHFPICIFV CGHRSKGCYM RCKT                                        24

SEQ ID NO: 70           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 70
DAHFPICIFG PRSKGWVCM                                              19

SEQ ID NO: 71           moltype = AA  length = 21
FEATURE                 Location/Qualifiers
REGION                  1..21
                        note = Hepcidin peptide analogue
```

```
source                    1..21
                          mol_type = protein
                          organism = synthetic construct
SEQUENCE: 71
DTHFPICIFV CYRGICYRRC R                                                   21

SEQ ID NO: 72             moltype = AA  length = 19
FEATURE                   Location/Qualifiers
REGION                    1..19
                          note = Hepcidin peptide analogue
source                    1..19
                          mol_type = protein
                          organism = synthetic construct
SEQUENCE: 72
DTHFPICIFG PRSKGWVCM                                                      19

SEQ ID NO: 73             moltype = AA  length = 18
FEATURE                   Location/Qualifiers
REGION                    1..18
                          note = Hepcidin peptide analogue
MOD_RES                   1
                          note = Xaa is beta-homoaspartic acid
source                    1..18
                          mol_type = protein
                          organism = synthetic construct
SEQUENCE: 73
XTHFPICIFG PRSKGWVC                                                       18

SEQ ID NO: 74             moltype = AA  length = 19
FEATURE                   Location/Qualifiers
REGION                    1..19
                          note = Hepcidin peptide analogue
source                    1..19
                          mol_type = protein
                          organism = synthetic construct
SEQUENCE: 74
DTHFPICIFG PRSKGWACM                                                      19

SEQ ID NO: 75             moltype = AA  length = 19
FEATURE                   Location/Qualifiers
REGION                    1..19
                          note = Hepcidin peptide analogue
MOD_RES                   1
                          note = Xaa is iminodiacetic acid
MOD_RES                   4
                          note = Xaa is beta,beta diphenylalanine
MOD_RES                   5
                          note = Xaa is beta-homoproline
MOD_RES                   9
                          note = Xaa is beta homophenylalanine
source                    1..19
                          mol_type = protein
                          organism = synthetic construct
SEQUENCE: 75
XTHXXRCRXG PRSKGWVCM                                                      19

SEQ ID NO: 76             moltype = AA  length = 9
FEATURE                   Location/Qualifiers
REGION                    1..9
                          note = Hepcidin peptide analogue
source                    1..9
                          mol_type = protein
                          organism = synthetic construct
SEQUENCE: 76
DTHFPCIRF                                                                 9

SEQ ID NO: 77             moltype = AA  length = 18
FEATURE                   Location/Qualifiers
REGION                    1..18
                          note = Hepcidin peptide analogue
source                    1..18
                          mol_type = protein
                          organism = synthetic construct
SEQUENCE: 77
THFPCIIFGP RSKGWVCM                                                       18

SEQ ID NO: 78             moltype = AA  length = 9
FEATURE                   Location/Qualifiers
REGION                    1..9
```

```
                        note = Hepcidin peptide analogue
source                  1..9
                        mol_type = protein
                        organism = synthetic construct
SEQUENCE: 78
DTHFPCIAF                                                                    9

SEQ ID NO: 79           moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 79
DAHFPCIIF                                                                    9

SEQ ID NO: 80           moltype = AA  length = 22
FEATURE                 Location/Qualifiers
REGION                  1..22
                        note = Hepcidin peptide analogue
source                  1..22
                        mol_type = protein
                        organism = synthetic construct
SEQUENCE: 80
DTHFPICIFV CHRPKGCYRR CP                                                    22

SEQ ID NO: 81           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 81
DTHFPICIFK PRSKGWVCM                                                        19

SEQ ID NO: 82           moltype = AA  length = 10
FEATURE                 Location/Qualifiers
REGION                  1..10
                        note = Hepcidin peptide analogue
source                  1..10
                        mol_type = protein
                        organism = synthetic construct
SEQUENCE: 82
DTHFPCIIFK                                                                  10

SEQ ID NO: 83           moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 83
DTHFPCIFF                                                                    9

SEQ ID NO: 84           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 84
DTHFPICIFG PRSKKWVCM                                                        19

SEQ ID NO: 85           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 85
DTHFPICIFG PRSKKWVCM                                                        19

SEQ ID NO: 86           moltype = AA  length = 17
FEATURE                 Location/Qualifiers
```

```
REGION                  1..17
                        note = Hepcidin peptide analogue
source                  1..17
                        mol_type = protein
                        organism = synthetic construct
SEQUENCE: 86
DTHFPICIFC PWGMCCK                                                    17

SEQ ID NO: 87           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 87
DTAFPICIFG PRSKGWVCM                                                  19

SEQ ID NO: 88           moltype = AA  length = 22
FEATURE                 Location/Qualifiers
REGION                  1..22
                        note = Hepcidin peptide analogue
source                  1..22
                        mol_type = protein
                        organism = synthetic construct
SEQUENCE: 88
DTHFPICIFV CYRGICYMRC KT                                              22

SEQ ID NO: 89           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 89
DTHFPICIFG PRSKGAVCM                                                  19

SEQ ID NO: 90           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 90
DTHFPICIAG PRSKGWVCM                                                  19

SEQ ID NO: 91           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 91
DTHFPICAFG PRSKGWVCM                                                  19

SEQ ID NO: 92           moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 92
DTHFPIAIFG PRSKGWVAM                                                  19

SEQ ID NO: 93           moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 93
DTHFPCRRFG PRSKGWVC                                                   18

SEQ ID NO: 94           moltype = AA  length = 18
```

```
FEATURE                 Location/Qualifiers
REGION                  1..18
                        note = Hepcidin peptide analogue
MOD_RES                 1
                        note = Xaa is iminodiacetic acid
MOD_RES                 5
                        note = Xaa is beta-homoproline
MOD_RES                 9
                        note = Xaa is beta-homophenylalanine
source                  1..18
                        mol_type = protein
                        organism = synthetic construct
SEQUENCE: 94
XTHFXCRRXG PRSKGWVC                                                        18

SEQ ID NO: 95           moltype =    length =
SEQUENCE: 95
000

SEQ ID NO: 96           moltype = AA   length = 22
FEATURE                 Location/Qualifiers
REGION                  1..22
                        note = Hepcidin peptide analogue
source                  1..22
                        mol_type = protein
                        organism = synthetic construct
SEQUENCE: 96
DTHFPCIIFV CHRSKGCYWA VC                                                   22

SEQ ID NO: 97           moltype = AA   length = 23
FEATURE                 Location/Qualifiers
REGION                  1..23
                        note = Hepcidin peptide analogue
source                  1..23
                        mol_type = protein
                        organism = synthetic construct
SEQUENCE: 97
DTHFPCIIFV CHRSKGCYWA VCF                                                  23

SEQ ID NO: 98           moltype = AA   length = 24
FEATURE                 Location/Qualifiers
REGION                  1..24
                        note = Hepcidin peptide analogue
source                  1..24
                        mol_type = protein
                        organism = synthetic construct
SEQUENCE: 98
DTHFPCIIFV CHRSKGCYWA VCFW                                                 24

SEQ ID NO: 99           moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 99
DTHFPICIFK PRSKGWVCM                                                       19

SEQ ID NO: 100          moltype =    length =
SEQUENCE: 100
000

SEQ ID NO: 101          moltype = AA   length = 19
FEATURE                 Location/Qualifiers
REGION                  1..19
                        note = Hepcidin peptide analogue
MOD_RES                 4
                        note = Xaa is beta,beta diphenylalanine
source                  1..19
                        mol_type = protein
                        organism = synthetic construct
SEQUENCE: 101
DTHXPCIIFG PRSRGWVCK                                                       19

SEQ ID NO: 102          moltype = AA   length = 19
FEATURE                 Location/Qualifiers
REGION                  1..19
                        note = Hepcidin peptide analogue
```

```
MOD_RES               5
                      note = Xaa is beta-homoproline
source                1..19
                      mol_type = protein
                      organism = synthetic construct
SEQUENCE: 102
DTHFXCIIFG PRSRGWVCK                                                   19

SEQ ID NO: 103        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 103
DTHFPCIIFG PRSRGWRCK                                                   19

SEQ ID NO: 104        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 104
DTHFPCIRFG PRSRGWVCK                                                   19

SEQ ID NO: 105        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 105
DTHFPCIRFG PRSRGWRCK                                                   19

SEQ ID NO: 106        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 106
DTHFPCIIFG PRSRGWVCK                                                   19

SEQ ID NO: 107        moltype = AA  length = 18
FEATURE               Location/Qualifiers
REGION                1..18
                      note = Hepcidin peptide analogue
source                1..18
                      mol_type = protein
                      organism = synthetic construct
SEQUENCE: 107
DTHFPCIIFG PRSRGVCK                                                    18

SEQ ID NO: 108        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 108
DTHFPCIYFG PRSKGWVCK                                                   19

SEQ ID NO: 109        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 109
DTHFPCIIFG PRSKGWVCK                                                   19

SEQ ID NO: 110        moltype = AA  length = 19
```

```
FEATURE               Location/Qualifiers
REGION                1..19
                      note = Hepcidin peptide analogue
source                1..19
                      mol_type = protein
                      organism = synthetic construct
SEQUENCE: 110
DTHFPCIIFG PRARGWVCK                                                   19

SEQ ID NO: 111        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 111
DTHFPCIIFG PRSRGWVCK                                                   19

SEQ ID NO: 112        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 112
DTHFPCIIFG PRSRGWVCK                                                   19

SEQ ID NO: 113        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 113
DTHFPICIFK PRSKGWVCK                                                   19

SEQ ID NO: 114        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 114
DTHFPCIIFG PRSKGWKCK                                                   19

SEQ ID NO: 115        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 115
DTHFPCIKFG PRSKGWKCK                                                   19

SEQ ID NO: 116        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 116
DTHFPCLIFG PRSKGWVCK                                                   19

SEQ ID NO: 117        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 117
DTHFPCVIFG PRSKGWVCK                                                   19
```

```
SEQ ID NO: 118            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 118
DTHFPCSIFG PRSKGWVCK                                                      19

SEQ ID NO: 119            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 119
DTHFPCQIFG PRSKGWVCK                                                      19

SEQ ID NO: 120            moltype = AA   length = 18
FEATURE                   Location/Qualifiers
REGION                    1..18
                          note = Hepcidin peptide analogue
source                    1..18
                          mol_type = protein
                          organism = synthetic construct
SEQUENCE: 120
THFPCIIFGP RSKGWVCK                                                       18

SEQ ID NO: 121            moltype = AA   length = 18
FEATURE                   Location/Qualifiers
REGION                    1..18
                          note = Hepcidin peptide analogue
source                    1..18
                          mol_type = protein
                          organism = synthetic construct
SEQUENCE: 121
THFPCIIFGP RSKGWVCK                                                       18

SEQ ID NO: 122            moltype = AA   length = 17
FEATURE                   Location/Qualifiers
REGION                    1..17
                          note = Hepcidin peptide analogue
source                    1..17
                          mol_type = protein
                          organism = synthetic construct
SEQUENCE: 122
HFPCIIFGPR SKGWVCK                                                        17

SEQ ID NO: 123            moltype = AA   length = 17
FEATURE                   Location/Qualifiers
REGION                    1..17
                          note = Hepcidin peptide analogue
source                    1..17
                          mol_type = protein
                          organism = synthetic construct
SEQUENCE: 123
HFPCIIFGPR SKGWVCK                                                        17

SEQ ID NO: 124            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 124
DTHFPCISFG PRSKGWVCK                                                      19

SEQ ID NO: 125            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 125
DTHFPCIKFG PRSKGWVCK                                                      19
```

```
SEQ ID NO: 126          moltype = AA   length = 20
FEATURE                 Location/Qualifiers
REGION                  1..20
                        note = Hepcidin peptide analogue
source                  1..20
                        mol_type = protein
                        organism = synthetic construct
SEQUENCE: 126
EDTHFPCIIF GPRSKGWVCK                                               20

SEQ ID NO: 127          moltype =    length =
SEQUENCE: 127
000

SEQ ID NO: 128          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 128
DTHFPCIIFE PRSKGWVCK                                                19

SEQ ID NO: 129          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 129
DTHFPCIIFS PRSKGWVCK                                                19

SEQ ID NO: 130          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 130
DTHFSCIIFG PRSKGWVCK                                                19

SEQ ID NO: 131          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 131
DTHFPCIIFG PRSRGWVCK                                                19

SEQ ID NO: 132          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 132
DTHFPCIIFG PRSRGWVCK                                                19

SEQ ID NO: 133          moltype = AA   length = 19
FEATURE                 Location/Qualifiers
REGION                  1..19
                        note = Hepcidin peptide analogue
MOD_RES                 1
                        note = Xaa is iminodiacetic acid
source                  1..19
                        mol_type = protein
                        organism = synthetic construct
SEQUENCE: 133
XTHFPCIIFG PRSRGWVCK                                                19

SEQ ID NO: 134          moltype = AA   length = 19
FEATURE                 Location/Qualifiers
```

```
REGION                  1..19
                        note = Hepcidin peptide analogue
source                  1..19
                        mol_type = protein
                        organism = synthetic construct
SEQUENCE: 134
DTHFPCIIFG PKSKGWVCK                                                    19

SEQ ID NO: 135          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 135
DTHFPCIKFG PKSKGWVCK                                                    19

SEQ ID NO: 136          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 136
DTHFPCIIFG PRSKGWCK                                                     18

SEQ ID NO: 137          moltype = AA  length = 17
FEATURE                 Location/Qualifiers
REGION                  1..17
                        note = Hepcidin peptide analogue
source                  1..17
                        mol_type = protein
                        organism = synthetic construct
SEQUENCE: 137
DTHFPCIIFG PRSKGVC                                                      17

SEQ ID NO: 138          moltype = AA  length = 17
FEATURE                 Location/Qualifiers
REGION                  1..17
                        note = Hepcidin peptide analogue
source                  1..17
                        mol_type = protein
                        organism = synthetic construct
SEQUENCE: 138
DTHFPCIIFG PRSKGCK                                                      17

SEQ ID NO: 139          moltype =    length =
SEQUENCE: 139
000

SEQ ID NO: 140          moltype = AA  length = 19
FEATURE                 Location/Qualifiers
REGION                  1..19
                        note = Hepcidin peptide analogue
MOD_RES                 7
                        note = Xaa is 2,3 diaminopropanoic acid
source                  1..19
                        mol_type = protein
                        organism = synthetic construct
SEQUENCE: 140
DTHFPCXIFG PRSKGWDCK                                                    19

SEQ ID NO: 141          moltype = AA  length = 19
FEATURE                 Location/Qualifiers
REGION                  1..19
                        note = Hepcidin peptide analogue
MOD_RES                 8
                        note = Xaa is 2,3 diaminopropanoic acid
source                  1..19
                        mol_type = protein
                        organism = synthetic construct
SEQUENCE: 141
DTHFPCIXFG PRSKGWDCK                                                    19

SEQ ID NO: 142          moltype = AA  length = 19
FEATURE                 Location/Qualifiers
REGION                  1..19
```

```
                    note = Hepcidin peptide analogue
MOD_RES             7
                    note = Xaa is 2,3 diaminopropanoic acid
source              1..19
                    mol_type = protein
                    organism = synthetic construct
SEQUENCE: 142
DTHFPCXIFG PRSKGWECK                                                    19

SEQ ID NO: 143      moltype = AA   length = 19
FEATURE             Location/Qualifiers
REGION              1..19
                    note = Hepcidin peptide analogue
MOD_RES             8
                    note = Xaa is 2,3 diaminopropanoic acid
source              1..19
                    mol_type = protein
                    organism = synthetic construct
SEQUENCE: 143
DTHFPCIXFG PRSKGWECK                                                    19

SEQ ID NO: 144      moltype = AA   length = 19
FEATURE             Location/Qualifiers
REGION              1..19
                    note = Hepcidin peptide analogue
source              1..19
                    mol_type = protein
                    organism = synthetic construct
SEQUENCE: 144
DTHFPCIKFG PRSKGWECK                                                    19

SEQ ID NO: 145      moltype = AA   length = 19
FEATURE             Location/Qualifiers
REGION              1..19
                    note = Hepcidin peptide analogue
source              1..19
                    mol_type = protein
                    organism = synthetic construct
SEQUENCE: 145
DTHFGCIIFG PRSKGWVCK                                                    19

SEQ ID NO: 146      moltype = AA   length = 19
FEATURE             Location/Qualifiers
REGION              1..19
                    note = Hepcidin peptide analogue
source              1..19
                    mol_type = protein
                    organism = synthetic construct
SEQUENCE: 146
DTHFGCIIFG PRSKGWVCK                                                    19

SEQ ID NO: 147      moltype = AA   length = 19
FEATURE             Location/Qualifiers
REGION              1..19
                    note = Hepcidin peptide analogue
source              1..19
                    mol_type = protein
                    organism = synthetic construct
SEQUENCE: 147
DTHFRCIIFG PRSKGWVCK                                                    19

SEQ ID NO: 148      moltype = AA   length = 19
FEATURE             Location/Qualifiers
REGION              1..19
                    note = Hepcidin peptide analogue
source              1..19
                    mol_type = protein
                    organism = synthetic construct
SEQUENCE: 148
DTHFRCIIFG PRSKGWVCK                                                    19

SEQ ID NO: 149      moltype = AA   length = 19
FEATURE             Location/Qualifiers
REGION              1..19
                    note = Hepcidin peptide analogue
MOD_RES             5
                    note = Xaa is sarcosine
source              1..19
                    mol_type = protein
```

```
                                                organism = synthetic construct
SEQUENCE: 149
DTHFXCIIFG PRSKGWVCK                                                                    19

SEQ ID NO: 150          moltype = AA   length = 19
FEATURE                 Location/Qualifiers
REGION                  1..19
                        note = Hepcidin peptide analogue
MOD_RES                 5
                        note = Xaa is sarcosine
source                  1..19
                        mol_type = protein
                        organism = synthetic construct
SEQUENCE: 150
DTHFXCIIFG PRSKGWVCK                                                                    19

SEQ ID NO: 151          moltype = AA   length = 19
FEATURE                 Location/Qualifiers
REGION                  1..19
                        note = Hepcidin peptide analogue
MOD_RES                 5
                        note = Xaa is beta-alanine
source                  1..19
                        mol_type = protein
                        organism = synthetic construct
SEQUENCE: 151
DTHFXCIIFG PRSKGWVCK                                                                    19

SEQ ID NO: 152          moltype = AA   length = 19
FEATURE                 Location/Qualifiers
REGION                  1..19
                        note = Hepcidin peptide analogue
MOD_RES                 5
                        note = Xaa is beta-alanine
source                  1..19
                        mol_type = protein
                        organism = synthetic construct
SEQUENCE: 152
DTHFXCIIFG PRSKGWVCK                                                                    19

SEQ ID NO: 153          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 153
DTHFKCIIFG PRSKGWVCK                                                                    19

SEQ ID NO: 154          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 154
DTHFKCIIFG PRSKGWVCK                                                                    19

SEQ ID NO: 155          moltype = AA   length = 18
FEATURE                 Location/Qualifiers
REGION                  1..18
                        note = Hepcidin peptide analogue
source                  1..18
                        mol_type = protein
                        organism = synthetic construct
SEQUENCE: 155
THFPCIIFGP RSKGWVCM                                                                     18

SEQ ID NO: 156          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 156
HFPCIIFGPR SKGWVCM                                                                      17
```

```
SEQ ID NO: 157          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 157
HFPCIIFGPR SKGWVCM                                                          17

SEQ ID NO: 158          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 158
DTHFPCISFG PRSKGWVCM                                                        19

SEQ ID NO: 159          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 159
DTHFPCIKFG PRSKGWVCM                                                        19

SEQ ID NO: 160          moltype = AA   length = 20
FEATURE                 Location/Qualifiers
REGION                  1..20
                        note = Hepcidin peptide analogue
source                  1..20
                        mol_type = protein
                        organism = synthetic construct
SEQUENCE: 160
EDTHFPCIIF GPRSKGWVCM                                                       20

SEQ ID NO: 161          moltype =    length =
SEQUENCE: 161
000

SEQ ID NO: 162          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 162
DTHFPCIIFE PRSKGWVCM                                                        19

SEQ ID NO: 163          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 163
DTHFKCIEFG PRSKGWVCK                                                        19

SEQ ID NO: 164          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 164
DTHFPCIIFG PRSKGWACK                                                        19

SEQ ID NO: 165          moltype = AA   length = 19
FEATURE                 Location/Qualifiers
REGION                  1..19
                        note = Hepcidin peptide analogue
```

```
source                  1..19
                        mol_type = protein
                        organism = synthetic construct
SEQUENCE: 165
DTHFPCIIFE PRSKGWVCK                                                    19

SEQ ID NO: 166          moltype = AA   length = 22
FEATURE                 Location/Qualifiers
REGION                  1..22
                        note = Hepcidin peptide analogue
source                  1..22
                        mol_type = protein
                        organism = synthetic construct
SEQUENCE: 166
DTHFPCIIFG PRSKGWVCKK KK                                                22

SEQ ID NO: 167          moltype = AA   length = 22
FEATURE                 Location/Qualifiers
REGION                  1..22
                        note = Hepcidin peptide analogue
source                  1..22
                        mol_type = protein
                        organism = synthetic construct
SEQUENCE: 167
DTHFPCIIFE PRSKGWVCKK KK                                                22

SEQ ID NO: 168          moltype = AA   length = 20
FEATURE                 Location/Qualifiers
REGION                  1..20
                        note = Hepcidin peptide analogue
source                  1..20
                        mol_type = protein
                        organism = synthetic construct
SEQUENCE: 168
DTHFPCIIFG PRSKGWVCKK                                                   20

SEQ ID NO: 169          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 169
DTAFPCIIFG PRSKGWVCK                                                    19

SEQ ID NO: 170          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 170
DTKFPCIIFG PRSKGWVCK                                                    19

SEQ ID NO: 171          moltype = AA   length = 23
FEATURE                 Location/Qualifiers
REGION                  1..23
                        note = Hepcidin peptide analogue
source                  1..23
                        mol_type = protein
                        organism = synthetic construct
SEQUENCE: 171
DTHFPCIIFV CHRPKGCYRR VCR                                               23

SEQ ID NO: 172          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 172
DTHFPCIKFG PRSKGWVCK                                                    19

SEQ ID NO: 173          moltype = AA   length = 19
FEATURE                 Location/Qualifiers
REGION                  1..19
```

```
                        note = Hepcidin peptide analogue
source                  1..19
                        mol_type = protein
                        organism = synthetic construct
SEQUENCE: 173
DTHFPCIKFK PRSKGWVCK                                                19

SEQ ID NO: 174          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 174
DTHFPCIKFG PKSKGWVCK                                                19

SEQ ID NO: 175          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 175
DTHFPCIKFG PRSKGWVCK                                                19

SEQ ID NO: 176          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 176
DTHFPCIKFG PRSKGWVCK                                                19

SEQ ID NO: 177          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 177
DTHFPCIKFG PRSKGWTCK                                                19

SEQ ID NO: 178          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 178
DTHFPCIEFG PRSKGWTCK                                                19

SEQ ID NO: 179          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 179
DTHFPICIFG PRSKGWVC                                                 18

SEQ ID NO: 180          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 180
DTHFPCIKFG PRSKGWVCK                                                19

SEQ ID NO: 181          moltype = AA  length = 19
FEATURE                 Location/Qualifiers
```

```
REGION                    1..19
                          note = Hepcidin peptide analogue
source                    1..19
                          mol_type = protein
                          organism = synthetic construct
SEQUENCE: 181
DTHFPCIKFG PRSKGWVCK                                                   19

SEQ ID NO: 182            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 182
DTHFPCIKFG PRSKGWVCK                                                   19

SEQ ID NO: 183            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 183
DTHFPCIKFG PRSKGWVCK                                                   19

SEQ ID NO: 184            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 184
DTHFPCIKFG PRSKGWVCK                                                   19

SEQ ID NO: 185            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 185
DTHFPCIKFG PRSKGWVCK                                                   19

SEQ ID NO: 186            moltype = AA   length = 19
FEATURE                   Location/Qualifiers
REGION                    1..19
                          note = Hepcidin peptide analogue
source                    1..19
                          mol_type = protein
                          organism = synthetic construct
SEQUENCE: 186
DTHFPCIKFG PRSKGWVCK                                                   19

SEQ ID NO: 187            moltype = AA   length = 20
FEATURE                   Location/Qualifiers
REGION                    1..20
                          note = Hepcidin peptide analogue
source                    1..20
                          mol_type = protein
                          organism = synthetic construct
SEQUENCE: 187
VDTHFPCIKF GPRSKGWVCK                                                  20

SEQ ID NO: 188            moltype = AA   length = 20
FEATURE                   Location/Qualifiers
REGION                    1..20
                          note = Hepcidin peptide analogue
source                    1..20
                          mol_type = protein
                          organism = synthetic construct
SEQUENCE: 188
LDTHFPCIKF GPRSKGWVCK                                                  20

SEQ ID NO: 189            moltype = AA   length = 19
```

```
FEATURE              Location/Qualifiers
REGION               1..19
                     note = Hepcidin peptide analogue
source               1..19
                     mol_type = protein
                     organism = synthetic construct
SEQUENCE: 189
DTHFPCIKFG PRSKGWVCK                                                    19

SEQ ID NO: 190       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 190
DTHFPCIKFG PRSKGWVCK                                                    19

SEQ ID NO: 191       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 191
DTHFPCIKFG PRSKGWVCK                                                    19

SEQ ID NO: 192       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 192
DTHFPCIKFG PRSKGWVCK                                                    19

SEQ ID NO: 193       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 193
DTHFPCIKFG PRSKGWVCK                                                    19

SEQ ID NO: 194       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 194
DTHFPCIIFG PRSKGWKCK                                                    19

SEQ ID NO: 195       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 195
DTHFPCIIFG PRSKGWECK                                                    19

SEQ ID NO: 196       moltype = AA  length = 19
FEATURE              Location/Qualifiers
REGION               1..19
                     note = Hepcidin peptide analogue
source               1..19
                     mol_type = protein
                     organism = synthetic construct
SEQUENCE: 196
DTHFPCRRFG PRSKGWVCK                                                    19
```

```
SEQ ID NO: 197          moltype =    length =
SEQUENCE: 197
000

SEQ ID NO: 198          moltype =    length =
SEQUENCE: 198
000

SEQ ID NO: 199          moltype = AA   length = 18
FEATURE                 Location/Qualifiers
REGION                  1..18
                        note = Hepcidin peptide analogue
source                  1..18
                        mol_type = protein
                        organism = synthetic construct
SEQUENCE: 199
DTHFPICIFG PRSKGWVC                                              18

SEQ ID NO: 200          moltype = AA   length = 18
FEATURE                 Location/Qualifiers
REGION                  1..18
                        note = Hepcidin peptide analogue
source                  1..18
                        mol_type = protein
                        organism = synthetic construct
SEQUENCE: 200
DTHFPICIFG PRSKGWVC                                              18

SEQ ID NO: 201          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 201
DTHFPCIIFG PRSRGWVCK                                             19

SEQ ID NO: 202          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 202
DTHFPCIIFG PRSRGWVCK                                             19

SEQ ID NO: 203          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 203
DTHFPCIIFG PRSRGWVCK                                             19

SEQ ID NO: 204          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 204
DTHFPCIKFE PRSKGWVCK                                             19

SEQ ID NO: 205          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 205
DTHFPCIKFE PRSKGWTCK                                             19

SEQ ID NO: 206          moltype = AA   length = 18
```

```
FEATURE              Location/Qualifiers
REGION               1..18
                     note = Hepcidin peptide analogue
source               1..18
                     mol_type = protein
                     organism = synthetic construct
SEQUENCE: 206
DTHFPCIKFE PRSKGWCK                                                        18

SEQ ID NO: 207       moltype = AA  length = 17
FEATURE              Location/Qualifiers
REGION               1..17
                     note = Hepcidin peptide analogue
source               1..17
                     mol_type = protein
                     organism = synthetic construct
SEQUENCE: 207
DTHFPCIKFE PRSKGCK                                                         17

SEQ ID NO: 208       moltype = AA  length = 16
FEATURE              Location/Qualifiers
REGION               1..16
                     note = Hepcidin peptide analogue
source               1..16
                     mol_type = protein
                     organism = synthetic construct
SEQUENCE: 208
DTHFPCIFEP RSKGCK                                                          16

SEQ ID NO: 209       moltype = AA  length = 17
FEATURE              Location/Qualifiers
REGION               1..17
                     note = Hepcidin peptide analogue
source               1..17
                     mol_type = protein
                     organism = synthetic construct
SEQUENCE: 209
DTHFPCIFEP RSKGWCK                                                         17

SEQ ID NO: 210       moltype = AA  length = 16
FEATURE              Location/Qualifiers
REGION               1..16
                     note = Hepcidin peptide analogue
source               1..16
                     mol_type = protein
                     organism = synthetic construct
SEQUENCE: 210
DTHFPCIKFG PRSKCK                                                          16

SEQ ID NO: 211       moltype = AA  length = 15
FEATURE              Location/Qualifiers
REGION               1..15
                     note = Hepcidin peptide analogue
source               1..15
                     mol_type = protein
                     organism = synthetic construct
SEQUENCE: 211
DTHFPCIKFG PRSCK                                                           15

SEQ ID NO: 212       moltype = AA  length = 14
FEATURE              Location/Qualifiers
REGION               1..14
                     note = Hepcidin peptide analogue
source               1..14
                     mol_type = protein
                     organism = synthetic construct
SEQUENCE: 212
DTHFPCIKFG PRCK                                                            14

SEQ ID NO: 213       moltype = AA  length = 13
FEATURE              Location/Qualifiers
REGION               1..13
                     note = Hepcidin peptide analogue
source               1..13
                     mol_type = protein
                     organism = synthetic construct
SEQUENCE: 213
DTHFPCIKFG PCK                                                             13
```

| | | |
|---|---|---|
| SEQ ID NO: 214<br>FEATURE<br>REGION<br><br>source | moltype = AA  length = 12<br>Location/Qualifiers<br>1..12<br>note = Hepcidin peptide analogue<br>1..12<br>mol_type = protein<br>organism = synthetic construct | |
| SEQUENCE: 214<br>DTHFPCIKFG CK | | 12 |
| SEQ ID NO: 215<br>FEATURE<br>REGION<br><br>source | moltype = AA  length = 11<br>Location/Qualifiers<br>1..11<br>note = Hepcidin peptide analogue<br>1..11<br>mol_type = protein<br>organism = synthetic construct | |
| SEQUENCE: 215<br>DTHFPCIKFC K | | 11 |
| SEQ ID NO: 216<br>FEATURE<br>REGION<br><br>source | moltype = AA  length = 10<br>Location/Qualifiers<br>1..10<br>note = Hepcidin peptide analogue<br>1..10<br>mol_type = protein<br>organism = synthetic construct | |
| SEQUENCE: 216<br>DTHFPCIKFC | | 10 |
| SEQ ID NO: 217<br>FEATURE<br>REGION<br><br>source | moltype = AA  length = 19<br>Location/Qualifiers<br>1..19<br>note = Hepcidin peptide analogue<br>1..19<br>mol_type = protein<br>organism = synthetic construct | |
| SEQUENCE: 217<br>DTHFPCIKFG PRSKGWVCK | | 19 |
| SEQ ID NO: 218<br>FEATURE<br>REGION<br><br>source | moltype = AA  length = 20<br>Location/Qualifiers<br>1..20<br>note = Hepcidin peptide analogue<br>1..20<br>mol_type = protein<br>organism = synthetic construct | |
| SEQUENCE: 218<br>DTHFPCIKFK APRSKGWVCK | | 20 |
| SEQ ID NO: 219<br>FEATURE<br>REGION<br><br>source | moltype = AA  length = 20<br>Location/Qualifiers<br>1..20<br>note = Hepcidin peptide analogue<br>1..20<br>mol_type = protein<br>organism = synthetic construct | |
| SEQUENCE: 219<br>DTHFPCIKFG PKASKGWVCK | | 20 |
| SEQ ID NO: 220<br>FEATURE<br>REGION<br><br>source | moltype = AA  length = 20<br>Location/Qualifiers<br>1..20<br>note = Hepcidin peptide analogue<br>1..20<br>mol_type = protein<br>organism = synthetic construct | |
| SEQUENCE: 220<br>DTHFPCIKFG PRSKAGWVCK | | 20 |
| SEQ ID NO: 221<br>FEATURE<br>REGION<br><br>source | moltype = AA  length = 20<br>Location/Qualifiers<br>1..20<br>note = Hepcidin peptide analogue<br>1..20<br>mol_type = protein<br>organism = synthetic construct | |
| SEQUENCE: 221<br>DTHFPCIKFG PRSKGWVCKA | | 20 |

```
SEQ ID NO: 222          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 222
DTHFPCIKFG PRSKGWVCK                                                   19

SEQ ID NO: 223          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 223
DTHFPCIKFK PRSKGWVCK                                                   19

SEQ ID NO: 224          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 224
DTHFPCIKFG PKSKGWVCK                                                   19

SEQ ID NO: 225          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 225
DTHFPCIKFG PRSKGWVCK                                                   19

SEQ ID NO: 226          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 226
DTHFPCIKFG PRSKGWVCK                                                   19

SEQ ID NO: 227          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 227
DTHFPCIKFG PRSKGWVCK                                                   19

SEQ ID NO: 228          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 228
DTHFPCIKFK PRSKGWVCK                                                   19

SEQ ID NO: 229          moltype = AA   length = 19
FEATURE                 Location/Qualifiers
REGION                  1..19
                        note = Hepcidin peptide analogue
source                  1..19
                        mol_type = protein
                        organism = synthetic construct
SEQUENCE: 229
```

DTHFPCIKFG PKSKGWVCK 19

```
SEQ ID NO: 230        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 230
DTHFPCIKFG PRSKGWVCK                                                19

SEQ ID NO: 231        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 231
DTHFPCIKFG PRSKGWVCK                                                19

SEQ ID NO: 232        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 232
DTHFPCIKFG PRSKGWVCK                                                19

SEQ ID NO: 233        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 233
DTHFPCIKFK PRSKGWVCK                                                19

SEQ ID NO: 234        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 234
DTHFPCIKFG PKSKGWVCK                                                19

SEQ ID NO: 235        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 235
DTHFPCIKFG PRSKGWVCK                                                19

SEQ ID NO: 236        moltype = AA  length = 19
FEATURE               Location/Qualifiers
REGION                1..19
                      note = Hepcidin peptide analogue
source                1..19
                      mol_type = protein
                      organism = synthetic construct
SEQUENCE: 236
DTHFPCIKFG PRSKGWVCK                                                19

SEQ ID NO: 237        moltype = AA  length = 19
FEATURE               Location/Qualifiers
REGION                1..19
                      note = Hepcidin peptide analogue
source                1..19
                      mol_type = protein
                      organism = synthetic construct
```

```
SEQUENCE: 237
DTHFPCIKFE PRSKKWVCK                                                       19

SEQ ID NO: 238           moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 238
DTHFPCIKFG PRSKGWVCK                                                       19

SEQ ID NO: 239           moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 239
DTHFPCIKFG PRSKGWVCK                                                       19

SEQ ID NO: 240           moltype = AA  length = 19
FEATURE                  Location/Qualifiers
REGION                   1..19
                         note = Hepcidin peptide analogue
source                   1..19
                         mol_type = protein
                         organism = synthetic construct
SEQUENCE: 240
DTHFPCIKFG PRSKGWVCK                                                       19

SEQ ID NO: 241           moltype = AA  length = 17
FEATURE                  Location/Qualifiers
REGION                   1..17
                         note = Hepcidin peptide analogue
source                   1..17
                         mol_type = protein
                         organism = synthetic construct
SEQUENCE: 241
DTHFPCIKFE PRSKGCK                                                         17

SEQ ID NO: 242           moltype = AA  length = 17
FEATURE                  Location/Qualifiers
REGION                   1..17
                         note = Hepcidin peptide analogue
source                   1..17
                         mol_type = protein
                         organism = synthetic construct
SEQUENCE: 242
DTHFPCIKFK PRSKGCK                                                         17

SEQ ID NO: 243           moltype = AA  length = 17
FEATURE                  Location/Qualifiers
REGION                   1..17
                         note = Hepcidin peptide analogue
source                   1..17
                         mol_type = protein
                         organism = synthetic construct
SEQUENCE: 243
DTHFPCIKFE PKSKGCK                                                         17

SEQ ID NO: 244           moltype = AA  length = 17
FEATURE                  Location/Qualifiers
REGION                   1..17
                         note = Hepcidin peptide analogue
source                   1..17
                         mol_type = protein
                         organism = synthetic construct
SEQUENCE: 244
DTHFPCIKFE PRSKGCK                                                         17

SEQ ID NO: 245           moltype = AA  length = 17
FEATURE                  Location/Qualifiers
REGION                   1..17
                         note = Hepcidin peptide analogue
source                   1..17
                         mol_type = protein
```

```
SEQUENCE: 245
DTHFPCIKFE PRSKKCK                                                                17

SEQ ID NO: 246          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 246
DTHFPCIKFE PRSKGCK                                                                17

SEQ ID NO: 247          moltype = AA   length = 18
FEATURE                 Location/Qualifiers
REGION                  1..18
                        note = Hepcidin peptide analogue
source                  1..18
                        mol_type = protein
                        organism = synthetic construct
SEQUENCE: 247
DTHFPCIKFE PRSKGCKK                                                               18

SEQ ID NO: 248          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 248
DTHFPCIKFE PRSKGCK                                                                17

SEQ ID NO: 249          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 249
DTHFPCIKFK PRSKGCK                                                                17

SEQ ID NO: 250          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 250
DTHFPCIKFE PKSKGCK                                                                17

SEQ ID NO: 251          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 251
DTHFPCIKFE PRSKGCK                                                                17

SEQ ID NO: 252          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 252
DTHFPCIKFE PRSKKCK                                                                17

SEQ ID NO: 253          moltype = AA   length = 18
FEATURE                 Location/Qualifiers
REGION                  1..18
                        note = Hepcidin peptide analogue
source                  1..18
```

```
                        mol_type = protein
                        organism = synthetic construct
SEQUENCE: 253
DTHFPCIKFE PRSKGCKK                                                 18

SEQ ID NO: 254          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 254
DTHFPCIKFE PRSKGCKK                                                 18

SEQ ID NO: 255          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 255
DTHFPCIKFG PRSKGWVCK                                                19

SEQ ID NO: 256          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 256
AAHFPCIKFG PRSKGWVCK                                                19

SEQ ID NO: 257          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 257
ATHFPCIKFG PRSKGWVCK                                                19

SEQ ID NO: 258          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 258
DAHFPCIKFG PRSKGWVCK                                                19

SEQ ID NO: 259          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 259
DTHAPCIKFG PRSKGWVCK                                                19

SEQ ID NO: 260          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 260
DTHFPCIKAG PRSKGWVCK                                                19

SEQ ID NO: 261          moltype = AA  length = 19
FEATURE                 Location/Qualifiers
REGION                  1..19
                        note = Hepcidin peptide analogue
```

```
source                  1..19
                        mol_type = protein
                        organism = synthetic construct
SEQUENCE: 261
DTHFPCIKFE PRSKGWVCK                                                  19

SEQ ID NO: 262          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 262
DTHFPCIKFE PRSKGWECK                                                  19

SEQ ID NO: 263          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 263
DTHFPCIIFE PRSKGWEC                                                   18

SEQ ID NO: 264          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 264
DTHFPCIKFK PRSKGWECK                                                  19

SEQ ID NO: 265          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 265
DTHFPCIKFE PKSKGWECK                                                  19

SEQ ID NO: 266          moltype = AA  length = 19
FEATURE                 Location/Qualifiers
REGION                  1..19
                        note = Hepcidin peptide analogue
source                  1..19
                        mol_type = protein
                        organism = synthetic construct
SEQUENCE: 266
DTHAPCIKFE PRSKGWECK                                                  19

SEQ ID NO: 267          moltype = AA  length = 17
FEATURE                 Location/Qualifiers
REGION                  1..17
                        note = Hepcidin peptide analogue
MOD_RES                 1
                        note = Xaa is iminodiacetic acid
source                  1..17
                        mol_type = protein
                        organism = synthetic construct
SEQUENCE: 267
XTHFPCIKFE PRSKKCK                                                    17

SEQ ID NO: 268          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 268
DTHFPCIKFE PRSKGWEC                                                   18

SEQ ID NO: 269          moltype = AA  length = 19
```

```
FEATURE                 Location/Qualifiers
REGION                  1..19
                        note = Hepcidin peptide analogue
source                  1..19
                        mol_type = protein
                        organism = synthetic construct
SEQUENCE: 269
DTHFPCIKFG PRSKGWVCK                                                        19

SEQ ID NO: 270          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 270
DTHFPCIKFK PRSKGWVC                                                         18

SEQ ID NO: 271          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 271
DTHFPCIKFK PRSKGWVC                                                         18

SEQ ID NO: 272          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 272
DTHFPCIKFK PRSKGWVC                                                         18

SEQ ID NO: 273          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 273
DTHFPCIKFK PRSKGWVC                                                         18

SEQ ID NO: 274          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 274
DTHFPCIKFK PRSKGWVC                                                         18

SEQ ID NO: 275          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 275
DTHFPCIKFK PRSKGWVC                                                         18

SEQ ID NO: 276          moltype = AA  length = 18
FEATURE                 Location/Qualifiers
REGION                  1..18
                        note = Hepcidin peptide analogue
source                  1..18
                        mol_type = protein
                        organism = synthetic construct
SEQUENCE: 276
DTHFPCIKFK PRSKGWVC                                                         18
```

```
SEQ ID NO: 277           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
                         mol_type = protein
                         organism = synthetic construct
SEQUENCE: 277
XTHFPCIKFE PRSKGWVCK                                                  19

SEQ ID NO: 278           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
                         mol_type = protein
                         organism = synthetic construct
SEQUENCE: 278
XTHFPCIKFE PRSKGWVCK                                                  19

SEQ ID NO: 279           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
                         mol_type = protein
                         organism = synthetic construct
SEQUENCE: 279
XTHFPCIKFE PRSKGWVCK                                                  19

SEQ ID NO: 280           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
                         mol_type = protein
                         organism = synthetic construct
SEQUENCE: 280
XTHFPCIKFE PRSKGWVCK                                                  19

SEQ ID NO: 281           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
                         mol_type = protein
                         organism = synthetic construct
SEQUENCE: 281
XTHFPCIKFE PRSKGWVCK                                                  19

SEQ ID NO: 282           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
                         mol_type = protein
                         organism = synthetic construct
SEQUENCE: 282
XTHFPCIKFE PRSKGWVCK                                                  19

SEQ ID NO: 283           moltype = AA   length = 19
FEATURE                  Location/Qualifiers
REGION                   1..19
                         note = Hepcidin peptide analogue
MOD_RES                  1
                         note = Xaa is iminodiacetic acid
source                   1..19
```

```
                        mol_type = protein
                        organism = synthetic construct
SEQUENCE: 283
XTHFPCIKFE PRSKGWVCK                                                19

SEQ ID NO: 284          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 284
HFPCIKFEPR SKGWVCK                                                  17

SEQ ID NO: 285          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 285
HFPCIKFEPR SKGWVCK                                                  17

SEQ ID NO: 286          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 286
DTHFPCIKFE PHSKGCK                                                  17

SEQ ID NO: 287          moltype = AA   length = 16
FEATURE                 Location/Qualifiers
REGION                  1..16
                        note = Hepcidin peptide analogue
source                  1..16
                        mol_type = protein
                        organism = synthetic construct
SEQUENCE: 287
DTHFPCIHFE PHSKGC                                                   16

SEQ ID NO: 288          moltype = AA   length = 17
FEATURE                 Location/Qualifiers
REGION                  1..17
                        note = Hepcidin peptide analogue
source                  1..17
                        mol_type = protein
                        organism = synthetic construct
SEQUENCE: 288
DTHFPCIKFE PHSKGCK                                                  17

SEQ ID NO: 289          moltype = AA   length = 16
FEATURE                 Location/Qualifiers
REGION                  1..16
                        note = Hepcidin peptide analogue
source                  1..16
                        mol_type = protein
                        organism = synthetic construct
SEQUENCE: 289
DTHFPCIKFE PREKEC                                                   16

SEQ ID NO: 290          moltype = AA   length = 16
FEATURE                 Location/Qualifiers
REGION                  1..16
                        note = Hepcidin peptide analogue
source                  1..16
                        mol_type = protein
                        organism = synthetic construct
SEQUENCE: 290
DTAFPCIKFE PRSKEC                                                   16

SEQ ID NO: 291          moltype = AA   length = 12
FEATURE                 Location/Qualifiers
REGION                  1..12
                        note = Hepcidin peptide analogue
```

```
source                 1..12
                       mol_type = protein
                       organism = synthetic construct
SEQUENCE: 291
DTHFPCIKFE CK                                                           12

SEQ ID NO: 292         moltype = AA   length = 15
FEATURE                Location/Qualifiers
REGION                 1..15
                       note = Hepcidin peptide analogue
source                 1..15
                       mol_type = protein
                       organism = synthetic construct
SEQUENCE: 292
DTHFPIAIFA AGICI                                                        15

SEQ ID NO: 293         moltype = AA   length = 14
FEATURE                Location/Qualifiers
REGION                 1..14
                       note = Hepcidin peptide analogue
source                 1..14
                       mol_type = protein
                       organism = synthetic construct
SEQUENCE: 293
DTHFPIAIFA AICI                                                         14

SEQ ID NO: 294         moltype = AA   length = 13
FEATURE                Location/Qualifiers
REGION                 1..13
                       note = Hepcidin peptide analogue
source                 1..13
                       mol_type = protein
                       organism = synthetic construct
SEQUENCE: 294
DTHFPIAIFA ICI                                                          13

SEQ ID NO: 295         moltype = AA   length = 12
FEATURE                Location/Qualifiers
REGION                 1..12
                       note = Hepcidin peptide analogue
source                 1..12
                       mol_type = protein
                       organism = synthetic construct
SEQUENCE: 295
DTHFPIAIFI CI                                                           12

SEQ ID NO: 296         moltype = AA   length = 11
FEATURE                Location/Qualifiers
REGION                 1..11
                       note = Hepcidin peptide analogue
source                 1..11
                       mol_type = protein
                       organism = synthetic construct
SEQUENCE: 296
DTHFPIAIIC I                                                            11

SEQ ID NO: 297         moltype = AA   length = 10
FEATURE                Location/Qualifiers
REGION                 1..10
                       note = Hepcidin peptide analogue
source                 1..10
                       mol_type = protein
                       organism = synthetic construct
SEQUENCE: 297
DTHFPIAICI                                                              10

SEQ ID NO: 298         moltype = AA   length = 9
FEATURE                Location/Qualifiers
REGION                 1..9
                       note = Hepcidin peptide analogue
source                 1..9
                       mol_type = protein
                       organism = synthetic construct
SEQUENCE: 298
DTHFPIICI                                                               9

SEQ ID NO: 299         moltype = AA   length = 9
FEATURE                Location/Qualifiers
REGION                 1..9
```

```
                      note = Hepcidin peptide analogue
source                1..9
                      mol_type = protein
                      organism = synthetic construct
SEQUENCE: 299
DTHICIAIF                                                                       9

SEQ ID NO: 300        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 300
DTHCPIAIF                                                                       9

SEQ ID NO: 301        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 301
DTHFPCIIA                                                                       9

SEQ ID NO: 302        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 302
DTHFPCAIF                                                                       9

SEQ ID NO: 303        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 303
DTHFACIIF                                                                       9

SEQ ID NO: 304        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 304
DTHFACIIF                                                                       9

SEQ ID NO: 305        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 305
DTHAPCIIF                                                                       9

SEQ ID NO: 306        moltype = AA  length = 9
FEATURE               Location/Qualifiers
REGION                1..9
                      note = Hepcidin peptide analogue
source                1..9
                      mol_type = protein
                      organism = synthetic construct
SEQUENCE: 306
DTAFPCIIF                                                                       9

SEQ ID NO: 307        moltype = AA  length = 9
FEATURE               Location/Qualifiers
```

```
REGION                    1..9
                          note = Hepcidin peptide analogue
source                    1..9
                          mol_type = protein
                          organism = synthetic construct
SEQUENCE: 307
ATHFPCIIF                                                                        9

SEQ ID NO: 308            moltype = AA  length = 9
FEATURE                   Location/Qualifiers
REGION                    1..9
                          note = Hepcidin peptide analogue
MOD_RES                   1
                          note = Xaa is iminodiacetic acid
MOD_RES                   5
                          note = Xaa is beta-homoproline
source                    1..9
                          mol_type = protein
                          organism = synthetic construct
SEQUENCE: 308
XTHFXCIIF                                                                        9

SEQ ID NO: 309            moltype =    length =
SEQUENCE: 309
000

SEQ ID NO: 310            moltype = AA  length = 9
FEATURE                   Location/Qualifiers
REGION                    1..9
                          note = Hepcidin peptide analogue
source                    1..9
                          mol_type = protein
                          organism = synthetic construct
SEQUENCE: 310
DTHFPCIEF                                                                        9

SEQ ID NO: 311            moltype = AA  length = 9
FEATURE                   Location/Qualifiers
REGION                    1..9
                          note = Hepcidin peptide analogue
source                    1..9
                          mol_type = protein
                          organism = synthetic construct
SEQUENCE: 311
DTHFPCIIF                                                                        9

SEQ ID NO: 312            moltype = AA  length = 9
FEATURE                   Location/Qualifiers
REGION                    1..9
                          note = Hepcidin peptide analogue
source                    1..9
                          mol_type = protein
                          organism = synthetic construct
SEQUENCE: 312
DTHFPAIIF                                                                        9

SEQ ID NO: 313            moltype = AA  length = 9
FEATURE                   Location/Qualifiers
REGION                    1..9
                          note = Hepcidin peptide analogue
source                    1..9
                          mol_type = protein
                          organism = synthetic construct
SEQUENCE: 313
DTHFPSIIF                                                                        9

SEQ ID NO: 314            moltype = AA  length = 9
FEATURE                   Location/Qualifiers
REGION                    1..9
                          note = Hepcidin peptide analogue
source                    1..9
                          mol_type = protein
                          organism = synthetic construct
SEQUENCE: 314
DTHFPCIKF                                                                        9

SEQ ID NO: 315            moltype =    length =
SEQUENCE: 315
000
```

```
SEQ ID NO: 316          moltype = AA  length = 8
FEATURE                 Location/Qualifiers
REGION                  1..8
                        note = Hepcidin peptide analogue
source                  1..8
                        mol_type = protein
                        organism = synthetic construct
SEQUENCE: 316
DTHFPCIF                                                                    8

SEQ ID NO: 317          moltype =    length =
SEQUENCE: 317
000

SEQ ID NO: 318          moltype =    length =
SEQUENCE: 318
000

SEQ ID NO: 319          moltype =    length =
SEQUENCE: 319
000

SEQ ID NO: 320          moltype = AA  length = 10
FEATURE                 Location/Qualifiers
REGION                  1..10
                        note = Hepcidin peptide analogue
source                  1..10
                        mol_type = protein
                        organism = synthetic construct
SEQUENCE: 320
DTHFPCIKFF                                                                 10

SEQ ID NO: 321          moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 321
YTHFPCIIF                                                                   9

SEQ ID NO: 322          moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 322
LTHFPCIIF                                                                   9

SEQ ID NO: 323          moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 323
ETHFPCIIF                                                                   9

SEQ ID NO: 324          moltype = AA  length = 9
FEATURE                 Location/Qualifiers
REGION                  1..9
                        note = Hepcidin peptide analogue
source                  1..9
                        mol_type = protein
                        organism = synthetic construct
SEQUENCE: 324
DRHFPCIIF                                                                   9

SEQ ID NO: 325          moltype = AA  length = 9
FEATURE                 Location/Qualifiers
REGION                  1..9
                        note = Hepcidin peptide analogue
source                  1..9
                        mol_type = protein
```

```
                            organism = synthetic construct
SEQUENCE: 325
DTKFPCIIF                                                                              9

SEQ ID NO: 326              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 326
DTHFECIIF                                                                              9

SEQ ID NO: 327              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 327
DTHFPCIIK                                                                              9

SEQ ID NO: 328              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 328
DTHFPCIIR                                                                              9

SEQ ID NO: 329              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 329
DTHFPCIEF                                                                              9

SEQ ID NO: 330              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 330
DTHFPCIVF                                                                              9

SEQ ID NO: 331              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 331
DTHFPCILF                                                                              9

SEQ ID NO: 332              moltype = AA   length = 9
FEATURE                     Location/Qualifiers
REGION                      1..9
                            note = Hepcidin peptide analogue
source                      1..9
                            mol_type = protein
                            organism = synthetic construct
SEQUENCE: 332
DTHFPCILK                                                                              9

SEQ ID NO: 333              moltype = AA   length = 9
FEATURE                     Location/Qualifiers
REGION                      1..9
                            note = Hepcidin peptide analogue
source                      1..9
```

```
                            mol_type = protein
                            organism = synthetic construct
SEQUENCE: 333
DTHFPCIEK                                                                    9

SEQ ID NO: 334              moltype = AA   length = 19
FEATURE                     Location/Qualifiers
REGION                      1..19
                            note = Hepcidine peptide analogue
source                      1..19
                            mol_type = protein
                            organism = synthetic construct
SEQUENCE: 334
DTHFPICIFG ARSKGWVMC                                                        19

SEQ ID NO: 335              moltype = AA   length = 25
FEATURE                     Location/Qualifiers
source                      1..25
                            mol_type = protein
                            organism = Homo sapiens
SEQUENCE: 335
DTHFPICIFC CGCCHRSKCG MCCKT                                                 25

SEQ ID NO: 336              moltype = AA   length = 9
FEATURE                     Location/Qualifiers
source                      1..9
                            mol_type = protein
                            organism = Homo sapiens
SEQUENCE: 336
DTHFPICIF                                                                    9

SEQ ID NO: 337              moltype = AA   length = 9
FEATURE                     Location/Qualifiers
REGION                      1..9
                            note = Retro inverse of mini-hepcidin peptide
SITE                        1..9
                            note = All amino acids are the D stereo isoform
source                      1..9
                            mol_type = protein
                            organism = synthetic construct
SEQUENCE: 337
FICIPFHTD                                                                    9

SEQ ID NO: 338              moltype = AA   length = 9
FEATURE                     Location/Qualifiers
REGION                      1..9
                            note = Dimerized peptide
DISULFID                    6
                            note = dimer linked through disulphide linkage
source                      1..9
                            mol_type = protein
                            organism = synthetic construct
SEQUENCE: 338
DTHFPCIIF                                                                    9

SEQ ID NO: 339              moltype = AA   length = 8
FEATURE                     Location/Qualifiers
REGION                      1..8
                            note = Dimerized peptide
DISULFID                    6
                            note = dimer linked through disulphide linkage
source                      1..8
                            mol_type = protein
                            organism = synthetic construct
SEQUENCE: 339
DTHFPCIF                                                                     8

SEQ ID NO: 340              moltype =    length =
SEQUENCE: 340
000

SEQ ID NO: 341              moltype = AA   length = 10
FEATURE                     Location/Qualifiers
REGION                      1..10
                            note = Dimerized peptide
DISULFID                    6
                            note = dimer linked through disulphide linkage
source                      1..10
                            mol_type = protein
```

```
                         organism = synthetic construct
SEQUENCE: 341
DTHFPCIKFF                                                              10

SEQ ID NO: 342           moltype = AA   length = 9
FEATURE                  Location/Qualifiers
REGION                   1..9
                         note = Dimerized peptide
DISULFID                 6
                         note = dimer linked through disulphide linkage
source                   1..9
                         mol_type = protein
                         organism = synthetic construct
SEQUENCE: 342
LTHFPCIIF                                                               9

SEQ ID NO: 343           moltype = AA   length = 9
FEATURE                  Location/Qualifiers
REGION                   1..9
                         note = Dimerized peptide
DISULFID                 6
                         note = dimer linked through disulphide linkage
source                   1..9
                         mol_type = protein
                         organism = synthetic construct
SEQUENCE: 343
ETHFPCIIF                                                               9

SEQ ID NO: 344           moltype = AA   length = 9
FEATURE                  Location/Qualifiers
REGION                   1..9
                         note = Dimerized peptide
DISULFID                 6
                         note = dimer linked through disulphide linkage
source                   1..9
                         mol_type = protein
                         organism = synthetic construct
SEQUENCE: 344
DTKFPCIIF                                                               9

SEQ ID NO: 345           moltype = AA   length = 9
FEATURE                  Location/Qualifiers
REGION                   1..9
                         note = Dimerized peptide
DISULFID                 6
                         note = dimer linked through disulphide linkage
source                   1..9
                         mol_type = protein
                         organism = synthetic construct
SEQUENCE: 345
DTHFPCIIK                                                               9

SEQ ID NO: 346           moltype = AA   length = 9
FEATURE                  Location/Qualifiers
REGION                   1..9
                         note = Dimerized peptide
DISULFID                 6
                         note = dimer linked through disulphide linkage
source                   1..9
                         mol_type = protein
                         organism = synthetic construct
SEQUENCE: 346
DTHFPCIIR                                                               9

SEQ ID NO: 347           moltype = AA   length = 9
FEATURE                  Location/Qualifiers
REGION                   1..9
                         note = Dimerized peptide
DISULFID                 6
                         note = dimer linked through disulphide linkage
source                   1..9
                         mol_type = protein
                         organism = synthetic construct
SEQUENCE: 347
DTHFPCIVF                                                               9

SEQ ID NO: 348           moltype = AA   length = 9
FEATURE                  Location/Qualifiers
REGION                   1..9
```

```
                        note = Dimerized peptide
DISULFID                6
                        note = dimer linked through disulphide linkage
source                  1..9
                        mol_type = protein
                        organism = synthetic construct
SEQUENCE: 348
DTHFPCILF                                                                        9

SEQ ID NO: 349          moltype = AA  length = 9
FEATURE                 Location/Qualifiers
REGION                  1..9
                        note = Dimerized peptide
DISULFID                6
                        note = dimer linked through disulphide linkage
source                  1..9
                        mol_type = protein
                        organism = synthetic construct
SEQUENCE: 349
DTHFPCILK                                                                        9

SEQ ID NO: 350          moltype = AA  length = 9
FEATURE                 Location/Qualifiers
REGION                  1..9
                        note = Dimerized peptide
DISULFID                6
                        note = dimer linked through disulphide linkage
source                  1..9
                        mol_type = protein
                        organism = synthetic construct
SEQUENCE: 350
DTHFPCIEK                                                                        9

SEQ ID NO: 351          moltype = AA  length = 9
FEATURE                 Location/Qualifiers
REGION                  1..9
                        note = Dimerized peptide
DISULFID                6
                        note = dimer linked through disulphide linkage
source                  1..9
                        mol_type = protein
                        organism = synthetic construct
SEQUENCE: 351
DTHFPCIIF                                                                        9

SEQ ID NO: 352          moltype = AA  length = 9
FEATURE                 Location/Qualifiers
REGION                  1..9
                        note = Dimerized peptide
DISULFID                6
                        note = dimer linked through disulphide linkage
source                  1..9
                        mol_type = protein
                        organism = synthetic construct
SEQUENCE: 352
DTHFPCIKF                                                                        9

SEQ ID NO: 353          moltype = AA  length = 9
FEATURE                 Location/Qualifiers
REGION                  1..9
                        note = Dimerized peptide
DISULFID                6
                        note = dimer linked through disulphide linkage
source                  1..9
                        mol_type = protein
                        organism = synthetic construct
SEQUENCE: 353
DTHFPCIKF                                                                        9

SEQ ID NO: 354          moltype = AA  length = 9
FEATURE                 Location/Qualifiers
REGION                  1..9
                        note = Hepcidin dimerized peptide
SITE                    1
                        note = CROSSLINK - Diethylene glycol linkage between Asp
                         residues of dimer
DISULFID                6
                        note = Disulphide linkage between Cys residues of dimer
source                  1..9
```

```
                        mol_type = protein
                        organism = synthetic construct
SEQUENCE: 354
DTHFPCIKF                                                               9

SEQ ID NO: 355          moltype = AA   length = 9
FEATURE                 Location/Qualifiers
REGION                  1..9
                        note = Hepcidin dimerized peptide
DISULFID                6
                        note = disulphide linkage between Cys residues of dimer
source                  1..9
                        mol_type = protein
                        organism = synthetic construct
SEQUENCE: 355
DTKFPCIRF                                                               9

SEQ ID NO: 356          moltype = AA   length = 9
FEATURE                 Location/Qualifiers
REGION                  1..9
                        note = Hepcidin dimerized peptide
SITE                    3
                        note = CROSSLINK - Diethylene glycol linkage between Lys
                         residues of dimer
DISULFID                6
                        note = disulphide linkage between Cys residues of dimer
source                  1..9
                        mol_type = protein
                        organism = synthetic construct
SEQUENCE: 356
DTKFPCIRF                                                               9

SEQ ID NO: 357          moltype = AA   length = 9
FEATURE                 Location/Qualifiers
REGION                  1..9
                        note = Hepcidin dimerized peptide
DISULFID                6
                        note = disulphide linkage between Cys residues of dimer
source                  1..9
                        mol_type = protein
                        organism = synthetic construct
SEQUENCE: 357
DTHFPCIKF                                                               9

SEQ ID NO: 358          moltype = AA   length = 9
FEATURE                 Location/Qualifiers
REGION                  1..9
                        note = Hepcidin dimerized peptide
DISULFID                6
                        note = disulphide linkage between Cys residues of dimer
SITE                    8
                        note = CROSSLINK - Diethylene glycol linkage between Lys
                         residues of dimer
source                  1..9
                        mol_type = protein
                        organism = synthetic construct
SEQUENCE: 358
DTHFPCIKF                                                               9

SEQ ID NO: 359          moltype = AA   length = 9
FEATURE                 Location/Qualifiers
REGION                  1..9
                        note = Hepcidin dimerized peptide
DISULFID                6
                        note = disulphide linkage between Cys residues of dimer
source                  1..9
                        mol_type = protein
                        organism = synthetic construct
SEQUENCE: 359
DTHFPCIRK                                                               9

SEQ ID NO: 360          moltype = AA   length = 9
FEATURE                 Location/Qualifiers
REGION                  1..9
                        note = Hepcidin dimerized peptide
DISULFID                6
                        note = disulphide linkage between Cys residues of dimer
VARIANT                 9
                        note = diethylene glycol linkage between Lys residues of
```

```
                        dimer
source                  1..9
                        mol_type = protein
                        organism = synthetic construct
SEQUENCE: 360
DTHFPCIRK                                                                 9

SEQ ID NO: 361          moltype = AA  length = 10
FEATURE                 Location/Qualifiers
REGION                  1..10
                        note = Hepcidin dimerized peptide
DISULFID                6
                        note = disulphide linkage between Cys residues of dimer
source                  1..10
                        mol_type = protein
                        organism = synthetic construct
SEQUENCE: 361
DTHFPCIKFK                                                               10

SEQ ID NO: 362          moltype = AA  length = 10
FEATURE                 Location/Qualifiers
REGION                  1..10
                        note = Hepcidin dimerized peptide
DISULFID                6
                        note = disulphide linkage between Cys residues of dimer
SITE                    10
                        note = CROSSLINK - diethylene glycol linkage between Lys
                         residues of dimer
source                  1..10
                        mol_type = protein
                        organism = synthetic construct
SEQUENCE: 362
DTHFPCIKFK                                                               10

SEQ ID NO: 363          moltype = AA  length = 9
FEATURE                 Location/Qualifiers
REGION                  1..9
                        note = Hepcidin dimerized peptide
source                  1..9
                        mol_type = protein
                        organism = synthetic construct
SEQUENCE: 363
DTHFPCIKF                                                                 9

SEQ ID NO: 364          moltype = AA  length = 9
FEATURE                 Location/Qualifiers
REGION                  1..9
                        note = Hepcidin dimerized peptide
source                  1..9
                        mol_type = protein
                        organism = synthetic construct
SEQUENCE: 364
DTHFPCIKF                                                                 9

SEQ ID NO: 365          moltype = AA  length = 10
FEATURE                 Location/Qualifiers
REGION                  1..10
                        note = Hepcidin dimerized peptide
source                  1..10
                        mol_type = protein
                        organism = synthetic construct
SEQUENCE: 365
DTHFPCIKFK                                                               10

SEQ ID NO: 366          moltype = AA  length = 9
FEATURE                 Location/Qualifiers
REGION                  1..9
                        note = Hepcidin dimerized peptide
source                  1..9
                        mol_type = protein
                        organism = synthetic construct
SEQUENCE: 366
DTHFPCIKF                                                                 9

SEQ ID NO: 367          moltype = AA  length = 19
FEATURE                 Location/Qualifiers
REGION                  1..19
                        note = Hepcidin dimerized peptide
SITE                    19
```

```
                        note = CROSSLINK - diethylene glycol linkage between Lys
                         residues of dimer
source                  1..19
                        mol_type = protein
                        organism = synthetic construct
SEQUENCE: 367
DTHFPCIIFG PRSRGWVCK                                                    19

SEQ ID NO: 368          moltype = AA   length = 18
FEATURE                 Location/Qualifiers
REGION                  1..18
                        note = Hepcidin dimerized peptide
SITE                    14
                        note = CROSSLINK - diethylene glycol linkage between Lys
                         residues of dimer
source                  1..18
                        mol_type = protein
                        organism = synthetic construct
SEQUENCE: 368
DTHFPICIFG PRSKGWVC                                                     18

SEQ ID NO: 369          moltype = AA   length = 17
FEATURE                 Location/Qualifiers
REGION                  1..17
                        note = Hepciding analogue peptide
source                  1..17
                        mol_type = protein
                        organism = synthetic construct
SEQUENCE: 369
DTHFPCIKFE PRSKECK                                                      17

SEQ ID NO: 370          moltype = AA   length = 17
FEATURE                 Location/Qualifiers
REGION                  1..17
                        note = Hepcidin analogue peptide
source                  1..17
                        mol_type = protein
                        organism = synthetic construct
SEQUENCE: 370
DTHFPCIKFE PHSKECK                                                      17

SEQ ID NO: 371          moltype = AA   length = 17
FEATURE                 Location/Qualifiers
REGION                  1..17
                        note = Hepcidin analogue pepide
source                  1..17
                        mol_type = protein
                        organism = synthetic construct
SEQUENCE: 371
DTHFPCIKKE PHSKECK                                                      17

SEQ ID NO: 372          moltype = AA   length = 17
FEATURE                 Location/Qualifiers
REGION                  1..17
                        note = Hepcidin analogue peptide
source                  1..17
                        mol_type = protein
                        organism = synthetic construct
SEQUENCE: 372
DTHFPCIKFK PHSKECK                                                      17

SEQ ID NO: 373          moltype = AA   length = 15
FEATURE                 Location/Qualifiers
REGION                  1..15
                        note = Hepcidin analogue peptide
source                  1..15
                        mol_type = protein
                        organism = synthetic construct
SEQUENCE: 373
DTHFPCIKFE PRECK                                                        15

SEQ ID NO: 374          moltype = AA   length = 15
FEATURE                 Location/Qualifiers
REGION                  1..15
                        note = Hepcidin analogue peptide
source                  1..15
                        mol_type = protein
                        organism = synthetic construct
SEQUENCE: 374
```

```
DTHFPCIKFE PHECK                                                        15

SEQ ID NO: 375         moltype = AA  length = 14
FEATURE                Location/Qualifiers
REGION                 1..14
                       note = Hepcidin analogue peptide
source                 1..14
                       mol_type = protein
                       organism = synthetic construct
SEQUENCE: 375
DTHFPCIKFE PRCK                                                         14
```